United States Patent
Godfrey et al.

(10) Patent No.: US 10,390,901 B2
(45) Date of Patent: Aug. 27, 2019

(54) OCULAR INJECTION KIT, PACKAGING, AND METHODS OF USE

(71) Applicant: Clearside Biomedical, Inc., Alpharetta, GA (US)

(72) Inventors: Thomas Edward Godfrey, Suwanee, GA (US); Rafael Victor Andino, Grayson, GA (US); Shelley Eckert Hancock, Atlanta, GA (US); Keleigh Jo Strudthoff, Atlanta, GA (US)

(73) Assignee: CLEARSIDE BIOMEDICAL, INC., Alpharetta, GA (US)

( * ) Notice: Subject to any disclaimer, the term of this patent is extended or adjusted under 35 U.S.C. 154(b) by 0 days.

(21) Appl. No.: 15/427,823

(22) Filed: Feb. 8, 2017

(65) Prior Publication Data

US 2017/0224435 A1 Aug. 10, 2017

Related U.S. Application Data

(60) Provisional application No. 62/293,526, filed on Feb. 10, 2016.

(51) Int. Cl.
*A61B 50/33* (2016.01)
*B65D 25/02* (2006.01)
(Continued)

(52) U.S. Cl.
CPC .............. *A61B 50/33* (2016.02); *A61B 50/20* (2016.02); *A61B 50/30* (2016.02); *A61F 9/0017* (2013.01);
(Continued)

(58) Field of Classification Search
CPC ... A61M 2209/06; A61M 5/002; A61B 50/33; A61B 2050/3015; A61F 9/0017;
(Continued)

(56) References Cited

U.S. PATENT DOCUMENTS

| 2,187,259 A | 1/1940 | Barnhart |
| 2,841,145 A | 7/1958 | Epps |

(Continued)

FOREIGN PATENT DOCUMENTS

| CA | 2639322 | 3/2009 |
| CN | 1706365 | 12/2005 |

(Continued)

OTHER PUBLICATIONS

Office Action for U.S. Appl. No. 11/743,535, dated Aug. 19, 2010, 7 pages.

(Continued)

*Primary Examiner* — Robert F Long
*Assistant Examiner* — Xavier A Madison
(74) *Attorney, Agent, or Firm* — Cooley LLP

(57) ABSTRACT

An apparatus includes a first tray member, a second tray member, and a lid. The first tray member has a first portion and a second portion. The first portion defines a first volume, and the second portion defines a second volume configured to receive a medicament container. The second tray member defines a third volume having a sidewall including a retention portion configured to retain an ocular injector within the third volume. The second tray member is coupled within first volume such that the sidewall of the second tray member and a sidewall of the first tray member enclose the ocular injector. The lid is coupled to the first tray member about the first volume, and is constructed from a material formulated to maintain sterility of the first volume.

30 Claims, 32 Drawing Sheets

(51) Int. Cl.
- *A61F 9/00* (2006.01)
- *B65D 77/04* (2006.01)
- *B65D 75/36* (2006.01)
- *B65D 25/20* (2006.01)
- *A61M 5/00* (2006.01)
- *A61J 1/00* (2006.01)
- *A61B 50/20* (2016.01)
- *A61B 50/30* (2016.01)
- *A61B 50/00* (2016.01)

(52) U.S. Cl.
CPC .............. *A61J 1/00* (2013.01); *A61M 5/002* (2013.01); *B65D 25/02* (2013.01); *B65D 25/205* (2013.01); *B65D 75/36* (2013.01); *B65D 77/0433* (2013.01); *A61B 2050/0065* (2016.02); *A61B 2050/3008* (2016.02); *A61B 2050/3015* (2016.02); *A61F 9/0008* (2013.01); *A61M 2209/06* (2013.01)

(58) Field of Classification Search
CPC ...... B65D 25/02; B65D 25/205; B65D 75/36; B65D 77/0433
USPC .......................................................... 53/492
See application file for complete search history.

(56) References Cited

U.S. PATENT DOCUMENTS

| | | |
|---|---|---|
| 2,939,459 A | 6/1960 | Lazarte et al. |
| 3,376,999 A | 4/1968 | De Hart et al. |
| 3,477,432 A | 11/1969 | Shaw |
| 3,739,947 A | 6/1973 | Baumann et al. |
| 3,762,540 A | 10/1973 | Baumann et al. |
| 3,788,320 A | 1/1974 | Dye |
| 3,892,311 A | 7/1975 | Sneider |
| 4,226,328 A | 10/1980 | Beddow |
| 4,377,897 A | 3/1983 | Fichenbaum et al. |
| 4,383,530 A | 5/1983 | Bruno |
| 4,417,887 A | 11/1983 | Koshi |
| 4,501,363 A * | 2/1985 | Isbey, Jr. ............... A61B 50/33 206/363 |
| 4,601,708 A | 7/1986 | Jordan |
| 4,615,331 A | 10/1986 | Kramann |
| 4,689,040 A | 8/1987 | Thompson |
| 4,708,147 A | 11/1987 | Haaga |
| 4,736,850 A * | 4/1988 | Bowman ............... A61F 2/0095 206/370 |
| 4,755,169 A | 7/1988 | Sarnoff et al. |
| 4,826,490 A | 5/1989 | Byrne et al. |
| 4,826,871 A | 5/1989 | Gressel et al. |
| 4,889,529 A | 12/1989 | Haindl |
| 4,941,874 A | 7/1990 | Sandow et al. |
| 4,966,773 A | 10/1990 | Gressel et al. |
| 5,066,276 A | 11/1991 | Wang |
| 5,098,389 A | 3/1992 | Cappucci |
| 5,137,447 A | 8/1992 | Hunter |
| 5,164,188 A | 11/1992 | Wong |
| 5,172,807 A | 12/1992 | Dragan et al. |
| 5,181,909 A | 1/1993 | McFarlane |
| 5,273,530 A | 12/1993 | del Cerro et al. |
| 5,279,564 A | 1/1994 | Taylor |
| 5,300,084 A | 4/1994 | Johnson |
| 5,312,361 A | 5/1994 | Zadini et al. |
| 5,354,286 A | 10/1994 | Mesa et al. |
| 5,364,373 A | 11/1994 | Waskonig et al. |
| 5,364,374 A | 11/1994 | Morrison et al. |
| 5,364,734 A | 11/1994 | Morrison et al. |
| 5,397,313 A | 3/1995 | Gross |
| 5,399,159 A | 3/1995 | Chin et al. |
| 5,407,070 A | 4/1995 | Bascos et al. |
| 5,443,505 A | 8/1995 | Wong et al. |
| 5,547,467 A | 8/1996 | Pliquett et al. |
| 5,632,740 A | 5/1997 | Koch et al. |
| D383,049 S | 9/1997 | Concari et al. |
| 5,667,491 A | 9/1997 | Pliquett et al. |
| 5,681,825 A | 10/1997 | Lindqvist et al. |
| 5,766,242 A | 6/1998 | Wong et al. |
| 5,767,079 A | 6/1998 | Glaser et al. |
| 5,779,668 A | 7/1998 | Grabenkort |
| 5,788,679 A | 8/1998 | Gravlee, Jr. |
| 5,792,099 A | 8/1998 | DeCamp et al. |
| 5,817,075 A | 10/1998 | Giungo |
| 5,824,072 A | 10/1998 | Wong |
| 5,911,223 A | 6/1999 | Weaver et al. |
| 5,952,378 A | 9/1999 | Stjernschantz et al. |
| 5,968,022 A | 10/1999 | Saito |
| 6,059,111 A | 5/2000 | Davila et al. |
| 6,083,199 A | 7/2000 | Thorley et al. |
| 6,143,329 A | 11/2000 | Kim |
| 6,280,470 B1 | 8/2001 | Peyman |
| 6,299,603 B1 | 10/2001 | Hecker et al. |
| 6,309,347 B1 | 10/2001 | Takahashi et al. |
| 6,309,374 B1 | 10/2001 | Hecker et al. |
| 6,319,240 B1 | 11/2001 | Beck |
| 6,334,856 B1 | 1/2002 | Allen et al. |
| 6,378,526 B1 | 4/2002 | Bowman et al. |
| 6,387,078 B1 | 5/2002 | Gillespie, III |
| 6,397,849 B1 | 6/2002 | Bowman et al. |
| 6,432,090 B1 | 8/2002 | Brunel |
| 6,503,231 B1 | 1/2003 | Prausnitz et al. |
| 6,524,581 B1 | 2/2003 | Adamis |
| 6,540,725 B1 | 4/2003 | Ponzi |
| 6,551,299 B2 | 4/2003 | Miyoshi et al. |
| 6,611,707 B1 | 8/2003 | Prausnitz et al. |
| 6,622,864 B1 | 9/2003 | Debbs et al. |
| 6,743,211 B1 | 6/2004 | Prausnitz et al. |
| 6,773,916 B1 | 8/2004 | Thiel et al. |
| D499,153 S | 11/2004 | Kuo |
| 6,883,222 B2 | 4/2005 | Landau |
| 6,918,889 B1 | 7/2005 | Brunel |
| 6,929,623 B2 | 8/2005 | Stone |
| 6,936,053 B1 | 8/2005 | Weiss |
| 7,025,774 B2 | 4/2006 | Freeman et al. |
| 7,150,735 B2 | 12/2006 | Hickle |
| 7,207,965 B2 | 4/2007 | Simon |
| 7,207,980 B2 | 4/2007 | Christian et al. |
| 7,211,062 B2 | 5/2007 | Kwon |
| 7,214,212 B2 | 5/2007 | Pommereau et al. |
| 7,226,439 B2 | 6/2007 | Prausnitz et al. |
| 7,316,676 B2 | 1/2008 | Peyman et al. |
| 7,425,207 B2 | 9/2008 | Miller et al. |
| 7,468,057 B2 | 12/2008 | Ponzi |
| D590,690 S | 4/2009 | Bertini |
| D598,543 S | 8/2009 | Vogel et al. |
| 7,569,035 B1 | 8/2009 | Wilmot et al. |
| 7,615,041 B2 | 11/2009 | Sullivan et al. |
| 7,678,077 B2 | 3/2010 | Harris et al. |
| 7,678,078 B1 | 3/2010 | Peyman et al. |
| 7,722,581 B2 | 5/2010 | Peyman |
| 7,914,803 B2 | 3/2011 | Chowhan |
| 7,918,814 B2 | 4/2011 | Prausnitz et al. |
| 7,918,874 B2 | 4/2011 | Siegal |
| 7,947,660 B2 | 5/2011 | Clark et al. |
| 7,967,772 B2 | 6/2011 | McKenzie et al. |
| 8,003,124 B2 | 8/2011 | Varner et al. |
| 8,114,110 B2 | 2/2012 | Bednarek et al. |
| 8,172,830 B2 | 5/2012 | Christian et al. |
| 8,173,617 B2 | 5/2012 | Clark et al. |
| 8,192,408 B2 | 6/2012 | Nazzaro et al. |
| 8,197,435 B2 | 6/2012 | Prausnitz et al. |
| 8,221,353 B2 | 7/2012 | Cormier et al. |
| 8,235,967 B2 | 8/2012 | Chevallier et al. |
| D667,111 S | 9/2012 | Robinson |
| 8,287,494 B2 | 10/2012 | Ma |
| 8,303,599 B2 | 11/2012 | Hess et al. |
| D672,506 S | 12/2012 | Szymanski |
| 8,323,227 B2 | 12/2012 | Hamatake et al. |
| 8,328,772 B2 | 12/2012 | Kinast et al. |
| 8,337,421 B2 | 12/2012 | Freeman et al. |
| 8,337,509 B2 | 12/2012 | Schieber et al. |
| 8,348,924 B2 | 1/2013 | Christian et al. |
| 8,403,941 B2 | 3/2013 | Peterson et al. |
| 8,430,862 B2 | 4/2013 | Peyman et al. |

(56) References Cited

U.S. PATENT DOCUMENTS

| | | |
|---|---|---|
| 8,448,786 B2 | 5/2013 | Tomes et al. |
| 8,460,242 B2 | 6/2013 | Paques et al. |
| 8,506,515 B2 | 8/2013 | Burns et al. |
| 8,529,492 B2 | 9/2013 | Clauson et al. |
| 8,535,333 B2 | 9/2013 | de Juan, Jr. et al. |
| 8,545,430 B2 | 10/2013 | Silvestrini |
| 8,545,554 B2 | 10/2013 | Novakovic et al. |
| 8,562,545 B2 | 10/2013 | Freeman et al. |
| 8,571,802 B2 | 10/2013 | Robinson et al. |
| 8,574,214 B2 | 11/2013 | Kuhn et al. |
| 8,574,217 B2 | 11/2013 | Peyman |
| 8,602,959 B1 | 12/2013 | Park et al. |
| 8,617,121 B2 | 12/2013 | Lanin et al. |
| 8,632,589 B2 | 1/2014 | Helmy |
| 8,636,713 B2 | 1/2014 | Prausnitz et al. |
| 8,652,118 B2 | 2/2014 | Peyman |
| 8,663,167 B2 | 3/2014 | Bartha |
| 8,663,303 B2 | 3/2014 | Horvath et al. |
| 8,668,676 B2 | 3/2014 | Chang |
| 8,685,435 B2 | 4/2014 | Nivaggioli et al. |
| 8,702,659 B2 | 4/2014 | Lanin et al. |
| 8,727,117 B2 | 5/2014 | Maasarani |
| 8,747,365 B2 | 6/2014 | De Sausmarez Lintell |
| 8,795,226 B2 | 8/2014 | Kuhn et al. |
| 8,808,225 B2 | 8/2014 | Prausnitz et al. |
| 8,808,242 B2 | 8/2014 | Paques et al. |
| D713,958 S | 9/2014 | Srinivasan et al. |
| 8,821,870 B2 | 9/2014 | Robinson et al. |
| D715,125 S | 10/2014 | Hung |
| 8,852,137 B2 | 10/2014 | Horvath et al. |
| 8,864,740 B2 | 10/2014 | Schabbach et al. |
| D718,602 S | 12/2014 | Musser |
| D719,256 S | 12/2014 | Ohashi |
| 8,920,375 B2 | 12/2014 | Gonnelli |
| D726,908 S | 4/2015 | Yu et al. |
| D733,289 S | 6/2015 | Blanchard et al. |
| D740,098 S | 10/2015 | Kuo et al. |
| 9,180,047 B2 | 11/2015 | Andino et al. |
| D750,223 S | 2/2016 | Andino et al. |
| 2001/0008961 A1 | 7/2001 | Hecker et al. |
| 2001/0051798 A1 | 12/2001 | Hochman |
| 2002/0042594 A1 | 4/2002 | Lum et al. |
| 2002/0052580 A1 | 5/2002 | Ooyauchi |
| 2002/0082527 A1 | 6/2002 | Liu et al. |
| 2002/0082543 A1 | 6/2002 | Park et al. |
| 2002/0108875 A1* | 8/2002 | Feinberg .......... A61B 17/00491 206/364 |
| 2002/0112981 A1 | 8/2002 | Cooper et al. |
| 2003/0009113 A1 | 1/2003 | Olson |
| 2003/0083645 A1 | 5/2003 | Angel et al. |
| 2003/0171722 A1 | 9/2003 | Paques et al. |
| 2004/0039253 A1 | 2/2004 | Peyman et al. |
| 2004/0106904 A1 | 6/2004 | Gonnelli et al. |
| 2004/0122359 A1 | 6/2004 | Wenz et al. |
| 2004/0199130 A1 | 10/2004 | Chornenky et al. |
| 2004/0215347 A1 | 10/2004 | Hayes |
| 2004/0249404 A1 | 12/2004 | Haefliger |
| 2004/0265365 A1 | 12/2004 | Daddona et al. |
| 2005/0033230 A1 | 2/2005 | Alchas et al. |
| 2005/0055083 A1* | 3/2005 | Carranza ................ A61B 50/30 623/1.23 |
| 2005/0065137 A1 | 3/2005 | Jani et al. |
| 2005/0089545 A1 | 4/2005 | Kuwano et al. |
| 2005/0101582 A1 | 5/2005 | Lyons et al. |
| 2005/0101882 A1 | 5/2005 | Leira et al. |
| 2005/0101967 A1 | 5/2005 | Weber et al. |
| 2005/0137525 A1 | 6/2005 | Wang et al. |
| 2005/0171507 A1 | 8/2005 | Christian et al. |
| 2005/0209565 A1 | 9/2005 | Yuzhakov et al. |
| 2005/0244462 A1 | 11/2005 | Farooq |
| 2005/0244469 A1 | 11/2005 | Whitcup et al. |
| 2005/0245906 A1 | 11/2005 | Makower et al. |
| 2005/0281862 A1 | 12/2005 | Karakelle et al. |
| 2006/0013859 A1 | 1/2006 | Yamada et al. |
| 2006/0032768 A1 | 2/2006 | Hamai et al. |
| 2006/0036318 A1 | 2/2006 | Foulkes |
| 2006/0084942 A1 | 4/2006 | Kim et al. |
| 2006/0086689 A1 | 4/2006 | Raju |
| 2006/0141049 A1 | 6/2006 | Lyons et al. |
| 2006/0173418 A1 | 8/2006 | Rinaudo et al. |
| 2006/0178614 A1 | 8/2006 | Nemati |
| 2006/0189608 A1 | 8/2006 | Bingaman |
| 2006/0229562 A1 | 10/2006 | Marsh et al. |
| 2006/0233858 A1 | 10/2006 | Tzekov et al. |
| 2006/0259008 A1 | 11/2006 | Orilla |
| 2006/0271025 A1 | 11/2006 | Jones et al. |
| 2007/0060927 A1 | 3/2007 | Longson et al. |
| 2007/0073197 A1 | 3/2007 | Prausnitz et al. |
| 2007/0082841 A1 | 4/2007 | Higuchi et al. |
| 2007/0093877 A1 | 4/2007 | Beecham et al. |
| 2007/0151882 A1 | 7/2007 | Cocheteux et al. |
| 2007/0178197 A1 | 8/2007 | Larue et al. |
| 2007/0202186 A1 | 8/2007 | Yamamoto et al. |
| 2007/0224278 A1 | 9/2007 | Lyons et al. |
| 2007/0225654 A1 | 9/2007 | Hess et al. |
| 2007/0233037 A1 | 10/2007 | Gifford et al. |
| 2007/0260201 A1 | 11/2007 | Prausnitz et al. |
| 2007/0270745 A1 | 11/2007 | Nczhat et al. |
| 2007/0270768 A1 | 11/2007 | Dacquay et al. |
| 2007/0287985 A1 | 12/2007 | Estes et al. |
| 2008/0033351 A1 | 2/2008 | Trogden et al. |
| 2008/0058704 A1 | 3/2008 | Hee et al. |
| 2008/0071246 A1 | 3/2008 | Nazzaro et al. |
| 2008/0082841 A1 | 4/2008 | Juenemann et al. |
| 2008/0097346 A1 | 4/2008 | Charles |
| 2008/0097390 A1 | 4/2008 | Dacquay et al. |
| 2008/0131484 A1 | 6/2008 | Robinson et al. |
| 2008/0177239 A1 | 7/2008 | Li et al. |
| 2008/0228127 A1 | 9/2008 | Burns et al. |
| 2009/0030381 A1 | 1/2009 | Lind et al. |
| 2009/0076463 A1 | 3/2009 | Attinger |
| 2009/0081277 A1 | 3/2009 | Robinson et al. |
| 2009/0105749 A1 | 4/2009 | De Juan et al. |
| 2009/0148527 A1 | 6/2009 | Robinson |
| 2009/0259180 A1 | 10/2009 | Choi |
| 2009/0287161 A1 | 11/2009 | Traub et al. |
| 2009/0312782 A1 | 12/2009 | Park |
| 2010/0010452 A1 | 1/2010 | Paques et al. |
| 2010/0012537 A1 | 1/2010 | Farrar et al. |
| 2010/0015158 A1 | 1/2010 | Robinson et al. |
| 2010/0057011 A1 | 3/2010 | Charles |
| 2010/0074957 A1 | 3/2010 | Robinson et al. |
| 2010/0100054 A1 | 4/2010 | Cormier et al. |
| 2010/0152646 A1 | 6/2010 | Girijavallabhan et al. |
| 2010/0152667 A1 | 6/2010 | Kietzmann |
| 2010/0173866 A1 | 7/2010 | Hee et al. |
| 2010/0191176 A1 | 7/2010 | Ho et al. |
| 2010/0211079 A1 | 8/2010 | Aramant |
| 2010/0312120 A1 | 12/2010 | Meier |
| 2011/0004265 A1 | 1/2011 | Wenger et al. |
| 2011/0060310 A1 | 3/2011 | Prestrelski et al. |
| 2011/0112546 A1 | 5/2011 | Juan, Jr. et al. |
| 2011/0166531 A1 | 7/2011 | Stroumpoulis et al. |
| 2011/0202012 A1 | 8/2011 | Bartlett |
| 2011/0213317 A1 | 9/2011 | Chen et al. |
| 2011/0238075 A1 | 9/2011 | Clauson et al. |
| 2011/0282298 A1 | 11/2011 | Again et al. |
| 2012/0004245 A1 | 1/2012 | May et al. |
| 2012/0024987 A1 | 2/2012 | Nagele Nacken |
| 2012/0029360 A1 | 2/2012 | Hendriks et al. |
| 2012/0035524 A1 | 2/2012 | Silvestrini |
| 2012/0078224 A1 | 3/2012 | Lerner et al. |
| 2012/0083727 A1 | 4/2012 | Barnett |
| 2012/0095414 A1 | 4/2012 | Lanin et al. |
| 2012/0095438 A1 | 4/2012 | Lanin et al. |
| 2012/0101475 A1 | 4/2012 | Wilmot et al. |
| 2012/0116306 A1 | 5/2012 | Heald et al. |
| 2012/0123351 A1 | 5/2012 | Lanin et al. |
| 2012/0123437 A1 | 5/2012 | Horvath et al. |
| 2012/0123440 A1 | 5/2012 | Horvath et al. |
| 2012/0123473 A1 | 5/2012 | Hernandez |
| 2012/0130207 A1 | 5/2012 | O'dea et al. |
| 2012/0136318 A1 | 5/2012 | Lanin et al. |
| 2012/0150128 A1 | 6/2012 | Zhao |

(56) References Cited

U.S. PATENT DOCUMENTS

| | | |
|---|---|---|
| 2012/0157880 A1 | 6/2012 | Haselby et al. |
| 2012/0165723 A1 | 6/2012 | Horvath et al. |
| 2012/0191064 A1 | 7/2012 | Conston et al. |
| 2012/0197208 A1 | 8/2012 | Bruggemann et al. |
| 2012/0226260 A1 | 9/2012 | Prausnitz et al. |
| 2012/0232522 A1 | 9/2012 | Prausnitz et al. |
| 2012/0259288 A1 | 10/2012 | Wagner et al. |
| 2012/0265149 A1 | 10/2012 | Lerner et al. |
| 2012/0271272 A1 | 10/2012 | Hammack et al. |
| 2013/0035662 A1 | 2/2013 | Decker et al. |
| 2013/0041265 A1 | 2/2013 | Sostek et al. |
| 2013/0060202 A1 | 3/2013 | Thorley et al. |
| 2013/0072900 A1 | 3/2013 | Colantonio |
| 2013/0079716 A1 | 3/2013 | Thorley et al. |
| 2013/0096533 A1 | 4/2013 | Freeman et al. |
| 2013/0102973 A1 | 4/2013 | Thorley et al. |
| 2013/0116523 A1 | 5/2013 | Jung et al. |
| 2013/0138049 A1 | 5/2013 | Kemp et al. |
| 2013/0140208 A1 | 6/2013 | Hemmann |
| 2013/0150803 A1 | 6/2013 | Shetty et al. |
| 2013/0190694 A1 | 7/2013 | Barrow-Williams et al. |
| 2013/0211335 A1 | 8/2013 | Paques et al. |
| 2013/0216623 A1 | 8/2013 | Yamamoto et al. |
| 2013/0218102 A1 | 8/2013 | Iwase et al. |
| 2013/0237910 A1 | 9/2013 | Shetty et al. |
| 2013/0237916 A1 | 9/2013 | Hanson et al. |
| 2013/0245600 A1 | 9/2013 | Yamamoto |
| 2013/0295006 A1 | 11/2013 | Christoforidis et al. |
| 2013/0331786 A1 | 12/2013 | Hofmann |
| 2013/0338612 A1 | 12/2013 | Smith et al. |
| 2014/0012226 A1 | 1/2014 | Hochman |
| 2014/0027326 A1 | 1/2014 | Peruzzo |
| 2014/0031833 A1 | 1/2014 | Novakovic et al. |
| 2014/0039391 A1 | 2/2014 | Clarke et al. |
| 2014/0039413 A1 | 2/2014 | Jugl et al. |
| 2014/0078854 A1 | 3/2014 | Head et al. |
| 2014/0094752 A1 | 4/2014 | Hiles |
| 2014/0102927 A1 | 4/2014 | Liversidge |
| 2014/0107566 A1 | 4/2014 | Prausnitz et al. |
| 2014/0114243 A1 | 4/2014 | Smith et al. |
| 2014/0135716 A1 | 5/2014 | Clarke et al. |
| 2014/0200518 A1 | 7/2014 | Ekman et al. |
| 2014/0224688 A1 | 8/2014 | Slemmen et al. |
| 2014/0231287 A1 | 8/2014 | Tomes et al. |
| 2014/0236098 A1 | 8/2014 | Mica et al. |
| 2014/0243754 A1 | 8/2014 | Clarke et al. |
| 2014/0249539 A1 | 9/2014 | Mica et al. |
| 2014/0257207 A1 | 9/2014 | Clarke et al. |
| 2014/0296802 A1 | 10/2014 | Geiger et al. |
| 2014/0309599 A1 | 10/2014 | Schaller |
| 2014/0323979 A1 | 10/2014 | Henley et al. |
| 2014/0323985 A1 | 10/2014 | Hourmand et al. |
| 2014/0330213 A1 | 11/2014 | Hourmand et al. |
| 2014/0350479 A1 | 11/2014 | Hourmand et al. |
| 2014/0353190 A1 | 12/2014 | Okihara et al. |
| 2015/0013827 A1 | 1/2015 | Kuhn |
| 2015/0013835 A1 | 1/2015 | Cordes |
| 2015/0025474 A1 | 1/2015 | Riedel et al. |
| 2015/0038905 A1 | 2/2015 | Andino et al. |
| 2015/0045731 A1 | 2/2015 | Gupta et al. |
| 2015/0045744 A1 | 2/2015 | Gupta et al. |
| 2015/0051545 A1 | 2/2015 | Henderson et al. |
| 2015/0051581 A1 | 2/2015 | Andino et al. |
| 2015/0129456 A1* | 5/2015 | Miller .................. A61B 10/025 206/571 |
| 2015/0133415 A1 | 5/2015 | Whitcup |
| 2015/0209180 A1 | 7/2015 | Prausnitz et al. |
| 2015/0320596 A1 | 11/2015 | Gifford, III et al. |
| 2016/0106584 A1 | 4/2016 | Andino et al. |
| 2016/0193080 A1 | 7/2016 | Hammack et al. |
| 2017/0095369 A1 | 4/2017 | Andino et al. |

FOREIGN PATENT DOCUMENTS

| | | |
|---|---|---|
| CN | 1736474 | 2/2006 |
| CN | 101052434 A | 10/2007 |
| EA | 006961 | 6/2006 |
| EP | 1568359 | 8/2005 |
| EP | 2193821 | 6/2010 |
| EP | 2307055 | 4/2011 |
| JP | 2001-525826 | 12/2001 |
| JP | 2009-531298 | 9/2009 |
| RU | 2344767 | 1/2009 |
| RU | 2353393 | 4/2009 |
| RU | 2428956 | 9/2011 |
| WO | WO 92/08406 | 5/1992 |
| WO | WO 94/01124 | 1/1994 |
| WO | WO 94/12217 | 6/1994 |
| WO | WO 96/09838 | 4/1996 |
| WO | WO 98/51348 | 11/1998 |
| WO | WO 2000/007530 | 2/2000 |
| WO | WO 2000/007565 | 2/2000 |
| WO | WO 2001/041685 | 6/2001 |
| WO | WO 2003/002094 | 1/2003 |
| WO | WO 2003/024507 | 3/2003 |
| WO | WO 2005/011741 | 2/2005 |
| WO | WO 2005/069831 | 8/2005 |
| WO | WO 2005/107845 | 11/2005 |
| WO | WO 2006/004595 | 1/2006 |
| WO | WO 2006/042252 | 4/2006 |
| WO | WO 2006/058189 | 6/2006 |
| WO | WO 2006/128034 | 11/2006 |
| WO | WO 2006/138719 | 12/2006 |
| WO | WO 2007/100745 | 9/2007 |
| WO | WO 2007/131050 | 11/2007 |
| WO | WO 2007/150018 | 12/2007 |
| WO | WO 2010/009034 | 1/2010 |
| WO | WO 2010/054660 | 5/2010 |
| WO | WO 2010/132751 | 11/2010 |
| WO | WO 2011/057065 | 5/2011 |
| WO | WO 2011/139713 | 11/2011 |
| WO | WO 2012/051575 | 4/2012 |
| WO | WO 2013/098166 | 7/2013 |
| WO | WO 2013/151904 | 10/2013 |
| WO | WO 2014/028285 | 2/2014 |
| WO | WO 2014/036009 | 3/2014 |
| WO | WO 2014/179698 | 11/2014 |
| WO | WO 2014/197317 | 12/2014 |
| WO | WO 2015/015467 | 2/2015 |
| WO | WO 2015/095772 | 6/2015 |
| WO | WO 2015/195842 | 12/2015 |
| WO | WO 2015/196085 | 12/2015 |
| WO | WO 2016/042162 | 3/2016 |
| WO | WO 2016/042163 | 3/2016 |

OTHER PUBLICATIONS

Office Action for U.S. Appl. No. 11/743,535, dated Dec. 29, 2009, 6 pages.
International Search Report and Written Opinion for International Application No. PCT/US2007/068055, dated Nov. 7, 2007, 13 pages.
Extended European Search Report for European Application No. 11777924.9, dated Feb. 4, 2015, 7 pages.
Office Action for Russian Application No. 2012147341, dated Feb. 26, 2015, 8 pages.
Office Action for U.S. Appl. No. 12/767,768, dated Jun. 10, 2011, 5 pages.
International Search Report and Written Opinion for International Application No. PCT/US2011/033987, dated Feb. 14, 2012, 7 pages.
Office Action for U.S. Appl. No. 13/447,246, dated Oct. 28, 2013, 5 pages.
Office Action for U.S. Appl. No. 13/453,407, dated Mar. 20, 2013, 5 pages.
Extended Search Report for European Application No. 13833318.2, dated Apr. 1, 2016.
Office Action for U.S. Appl. No. 14/424,685, dated Jun. 10, 2016, 10 pages.

(56) References Cited

OTHER PUBLICATIONS

Final Office Action for U.S. Appl. No. 14/424,685, dated Dec. 12, 2016.
International Search Report and Written Opinion for International Application No. PCT/US2013/056863, dated Nov. 26, 2013, 8 pages.
International Search Report and Written Opinion for International Application No. PCT/US2013/069156, dated Mar. 10, 2014, 11 pages.
Supplementary European Search Report for European Application No. 14808034.4, dated Jan. 23, 2017, 7 pages.
Office Action for U.S. Appl. No. 14/894,161, dated Dec. 27, 2016, 17 pages.
International Search Report and Written Opinion for International Application No. PCT/US2014/040254, dated Oct. 31, 2014, 9 pages.
Office Action for Eurasian Application No. 201592109, dated Apr. 1, 2016, 4 pages.
Extended Search Report for European Application No. 14791646.4, dated Nov. 21, 2016.
Search Report and Written Opinion for Singapore Application No. 11201509051V, dated Nov. 2, 2016, 6 pages.
Examination Report for Singapore Application No. 11201509051V, dated Feb. 1, 2017, 4 pages.
International Search Report and Written Opinion for International Application No. PCT/US2014/036590, dated Dec. 10, 2014, 10 pages.
Office Action for U.S. Appl. No. 14/268,687, dated May 19, 2016, 6 pages.
Office Action for U.S. Appl. No. 14/523,243, dated Feb. 27, 2015, 14 pages.
International Search Report and Written Opinion for International Application No. PCT/US2015/036299, dated Nov. 10, 2015, 11 pages.
International Search Report and Written Opinion for International Application No. PCT/US2015/036715, dated Jan. 19, 2016, 9 pages.
Office Action for Canadian Application No. 162010, dated Aug. 25, 2015.
International Search Report and Written Opinion for International Application No. PCT/US2014/071623, dated Jun. 25, 2015, 18 pages.
Office Action for Chinese Application No. 200780014501.3, dated Mar. 11, 2010, 6 pages.
Office Action for Chinese Application No. 200780014501.3, dated Aug. 26, 2010, 10 pages.
Office Action for European Application No. 07751620.1, dated Sep. 13, 2013.
Extended European Search Report for European Application No. 07751620.1, dated Jan. 15, 2013.
Office Action for European Application No. 07751620.1, dated Dec. 11, 2014.
Invitation pursuant to Article 94(3) and Rule 71(1) for European Application No. 07751620.1, dated Feb. 29, 2016, 3 pages.
Office Action for Japanese Application No. 2008-556462, dated Jul. 24, 2012.
Office Action for India Application No. 3345/KOLNP/2008, dated May 21, 2015.
Office Action for Singapore Application No. 200805936-2, dated Oct. 15, 2012.
Search Report and Written Opinion for Singapore Application No. 200805936-2, dated Jun. 8, 2010.
Supplementary Search Report for Singapore Application No. 200805936-2, dated May 6, 2011.
Supplementary Search Report for Singapore Application No. 200805936-2, dated May 26, 2011.
Office Action for U.S. Appl. No. 11/709,941, dated Jun. 24, 2014, 11 pages.
Office Action for U.S. Appl. No. 11/709,941, dated Mar. 23, 2011, 9 pages.
Office Action for U.S. Appl. No. 11/709,941, dated Feb. 11, 2015, 14 pages.
Office Action for U.S. Appl. No. 11/709,941, dated Oct. 27, 2011, 8 pages.
Office Action for U.S. Appl. No. 11/709,941, dated Apr. 12, 2016, 25 pages.
Office Action for U.S. Appl. No. 11/709,941, dated Dec. 27, 2016.
International Search Report and Written Opinion for International Application No. PCT/US2007/004874, dated Jun. 4, 2008.
Office Action for Chinese Application No. 201110093644.6, dated Mar. 26, 2012.
Office Action for Chinese Application No. 201110093644.6, dated Sep. 7, 2012.
Office Action for Chinese Application No. 201110093644.6, dated Dec. 14, 2012.
Office Action for U.S. Appl. No. 13/842,218, dated Jul. 5, 2016, 11 pages.
Office Action for U.S. Appl. No. 13/842,288, dated Oct. 6, 2015, 10 pages.
First Office Action for Chinese Application No. 201180060268.9, dated Oct. 10, 2014.
Second Office Action for Chinese Application No. 201180060268.9, dated Jun. 18, 2015.
Third Office Action for Chinese Application No. 201180060268.9, dated Feb. 5, 2016, 6 pages.
Fourth Office Action for Chinese Application No. 201180060268.9, dated Oct. 9, 2016.
Examination Report for European Application No. 11776049.6, dated Oct. 25, 2016.
Office Action for Japanese Application No. 2013-534049, dated Sep. 1, 2015, 11 pages.
Office Action for U.S. Appl. No. 13/273,775, dated Feb. 12, 2015, 13 pages.
Office Action for U.S. Appl. No. 13/273,775, dated Jul. 3, 2014, 12 pages.
International Search Report and Written Opinion for International Application No. PCT/US2011/056433, dated Apr. 25, 2012.
Office Action for Chinese Application No. 201510144330.2, dated Apr. 5, 2016.
Second Office Action for Chinese Application No. 201510144330.2, dated Dec. 20, 2016, 13 pages.
Abbott Medical Optics (HEALON5@OVD on http://ab-botttmedicaloptics.com/products/cataract/ovds/healon5-viscoelastic (2004).
Anthem, Medical Policy, Suprachoroidal Injection of a Pharmacologic Agent, Nov. 14, 2013, Retrieved from the Internet: <URL: http://www.anthem.com/medicalpolicies/policies/mp_pw_b076412.htm>, 3 pages.
Beer, P. J. et al., "Photographic Evidence of Vitreous Wicks After Intravitreal Injections," Retina Today, 2(2):24-39 (Mar. 2007).
Berglin, L. C. et al., "Tracing of Suprachoroidally Microneedle Injected Labled Drugs and Microbeads in Human, Pig and Rabbit Tissue Using Liquid Nitrogen Snap-Freeze Thaw and Lypholization Techniques," Invest Ophthalmol Vis Sci., 51:E-Abstract 5330 (2010), 2 pages.
Careforde Healthcare, B Braun Glass Loss-Of-Resistance Syringes 1# 332155—5cc Glass Loss-Of-Resistance Syringe, Luer Lock Metal Tip, 10/cs, [online], <http://careforde.com/b-braun-glass-loss-of-resistance-syringes-332155-5cc-glass-loss-of-r . . .> (2014), 2 pages.
Careforde Healthcare, B Braun Glass Loss-Of-Resistance Syringes # 332158—10cc Glass Loss-Of-Resistance Syringe, Luer Slip Metal Tip, 10/cs, (2014), 2 pages.
Carcforde Healthcare, B Braun Perifix Plastic Loss-Of-Resistance Syringes # 332152—8cc Plastic Luer Lock Loss-of-Resistance Syringe, 50/cs, [online], <http://careforde.com/b-braun-perifix-plastic-loss-of-resistance-syringes-332152-8cc-plasti . . .> (2014), 2 pages.
Choy, Y. B. et al., "Mucoadhesive microdiscs engineered for ophthalmic drug delivery: effect of particle geometry and fomulation on preocular residence time," Investigative Ophthalmology & Visual Science, 49:4808-4815 (2008).

(56) References Cited

OTHER PUBLICATIONS

Dinning, W.J., "Steroids and the eye-indications and complications," Postgraduate Medical Journal, vol. 52, 1976, pp. 634-638.
Edwards, A. et al., "Fiber matrix model of sclera and conical stroma for drug delivery to the eye," AIChE Journal, 44(1):214-225 (1998).
Einmahl, S. et al., "Evaluation of a novel biomaterial in the suprachoroidal space of the rabbit eye," Invest. Ophthalmol. Vis. Sci., 43(5):1533-1539 (2002).
Einmahl, S. et al., "Ocular biocompatibility of a poly(ortho ester) characterized by autocatalyzed degradation," J. Biomed. Mater. Res., 67(1):44-53 (2003).
"Epidural," Wikipedia [online], retrieved from the internet on Sep. 3, 2014, <URL:http:/en.wikipedia.org/wiki/Epidural>, 21 pages.
Feldkamp, L. A. et al., "Practical cone-beam algorithm," J. Opt. Soc. Am. A, 1(6):612-619 (1984).
Geroski, D. H. et al., "Drug delivery for posterior segment eye disease," Invest. Ophthahnol. Vis. Sci., 41(5):961-964 (2000).
Hanekamp, S. et al., "Inhibition of Corneal and Retinal Angiogenesis by Organic Integrin Antagonists After Intrascleral or Intravitreal Drug Delivery," Invest Ophthalmol Vis. Sci., 43: E-Abstract 3710, ARVO (2002), 2 pages.
Heller, J., Ocular delivery using poly(ortho esters), Adv. Drug. Deliv. Rev., 57(14):2053-2062 (2005).
Hoagan et al., Chapter Eight, Choroid, In Histology of the Human Eye, 9 pages (1971).
Jain, A., "Pseudo loss of resistance in epidural space localization: A complication of subcutaneous emphysema or simply a faulty technique," Saudi J. Anaseth, 5(1):108-109 (2011) (Abstract).
Jiang, J. et al., "Measurement and Prediction of Lateral Diffusion within Human Sclera," Investigative Ophthalmology & Visual Science, 47(7):3011-3016 (2006).
Jiang, J. et al., "Coated Microneedles for Drug Delivery to the Eye," Investigative Ophthalmology & Visual Science, 48(9):4038-4043 (2007).
Jiang, J. et al., "Intrascleral drug delivery to the eye using hollow microneedles," Pharmaceutical Research, 26(2):395-403 (2009).
Lee, S-B et al., "Drug delivery through the sclera: effects of thickness, hydration and sustained release systems," Experimental Eye Research, 78:599-607 (2004).
Lee et al., "Thixotropic property in pharmaceutical formulations," Journal of Controlled Release (2009) 136:88-98.
Lindfield, D. et al., "Suprachoroidal Devices in Glaucoma. The Past, Present, and Future of Surgery for Suprachoroidal Drainage," Cataract & Refractive Surgery Today [online], Oct. 2013, Retrieved from the Internet: <URL: http://bmctoday.net/crstodayeurope/2013/10/article.asp?f=suprachoroidal-devices-in-glau . . .>, 3 pages.
Loewen, N., "The suprachoroidal space in glaucoma surgery," Jul. 2012, 4 pages.
Maurice, D., "Review: Practical Issues in Intravitreal Drug Delivery," J. Ocul. Pharmacol. Ther., 17(4):393-401 (2001).
McAllister, D. V. et al., "Microfabricated needles for transdermal delivery of macromolecules and nanoparticles: Fabrication methods and transport studies," Proc. Nat'l Acad. Sci USA, 100(24):13755-13760 (2003).
Norman, D., Epidural analgesia using loss of resistance with air versus saline: Does it make a difference? Should we reevaluate our practice?, AANA Journal, 71(6):449-453 (Dec. 2003).
Olsen, T. W. et al., "Cannulation of the Suprachoroidal Space: A Novel Drug Delivery Methodology to the Posterior Segment," American J. Opthamology, 142(5):777-787 (2006).
Olsen, T., "Drug Delivery to the Suprachoroidal Space Shows Promise," Retina Today, pp. 36-39 (Mar./Apr. 2007).
Ozkiris, A., "intravitreal Triamcinolone Acetonide Injection for the Treatment of Posterior Uveitis," Ocular Immunology and Inflammation, vol. 14, Issue 4, pp. 233-238 (May 2006), Published online: Jul. 8, 2009 (Abstract).
Patel, S. R. et al., "Targeted administration into the suprachoroidal spcae using a microneedle for drug delivery to the posterior segment of the eye," Investigative Ophthalmology & Visual Science, 53(8):4433-4441 (Jul. 2012).
Patel, S. et al., "Suprachoroidal Drug Delivery Using Microneedles," Invest. Ophthalmol. Vis. Sci., 49:E-Abstract 5006 (2008), 2 pages.
Patel, S. et al., "Drug Binding to Sclera," Invest Ophthalmol Vis Sci., 50:E-Abstract 5968 (2009), 2 pages.
Patel, S. R. et al., "Intraocular Pharmacokinetics of Suprachoroidal Drug Delivery Administered Using Hollow Microneedles," Invest Ophthalmol Vis Sci., 51:E-Abstract 3796 (2010), 2 pages.
Penkov, M. A. et al., "A ten-year experience with usage of the method of supra-choroidal administration of medicinal substances," Oftalmol. Zh., 35(5):281-285 (1980).
Prausnitz, M. R. et al., "Permeability of cornea, sclera and conjunctiva: A literature analysis for drug delivery to the eye," Journal of Pharmaceutical Sciences, 87(12):1479-1488 (1998).
Prausnitz, M. R. et al., "Measurement and prediction of transient transport across sclera for drug delivery to the eye," Industrial and Engineering Chemistry Research, 37(8):2903-2907 (1998).
Prausnitz, M. R., "Microneedles for Ocular Drug Delivery," Review of Olsen, T., Drug Delivery to the Suprachoroidal Space Shows Promise, Retina Today, Mar./Apr. 2007, p. 39.
Rowe-Rendleman, C. L. et al., "Prophylactic Intra-Scleral Injection of Steroid Compounds in Rabbit Model of Retinal Neovascularization," Invest Ophthalmol Vis. Sci.,43:E-Abstract 3872, ARVO (2002), 2 pages.
Saberski, L. R. et al., "Identification of the epidural space: Is loss of resistance to air a safe technique? A review of the complications related to the use of air," Regional Anesthesia, 22(1):3-15 (1997).
Scott, I. U. et al., "Baseline characteristics and response to treatment of participants with hemiretinal compared with branch retinal or central retinal vein occlusion in the standard care vs. corticosteroid for retinal vein occlusion (SCORE)," Arch. Ophthalmol., 130(12):1517-1524 (Dec. 2012).
Shuler, R. K. et al., "Scleral Permeability of a Small, Single-Stranded Oligonucleotide," Journal of Ocular Pharmacology and Therapeutics, 20(2):159-168 (2004) (Abstract).
Wang, P. M. et al., "Minimally Invasive Extraction of Dermal Interstitial Fluid for Glucose Monitoring Using Microneedles," Diabetes Technology & Therapeutics, 7(1):131-141 (2005).
You, X. D. et al., "Chitosan drug delivery system implanting into suprachoroidal space for perforating ocular injury in rabbits," International Journal of Ophthalmology, 5(1):74-76 (2005) [English Abstract].
International Search Report and Written Opinion for International Application No. PCT/US2017/017014, dated Apr. 27, 2017, 13 pages.

* cited by examiner

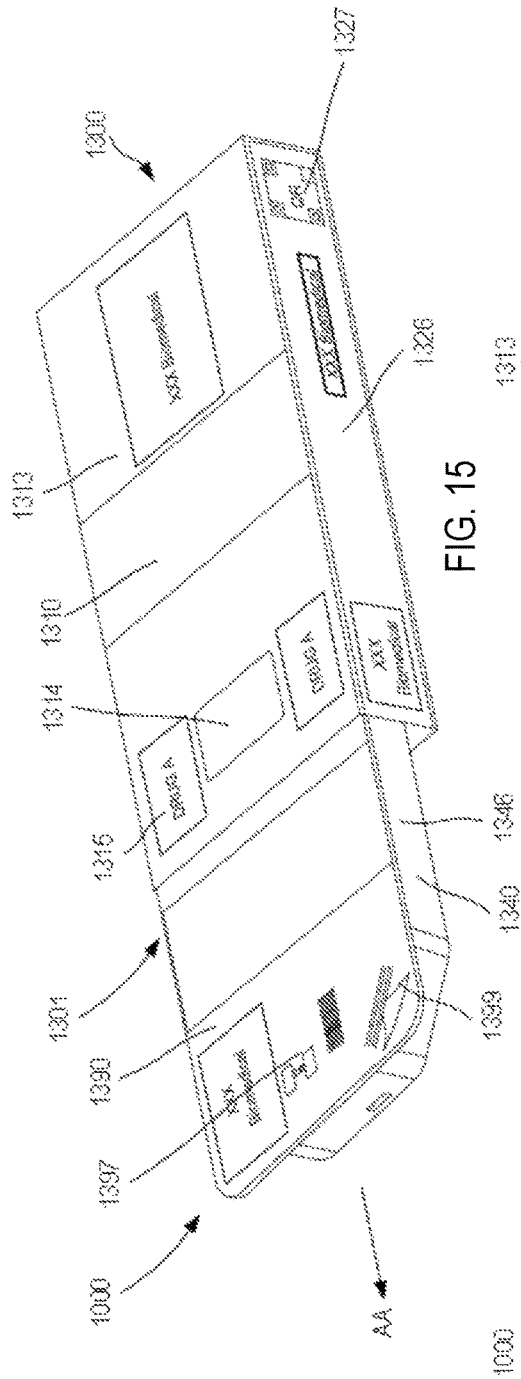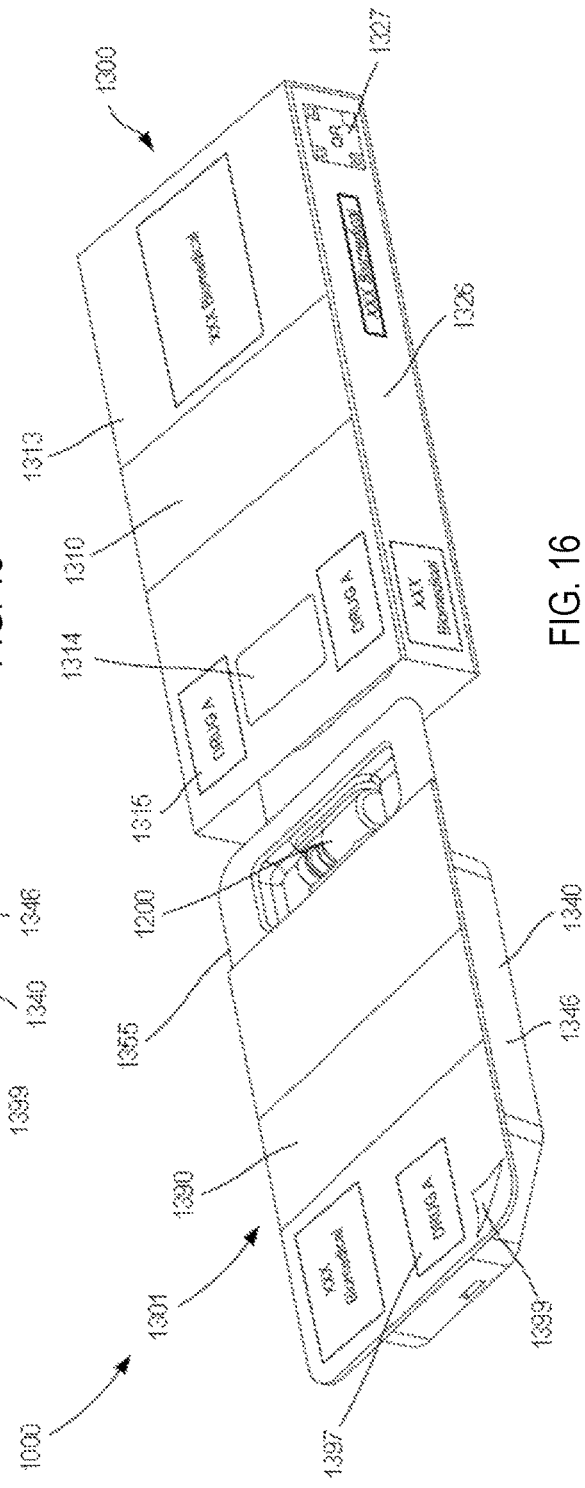

10

Remove a tray assembly from a sleeve, the tray assembly including a first tray member and a second tray member, the first tray member defining a first volume and a second volume, the second volume containing a medicament container, the second tray member defining a third volume within which an ocular injector is retained, the second tray member coupled within first volume such that a sidewall of the second tray member and a sidewall of the first tray member enclose the ocular injector
12

Optionally, remove a lid from the tray assembly thereby exposing the first volume
13

Orient the tray assembly such that an opening defined by the first tray member and providing access to the first volume is facing a sterile surface
14

Release the second tray member from within the first volume to place the second tray member on the sterile surface such that an opening defined by the second tray member and providing access to the third volume is facing opposite the sterile surface, a retention portion of the second tray member maintaining the ocular injector in a fixed position within the third volume
16

```
Optionally, remove a tray assembly from a sleeve, the tray assembly including a first
tray member and a second tray member, the first tray member defining a first volume
and an opening providing access to the first volume. The second tray member defines a
second volume within which a medicament delivery device is retained. The second tray
member is coupled within first volume such that a wall of the second tray member and a
wall of the first tray member enclose the medicament delivery device
22
```

↓

```
Optionally, remove a cover member from about the first volume
23
```

↓

```
Orient the tray assembly such that the opening of the first tray member is spaced apart
from and facing a sterile surface
24
```

↓

```
Release the second tray member from within the first volume to place the second tray
member on the sterile surface such that an opening defined by the second tray member
and providing access to the second volume is facing opposite the sterile surface, a
retainer of the second tray member maintaining the medicament delivery device in a
fixed position within the second volume
26
```

↓

```
Optionally, remove a medicament container from a container volume defined by the first tray
member
31
```

↓

```
Optionally, couple, after the releasing the second tray member, a reservoir of the medicament
delivery device to the medicament container via a adapter, the adapter stored within the first
volume
32
```

↓

```
Optionally, actuate the medicament delivery device to withdraw a dose of medicament from the
medicament container into the reservoir
33
```

FIG. 51

OCULAR INJECTION KIT, PACKAGING, AND METHODS OF USE

CROSS-REFERENCE TO RELATED APPLICATIONS

This application claims priority to and the benefit of U.S. Provisional Application Ser. No. 62/293,526, entitled "Ocular Injection Kit, Packaging, and Methods of Use," filed Feb. 10, 2016, which is incorporated herein by reference in its entirety.

BACKGROUND

The embodiments described herein relate generally to the field of ophthalmic therapies and more particularly to ocular injection devices, packaging systems and kits for delivery of a substance, such as a fluid therapeutic agent into ocular tissues for treatment of the eye.

Although injection is used in intraocular drug delivery, there remains a need for improved injection devices, kits, and methods, particularly for delivery of substances (e.g., drugs) into the posterior region of the eye. For example, in certain situations, direct injection of a medicament into the eye (e.g., into the vitreous) using conventional 27 gauge or 30 gauge needles and syringes can be effective. Direct injection, however, can be associated with significant safety risks. Such risks include, for example, controlling the needle depth and placement to deliver the medicament to the desired location (e.g., the suprachoroidal space (SCS) of the eye or the subretinal space (SRS) of the eye). It can be desirable, therefore for a kit or injection system to include a needle assembly that can vary or otherwise allow for different needle lengths during an injection procedure. It can also be desirable for a kit or injection system to include multiple interchangeable needles having different lengths to allow a practitioner to select the appropriate needle length at the time of an operation.

Needle insertion and injection can be further complicated in procedures where, due to the small needle size and/or the characteristics of the injected drug, delivery involves the use of force levels higher than that which users are comfortable with applying. For example, some studies have shown that users generally do not like to apply more than 2 N force against the eye during ocular injection. Accordingly, in certain situations a user may not properly deliver the medicament using known systems and methods because of their reluctance to apply the force to fully expel the medicament.

In addition to the issues surrounding the mechanics of needle insertion and injection, known kits and methods are also susceptible to risks associated with contamination. For example, known methods for accessing the eye include establishing a sterile field that is free of potentially harmful pathogens and/or microorganisms. Known kits, however, may include non-sterile portions (such as the exterior of the packaging, instructions or the like) that can contaminate the sterile field when the injection components are unpackaged and prepared for use.

Moreover, known some known kits are cumbersome to unpack and lack features that facilitate maintenance, handling, and/or manipulation of the components within a sterile field. For example, certain procedures may include preparing a dose of medicament within the sterile environment (e.g., within the sterile field) before delivery. The dose can be prepared, for example, by withdrawing a predetermined amount of a medicament from a vial into an injection device, by mixing one or more medicaments, by reconstituting a lyophilized medicament, or the like. Such dose preparation procedures can include handling one or more medicament containers, coupling the medicament containers to a delivery device (e.g., an ocular injector), and coupling a needle (or other delivery member) to the delivery device. Known kits, devices, and methods, however, often do not facilitate preserving the sterile field when such dose preparation and needle coupling operations are performed.

Thus, a need exists for improved injection devices, packaging systems and kits for ocular injection.

SUMMARY

Devices, packaging and kits for ocular injection are described herein. In some embodiments, an apparatus includes a first tray member, a second tray member, and a cover member. The first tray member has a first portion and a second portion. The first portion defines a first volume, and the second portion defines a container volume configured to receive a medicament container. The second tray member defines a second volume having a wall including a retainer configured to retain a medicament delivery device within the second volume. The second tray member is coupled within first volume such that the wall of the second tray member and a wall of the first tray member enclose the medicament delivery device. The cover member is coupled to the first tray member about the first volume, and is constructed from a material formulated to maintain sterility of the first volume.

BRIEF DESCRIPTION OF THE DRAWINGS

FIGS. 15 and 16 are top perspective views of the kit shown in FIGS. 13 and 14 being transitioned from a first configuration to a second configuration.

FIG. 50 is a flow chart of a method of preparing an ocular injection according to an embodiment.

FIG. 51 is a flow chart of a method of preparing an ocular injection according to an embodiment

DETAILED DESCRIPTION

Figure 1:
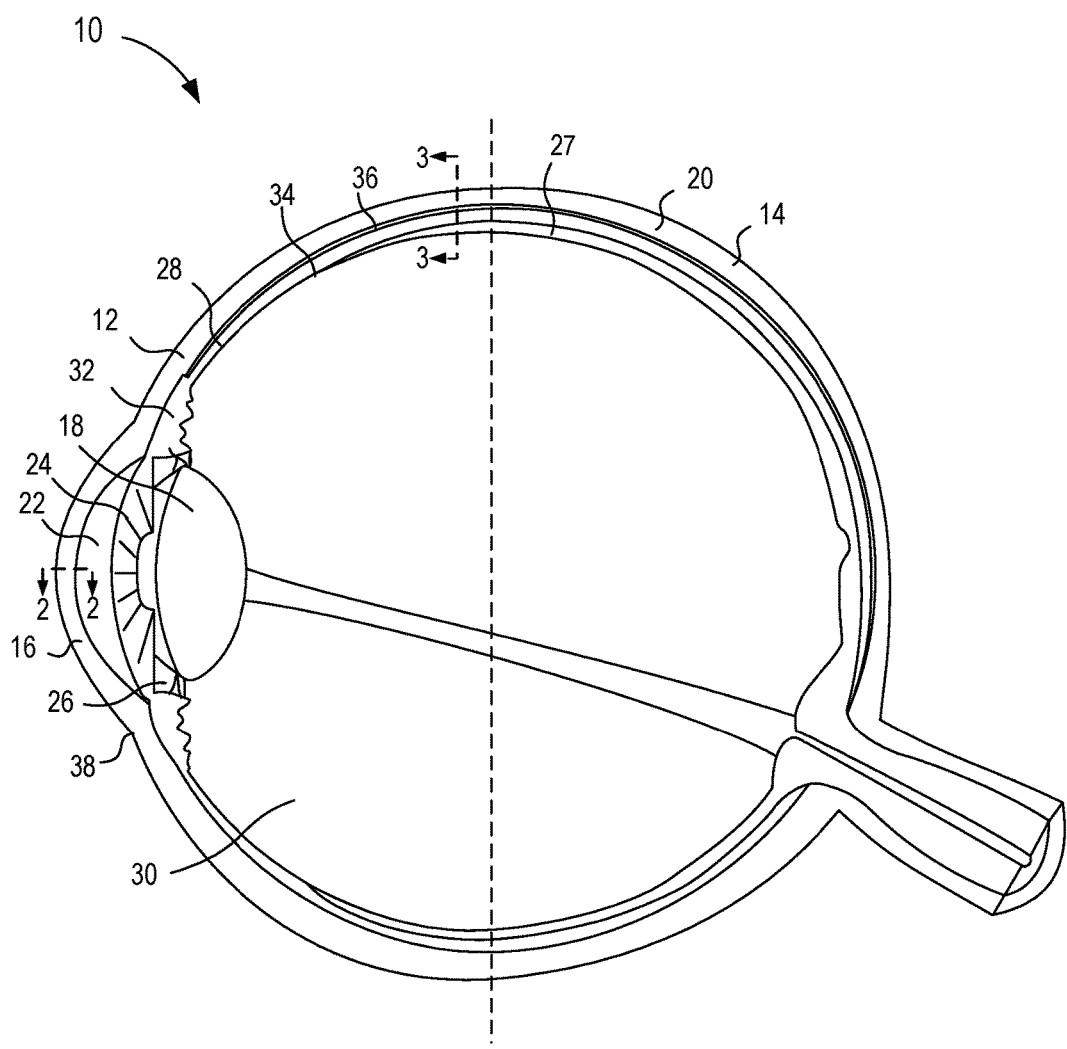
FIG. 1 is a cross-sectional view of an illustration of the human eye.

Devices, packaging and kits for ocular injection are described herein. In some embodiments, an apparatus includes a first tray member, a second tray member, and a cover member. The first tray member has a first portion and a second portion. The first portion defines a first volume, and the second portion defines a container volume configured to receive a medicament container. The second tray member defines a second volume having a wall including a retainer configured to retain a medicament delivery device within the second volume. The second tray member is coupled within first volume such that the wall of the second tray member and a wall of the first tray member enclose the medicament delivery device. The cover member is coupled to the first tray member about the first volume, and is constructed from a material formulated to maintain sterility of the first volume.

In some embodiments, an apparatus includes a first tray member, a second tray member, and a cover member. The first tray member defines a first volume and an opening providing access to the first volume. The second tray member defines a second volume. A wall of the second tray member includes a retainer configured to retain at least a portion of a medicament delivery device within the second volume. The second tray member is configured to be disposed within first volume such that the wall of the second tray member and a wall of the first tray member enclose the medicament delivery device within the first volume. The cover member is coupled to the first tray member about the opening, and is configured to maintain sterility of the first volume.

In some embodiments, an apparatus includes a first tray member, a second tray member, and a cover member. The first tray member has a first portion and a second portion. The first portion defines a first volume, and the second portion defines a container volume. The container volume is configured to receive a medicament container. The second tray member defines a second volume, and includes a retainer configured to retain a medicament delivery device within the second volume. The second tray member is configured to be coupled within the first volume such that the medicament delivery device is disposed within the first volume. The cover member is configured to be coupled to the first tray member about the first volume, and is configured to maintain sterility of the first volume. The container volume is exposed when the cover member is coupled to the first tray member.

In some embodiments, a kit includes a medical injector, a medicament container, and a tray assembly. The tray assembly includes a first tray member, a second tray member, and a cover member. The first tray member defines a first volume and a container volume. The medicament container is retained within the container volume. The second tray member defines a second volume within which the medical injector is disposed. A wall of the second tray member includes a retention portion that retains the medical injector within the second volume. The second tray member is coupled within first volume such that the wall of the second tray member and a wall of the first tray member enclose the medical injector. The cover member is coupled to the first tray member about the first volume, and is constructed from a material formulated to maintain sterility of the first volume.

In some embodiments, a method includes orienting a tray assembly such that an opening defined by a first tray member is spaced apart from and facing a sterile surface. The tray assembly includes the first tray member and a second tray member. The first tray member defines a first volume, to which the opening provides access. The second tray member defines a second volume within which a medicament delivery device is retained. The second tray member is coupled within the first volume such that a wall of the second tray member and a wall of the first tray member enclose the medicament delivery device. The method further includes releasing the second tray member from within the first volume to place the second tray member on the sterile surface such that an opening defined by the second tray member and providing access to the second volume is facing opposite the sterile surface. A retainer of the second tray member maintains the medicament delivery device in a fixed position within the second volume.

In some embodiments, a method includes removing a tray assembly from a sleeve. The tray assembly includes a first tray member and a second tray member. The first tray member defines a first volume and a container volume, the container volume containing a medicament container. The second tray member defines a second volume within which an ocular injector is retained. The second tray member is coupled within first volume such that a wall of the second tray member and a wall of the first tray member enclose the ocular injector. The tray assembly is oriented such that an opening defined by the first tray member (that provides access to the first volume) is facing a sterile surface. The tray assembly is maintained spaced apart from the sterile surface. The method includes releasing the second tray member from within the first volume to place the second tray member on the sterile surface. The second tray member is placed such that an opening defined by the second tray member (and that provides access to the second volume) is facing opposite the sterile surface. A retention portion of the second tray member maintains the ocular injector in a fixed position within the second volume.

The term "about" when used in connection with a referenced numeric indication means the referenced numeric indication plus or minus up to 10 percent of that referenced numeric indication. For example, "about 100" means from 90 to 110.

As used herein, the singular forms "a," "an", and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to the direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the end of a microneedle or injection device described herein first inserted inside the patient's body would be the distal end, while the opposite end of the microneedle or injection device (e.g., the end of the medical device being manipulated by the operator) would be the proximal end of the microneedle.

As used herein, a "set" can refer to multiple features or a singular feature with multiple parts. For example, when referring to set of walls, the set of walls can be considered as one wall with distinct portions, or the set of walls can be considered as multiple walls.

As used herein, the terms "medicament container," and "medicament containment chamber" are used interchangeably to refer to an article configured to contain a volume of a substance, for example, a medicament. A medicament container can include a vial, ampule (or ampoule), inner portion of a syringe, or the like.

As used in this specification and the appended claims, the term "medicament" includes any constituent of a therapeutic substance. A medicament can include such constituents regardless of their state of matter (e.g., solid, liquid or gas). Moreover, a medicament can include the multiple constituents that can be included in a therapeutic substance in a mixed state, in an unmixed state and/or in a partially mixed state. A medicament can include both the active constituents and inert constituents of a therapeutic substance. Accordingly, as used herein, a medicament can include non-active constituents such as, water, colorant or the like.

Figure 2:
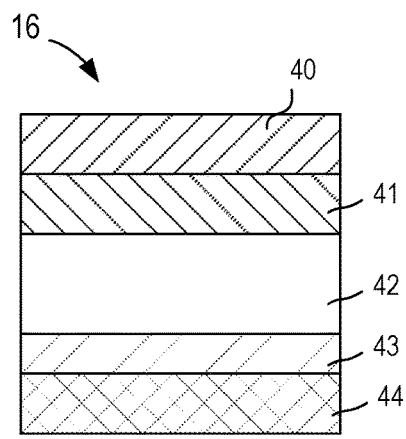
FIG. 2 is a cross-sectional view of a portion of the human eye of FIG. 1 taken along the line 2-2.
Figure 3:
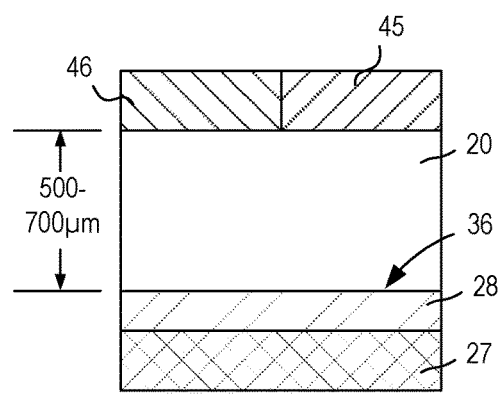
FIGS. 3 and 4 are cross-sectional views of a portion of the human eye of FIG. 1 taken along the line 3-3, illustrating the suprachoroidal space without and with, respectively, the presence of a fluid.
Figure 4:
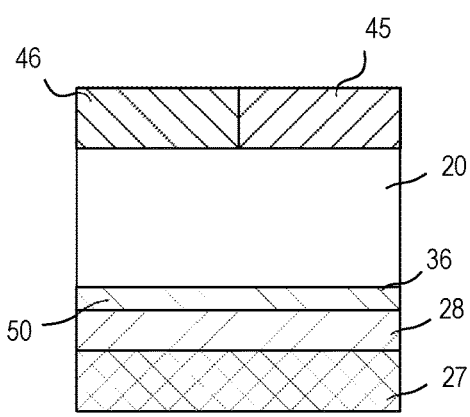

As used herein, "ocular tissue" and "eye" include both the anterior segment of the eye (i.e., the portion of the eye in front of the lens) and the posterior segment of the eye (i.e., the portion of the eye behind the lens). For reference, FIGS. 1-4 are a various views of an eye 10 (with FIGS. 2-4 being cross-sectional views). While specific regions are identified, those skilled in the art will recognize that the proceeding identified regions do not constitute the entirety of the eye 10, rather the identified regions are presented as a simplified example suitable for the discussion of the embodiments herein. The eye 10 includes both an anterior segment 12 (the portion of the eye in front of and including the lens) and a posterior segment 14 (the portion of the eye behind the lens). The anterior segment 12 is bounded by the cornea 16 and the lens 18, while the posterior segment 14 is bounded by the sclera 20 and the lens 18. The anterior segment 12 is further subdivided into the anterior chamber 22, between the iris 24 and the cornea 16, and the posterior chamber 26, between the lens 18 and the iris 24. The cornea 16 and the sclera 20 collectively form a limbus 38 at the point at which they meet. The exposed portion of the sclera 20 on the anterior segment 12 of the eye is protected by a clear membrane referred to as the conjunctiva 45 (see e.g., FIGS. 2 and 3). Underlying the sclera 20 is the choroid 28 and the retina 27, collectively referred to as retinachoroidal tissue. A vitreous humour 30 (also referred to as the "vitreous") is disposed between a ciliary body 32 (including a ciliary muscle and a ciliary process) and the retina 27. The anterior portion of the retina 27 forms an ora serrata 34. The loose connective tissue, or potential space, between the choroid 28 and the sclera 20 is referred to as the suprachoroid. FIG. 2 illustrates the cornea 16, which is composed of the epithelium 40, the Bowman's layer 41, the stroma 42, the Descemet's membrane 43, and the endothelium 44. FIG. 3 illustrates the sclera 20 with surrounding Tenon's Capsule 46 or conjunctiva 45, suprachoroidal space 36, choroid 28, and retina 27, substantially without fluid and/or tissue separation in the suprachoroidal space 36 (i.e., the in this configuration, the space is "potential" suprachoroidal space). As shown in FIG. 3, the sclera 20 has a thickness between about 500 µm and 700 µm. FIG. 4 illustrates the sclera 20 with the surrounding Tenon's Capsule 46 or the conjunctiva 45, suprachoroidal space 36, choroid 28, and retina 27, with fluid 50 in the suprachoroidal space 36.

The dashed line in FIG. 1 represents the equator of the eye 10. In some embodiments, the insertion site of any of the microneedles and/or methods described herein is between the equator and the limbus 38 (i.e., in the anterior portion 12 of the eye 10) For example, in some embodiments, the insertion site is between about two millimeters and 10 millimeters (mm) posterior to the limbus 38. In other embodiments, the insertion site of the microneedle is at about the equator of the eye 10. In still other embodiments, the insertion site is posterior the equator of the eye 10. In this manner, a drug formulation can be introduced (e.g., via the microneedle) into the suprachoroidal space 36 at the site of the insertion and can flow through the suprachoroidal space 36 away from the site of insertion during an infusion event (e.g., during injection).

In some embodiments, a kit for delivering a medicament can include a medicament delivery device and the packaging (or additional components) that facilitates the desired delivery process (e.g., injection, topical application, inhalation, or the like) in a sterile environment. Similarly stated, in some embodiments, the packaging can facilitate maintaining the sterility of the delivery device, the medicament container(s), or the like during the handling and preparation of these components. For example, FIGS. 5-8 are schematic illustrations of a medicament delivery kit 2000 (also referred to as a "kit" or a medicament delivery system), according to an embodiment. FIGS. 5-8 show the kit 2000 in a first configuration, a second configuration, a third configuration, and a fourth configuration, respectively. The kit 2000 includes a packaging assembly 2300 that contains a medicament delivery device 2100 (see FIG. 8). The medicament delivery device 2100 can be any suitable device (or collection of components) for delivering a medicament via any suitable method. For example, in some embodiments, the medicament delivery device 2100 can be an ocular injector of the types shown and described herein and in International Patent Application No. WO2015/19584, entitled "METHODS AND DEVICES FOR TREATING POSTERIOR OCULAR DISORDERS" and U.S. Pat. No. 9,180,047, entitled "APPARATUS AND METHODS FOR OCULAR INJECTION," each of which is incorporated herein by reference in its entirety. Although the medicament delivery device 2100 is shown schematically in FIG. 8 as including multiple components that are stored separately within the packaging assembly 2300, in other embodiments, the medicament delivery device 2100 (or any other medicament delivery device described herein) can be a single, pre-assembled device (e.g., a prefilled syringe). Such a pre-assembled device can include a dose of any suitable medicament of the types shown and described herein. For example, in some embodiments, the medicament delivery device 2100 can include triamcinolone or triamcinolone acetonide. In other embodiments, the medicament delivery device 2100 can be stored separately from a medicament container containing a dose of the medicament (e.g., any suitable medicament of the types shown and described herein). For example, in some embodiments, the kit 2000 can include a separate medicament container (not shown) containing triamcinolone or triamcinolone acetonide. Moreover, the medicament delivery device 2100 can be any suitable device or drug product, such as a syringe (i.e., a manually-actuated injector), an auto-injector, a nasal delivery device, an inhaler, a nebulizer, or any other suitable device.

The packaging assembly 2300 includes a first tray member 2340, a second tray member 2365 (see FIGS. 7 and 8), and a cover member 2390. The first tray member 2340 includes a wall 2348 (also referred to as a sidewall or a body) defining a first volume 2347 and an opening 2351 that provides access to the first volume 2347. The first tray member 2340 can be of any suitable shape or size. For example, although shown as being substantially cylindrical, in other embodiments, the first tray member 2340 (and any of the tray members described herein) can have an oval cross-sectional shape, a rectangular cross-sectional shape, or a polygonal cross-sectional shape (e.g. five-sided, six-sided, or the like). Moreover, although the first tray member 2340 is shown as having a substantially constant cross-sectional size (i.e., the cross-sectional size along an axis perpendicular to the plane of the opening 2351 is non-tapered), in other embodiments, the shape of the first tray member 2340 (or any other tray members described herein) can be variable over the height of the tray member, or can otherwise be irregular.

Figure 7:
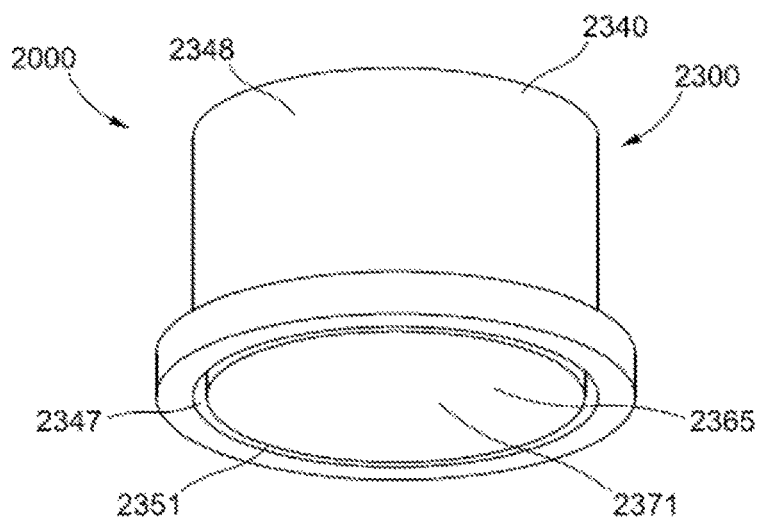
Figure 8:
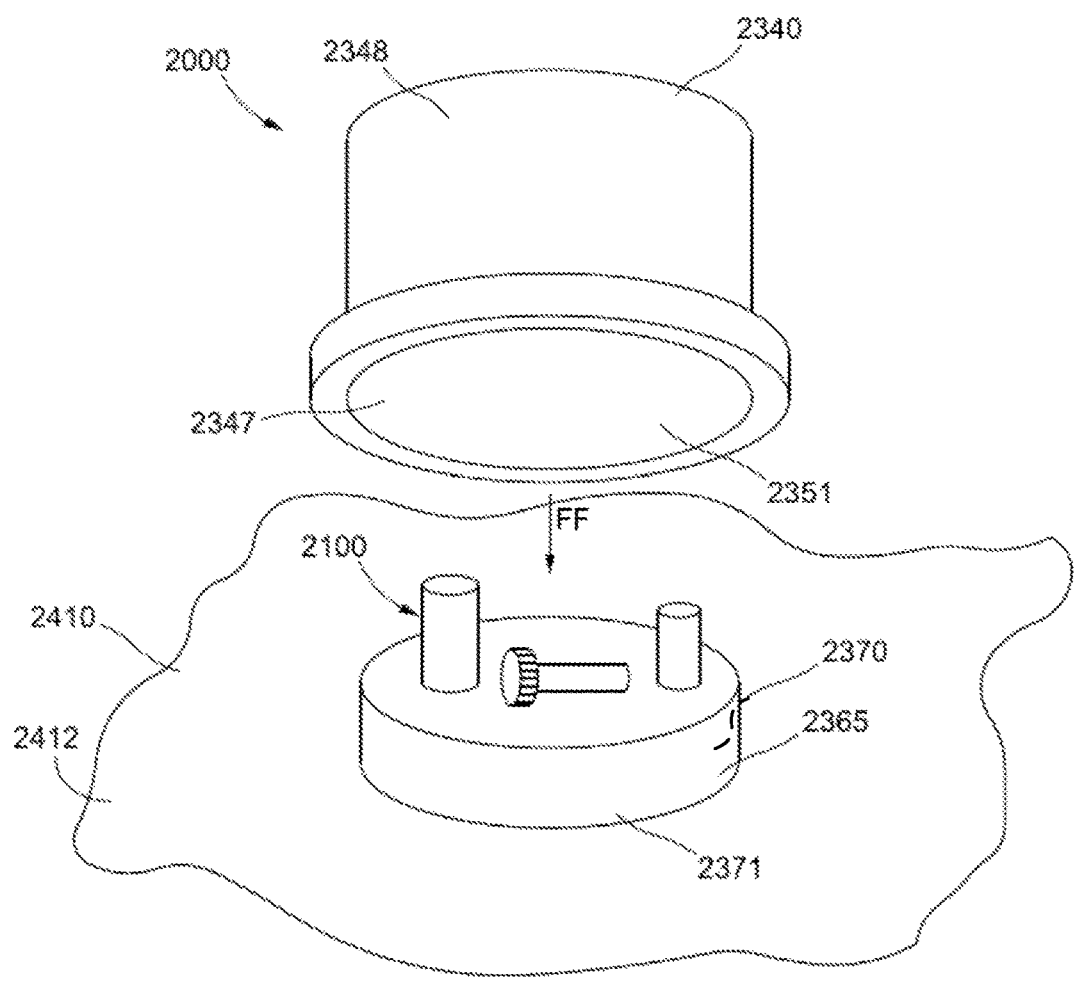

Referring to FIGS. 7 and 8, the second tray member 2365 includes a wall 2371 (also referred to as a sidewall or a body) defining a second volume 2370. The second volume 2370 can be of any suitable shape and/or size to contain or receive at least a portion of the medicament delivery device 2100. For example, in some embodiments, the second volume 2370 can be a continuous volume (e.g., a cylindrical volume) within which the portion of the medicament delivery device 2100 is contained. In other embodiments, the second volume 2370 can be a series of disconnected (or non-contiguous) volumes defined by the wall 2371 within which different portions of the medicament delivery device 2100 are contained. For example, in some embodiments, the second volume 2370 (or any of the second volumes described herein) can include a first "cut-out" or volume that receives a barrel of a medical injector, a second distinct "cut-out" or volume that receives a needle of the medical injector, and a third distinct "cut-out" or volume that receives yet another portion of the medical injector. Additionally, the second tray member 2365 is configured to retain, contain and/or hold at least a portion of the medicament deliver device 2100 within the second volume 2370. For example, in some embodiments, the second tray member 2365 can include a retainer, such as a portion of the wall 2371 that defines an opening within which the portion of the medicament delivery device 2100 is press fit. In other embodiments, the second tray member 2365 can include a separate retainer, such as a band, a rotatable arm or other movable member that engages and/or contacts the portion of the medicament delivery device 2100 to retain the device 2100 within the second volume 2370.

Figure 5:
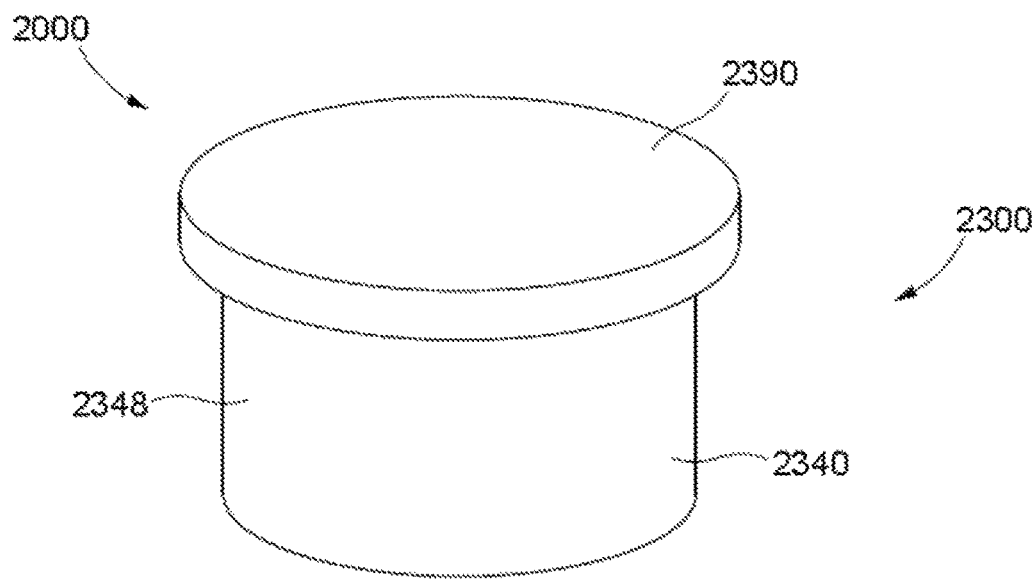
FIGS. 5-8 are schematic illustrations of a kit according to an embodiment, in a first configuration, second configuration, third configuration, and fourth configuration, respectively.
Figure 6:
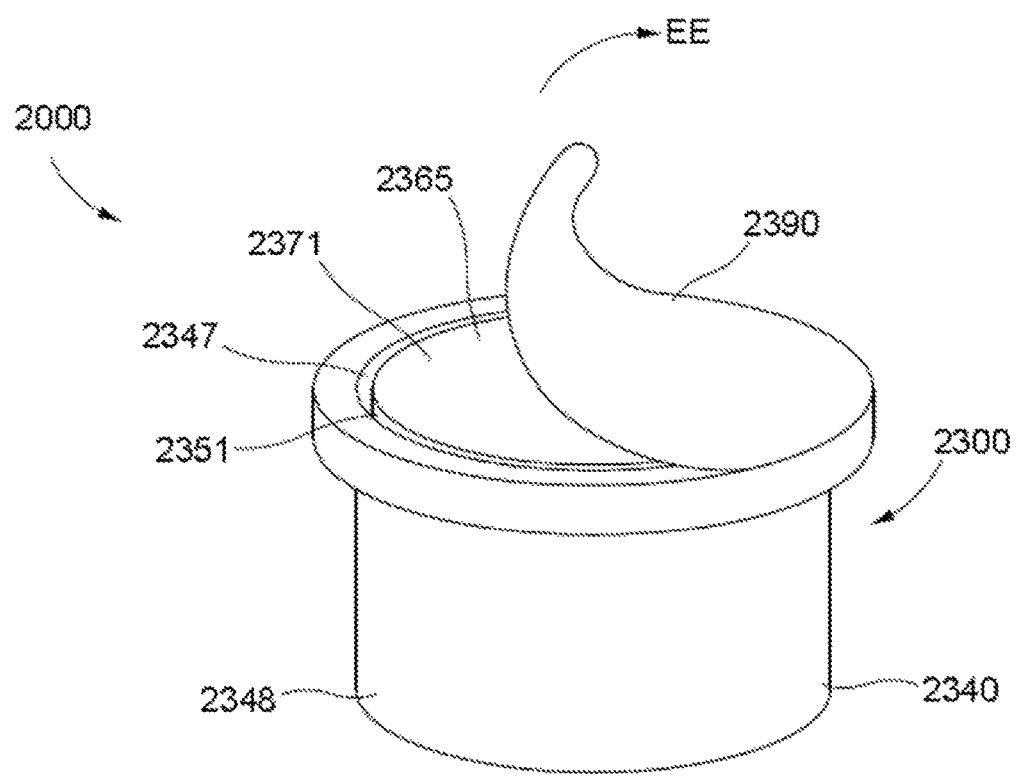

The second tray member 2365 is configured to be disposed within first volume 2347 such that the wall 2371 of the second tray member 2365 and the wall 2348 of the first tray member 2340 enclose the medicament delivery device 2100 within the first volume 2347. Similarly stated, the when the medicament delivery kit 2000 is assembled (i.e., in its first configuration, as shown in FIG. 5), the wall 2348 of the first tray member 2340 and the wall 2371 of the second tray member 2365 surround the medicament delivery device 2100. Said another way, as shown in FIGS. 5-7 when the medicament delivery kit 2000 is in the first configuration, the second configuration, and/or the third configuration, the second tray member 2365 is disposed (or "nested") within the first tray member 2340 such that the medicament delivery device 2100 is maintained within the first volume 2347. In this manner, after the first volume is sterilized (e.g., during assembly of the kit 2000), the medicament delivery device 2100 is maintained within the sterile first volume 2347.

In some embodiments, the second tray member 2365 is positioned within the first tray member 2340 such that the opening 2351 of the first tray member 2340 is obstructed by the wall 2371 of the second tray member 2365. Specifically, as shown in FIGS. 6 and 7, the bottom portion of the wall 2371 covers or obstructs the opening 2351. Moreover, any openings (not shown) defined by the second tray 2365 and providing access to the second volume 2370 can also be covered by the wall 2348 of the first tray member 2340. For example, the bottom portion of the wall 2348 can cover any central opening, any retainer openings or the like. In this manner, the inverted position of the second tray member 2365 within the first tray member 2340 (i.e., the "open side" of the second tray member 2365 facing inward) facilitates obstructing the opening 2351 of the first tray member 2340 to facilitate maintaining the sterility of the first volume 2347 during use.

As described herein, the second tray member 2365 is disposed within the first tray member 2340 in an inverted position (i.e., the "open side" of the second tray member 2365 facing inward). In this arrangement, the bottom portion of the wall 2371 covers or obstructs the opening 2351 (see FIGS. 6 and 7). In use, the bottom portion of the wall 2371 can be placed, after being removed from the first volume 2347, on a work surface 2410 within a sterile field 2412 such that the medicament delivery device 2100 (or any opening of the second tray member 2365) is exposed.

Either the first tray member 2340 or the second tray member 2365, or both (or any other tray members described herein) can be constructed from any suitable material. For example, in some embodiment, any of the first tray member 2340, the second tray member 2365, or any other tray member described herein can be constructed from a thin, medical grade material suitable for sterilization. Examples of materials include metal foils, ceramics, or polymers. The polymer may be biodegradable or non-biodegradable.

Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly (valeric acid), polyurethanes and copolymers and blends thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof. In some embodiments, either (or both) of the second tray 2365 and the first tray 2340 can be thermoformed, and can be constructed of styrene or LDPE.

As shown in FIGS. 5 and 6, the cover member 2390 (also referred to as a "lid" or "sterile barrier") is coupled to the first tray member 2340 about (or covering) the first volume 2347. The cover member 2390 is constructed from any suitable material formulated to resist and/or substantially prevent microbial penetration therethrough, and thus can maintain the sterility of the first volume 2347. For example, in some embodiments, the cover member 2390 (or any of the cover members described herein, including the cover members 1390, 3390) can be constructed from a porous polymer that is formulated to allow a sterilant gas or substance to pass therethrough, while substantially preventing pathogens or microbes from passing therethrough. In some embodiments, the cover member 2390 can be constructed from any one of polyethylene, high-density polyethylene (i.e., Tyvek®), polypropylene, polytetrafluoroethylene, or thermoplastic polyurethane. The packaging assembly 2300 (including the cover 2390), and any other packaging assemblies described herein, can be used with any suitable sterilization technique or medium, including ethylene oxide, gamma radiation, e-beam radiation, ultraviolet radiation, steam, plasma, or hydrogen peroxide.

The cover member 2390 can be coupled to the first tray member 2340 in any suitable manner to allow for removal from about the first volume 2347 during use (see, e.g., FIG. 6). For example, in some embodiments, the cover member 2390 can be coupled to the first tray member 2340 via a heat seal, an adhesive, a laser weld, or the like. In some embodiments the cover member 2390 (or any of the cover members described herein) can be flexible, and can be peeled from a flange of the first tray member 2340 when removed. In other embodiments, the cover member 2390 (or any of the cover members described herein) can include perforations (or stress concentration risers) to allow a portion of the cover member to be torn, separated and/or ruptured when removed from the first tray member 2340. In yet other embodiments, the cover member 2390 (or any of the cover members described herein) can be substantially rigid (see, e.g., the cover member 3390 described herein).

In use, the medicament delivery kit 2000 can be stored and shipped in its first configuration, as shown in FIG. 5. When in the first configuration, the second tray member 2365 is disposed within the first volume 2347 and the cover member 2390 is coupled about the opening 2351. In this manner, the first volume 2347 can be maintained as a sterile environment within which the medicament delivery device 2100 and any other accessories are stored. To prepare the medicament delivery device 2100 for use, the packaging assembly 2300 is first opened (i.e., it is placed in its second configuration). The packaging assembly 2300 is opened by removing the cover member 2390, as shown by the arrow EE in FIG. 6. The cover member 2390 can be removed, for example, by peeling an edge of the cover member 2390 from the first tray member 2340, or any other method as described herein. When the packaging assembly 2300 is in the second configuration (i.e., with the cover member 2390 removed), the medicament delivery device 2100 and/or the second volume 2370 defined by the second tray member 2365 remain enclosed and/or surrounded by the wall 2348 and the wall 2371. In this manner, even though the microbial barrier of the cover member 2390 has been removed, the integrity of the sterile first volume 2347 can be protected and/or maintained.

The first tray member 2340 (and the contents therein) is then oriented such that the opening 2351 that provides access to the first volume 2347 is facing downward towards a work surface 2410 within a sterile field 2412. Similarly stated, the packaging assembly 2300 can be placed in its third configuration by flipping the first tray member 2340 "upside down" so that the opening 2351 is facing downward. When the first tray member 2340 (and the contents therein) is oriented as shown in FIG. 7, the packaging assembly 2300 (including the first tray member 2340 and the second tray member 2365) is maintained apart from the work surface 2410. In this manner, the non-sterile, outer portions of the first tray member 2340 do not contact the sterile surface 2410, thereby maintaining the integrity of the sterile field 2412 established for the procedure.

In some embodiments, the first tray member 2340 and/or the second tray member 2365 (or any other tray members described herein) can include a lock, retainer, or other suitable feature to maintain the second tray member 2365 within the first volume 2347 when the first tray member 2340 is oriented with the opening 2351 facing downward. Similarly stated, in some embodiments, the first tray member 2340 and/or the second tray member 2365 (or any other tray members described herein) can be configured to retain the second tray member 2365 within the first tray member 2340 to keep the second tray member 2365 from falling out of the first tray member 2340 when the first tray member is inverted as shown in FIG. 7. For example, in some embodiments, the first tray member 2340 can include a locking portion (not shown, e.g., a recess, a protrusion, or the like) configured to matingly engage a flange or protrusion (not shown) of the second tray member 2365 to couple the second tray member 2365 within the first volume 2351. In other embodiments, the second tray member 2365 can includes a locking portion (not shown, e.g., a recess, a protrusion, or the like) configured to matingly engage a flange or protrusion (not shown) of the first tray member 2340 to couple the second tray member 2365 within the first volume 2351.

Referring to FIG. 8, the second (or inner) tray member 2365 is then released from within the first volume 2347 to place the second tray member 2365 on the work surface 2410 within the sterile field 2412. Because the packaging assembly 2300 is oriented with the opening 2351 facing downward, the second tray member 2365 is dropped onto the work surface 2410 (as shown by the arrow FF) by gravity. This arrangement allows the second tray member 2365 and the medicament delivery device 2100 to be placed within the sterile field 2412 without being directly touched or manipulated by the user. In some embodiments, for example, the first tray member 2340 (or any of the tray members described herein) can include an actuation portion (not shown in FIG. 8) that can be manipulated by the user to cause the second tray member 2365 to be released from within the first volume 2351. For example, in some embodiments, the user can apply an actuation force to the first tray member 2340 thereby deforming a portion of the first tray member 2340 and/or the second tray member 2365 to release the second tray member 2365 without the user directly touching the second tray member 2365. In this manner, the packaging assembly 2300 can maintain the integrity of the sterile field 2412 by limiting (or eliminating) direct contact between the user and the second tray member 2365.

Although the medicament delivery kit 2000 is shown and described above as including the medicament delivery device 2100 within the second volume 2370 of the second (or inner) tray member 2365, in other embodiments, a medicament delivery kit can include portions of a medicament delivery device in one tray member (e.g., an inner tray) and other portions of the medicament delivery device in another tray member (e.g., an outer tray). In other embodiments, a medicament delivery kit can include a medicament delivery device in one tray member (e.g., an inner tray) and other accessories associated with the procedure or the medicament delivery device in another tray member (e.g., an outer tray). For example, in some embodiments, a medicament delivery kit can include non-sterile (or separately sterilized) accessories in a separate tray (or a separate volume) from that within which the medicament delivery device is contained. For example, in some embodiments a medicament delivery kit (including any of the kits described herein) can include prepackaged alcohol wipes, gloves, or anatomical markers. Such accessories can be contained in a separate location from that within which the medicament delivery device is contained. Such an arrangement allows the medicament delivery device to be assembled into the kit and sterilized in a distinct operation from the inclusion of such accessories in the kit. Thus, the such kits increase the flexibility of manufacturing and assembly by allowing the accessories to be added to the kit in a non-sterile environment and/or in a different step.

In some embodiments, for example, any of the medicament delivery kits described herein can include a medicament container (e.g., a vial, an ampoule, a cartridge, or the like) that contains a dose of medicament, and that is stored in a volume that is separate from the volume within which the medicament delivery device is stored. In this manner, the medicament delivery device can be assembled, packaged and/or sterilized in one operation, and the medicament container can be added in a second, different operation. Because the medicament delivery kits described herein facilitate the maintenance of a sterile field, in use the medicament delivery device and the medicament container can be unpackaged and readied for use in a convenient manner within a sterile field. This arrangement can allow different drugs and/or dosage levels to be efficiently packaged in the same kit design. For example, in such embodiments, the medicament delivery device for multiple different drug products can be the same, and can be assembled, packaged, and/or sterilized in a first operation. The kit can the proceed to a second, different assembly operation in which the medicament container specific to the drug product is packaged within the kit. For example, in some embodiments, the kit can be assembled with either a standard dose (e.g., an adult dose) or a smaller dose (e.g., a pediatric dose). In other embodiments, the kit can be assembled with different drug formulations. Indicia, labels and/or other instructions, such as those described below with reference to the kit 1000 can be used to easily identify the drug product.

As one example, FIGS. 9-12 are schematic illustrations of a medicament delivery kit 3000 (also referred to as a "kit" or a medicament delivery system), according to an embodiment. FIGS. 9-12 show the kit 3000 in a first configuration, a second configuration, a third configuration, and a fourth configuration, respectively. The kit 3000 includes a packaging assembly 3300 that contains a medicament delivery device 3100 (see FIGS. 11 and 12) and a medicament container 3200. The medicament delivery device 3100 can be any suitable device (or collection of components) for delivering a medicament via any suitable method. For example, in some embodiments, the medicament delivery device 3100 can be an ocular injector of the types shown and described herein and in International Patent Application No. WO2015/19584, entitled "METHODS AND DEVICES FOR TREATING POSTERIOR OCULAR DISORDERS" and U.S. Pat. No. 9,180,047, entitled "APPARATUS AND METHODS FOR OCULAR INJECTION," each of which is incorporated herein by reference in its entirety. Although the medicament delivery device 3100 is shown schematically in FIG. 8 as including multiple components that are stored separately within the packaging assembly 3300, in other embodiments, the medicament delivery device 3100 (or any other medicament delivery device described herein) can be a single, pre-assembled device (e.g., a prefilled syringe). Such a pre-assembled device can include a dose of any suitable medicament of the types shown and described herein. Moreover, the medicament delivery device 3100 can be any suitable device or drug product, such as a syringe (i.e., a manually-actuated injector), an auto-injector, a nasal delivery device, an inhaler, a nebulizer, or any other suitable device.

The medicament container 3200 (FIGS. 9 and 10) can be any suitable container that contains (or is at least partially filled) with any of the medicaments described herein. For example, the medicament container 3200 (and any of the containers shown herein, including the container 1200) can be a vial, ampoule, cartridge, or other suitable container that contains the medicament to be delivered via the medicament delivery device 3100. In other embodiments, the medicament container 3200 (and any of the containers shown herein, including the container 1200) can be a prefilled syringe that contains the medicament to be delivered via the medicament delivery device 3100. In such embodiments, the prefilled syringe can be used, for example, to mix (or reconstitute) a portion of the medicament, convey the medicament into the medicament delivery device 3100 for subsequent delivery, or the like. In yet other embodiments, the medicament container 3200 can be a pouch, blister pack, or other container that includes the medicament. The medicament within the medicament container 3200 can be in any suitable form, including a liquid or powder (e.g., lyophilized) form. The medicament within the container 3200 (or any of the containers described herein, including the medicament container 1200) can have any suitable formulation, including any of the formulations described herein. For example, in some embodiments, the medicament container 3200 can include triamcinolone or triamcinolone acetonide. In other embodiments, the medicament container 3200 can contain triamcinolone or triamcinolone acetonide.

Figure 9:
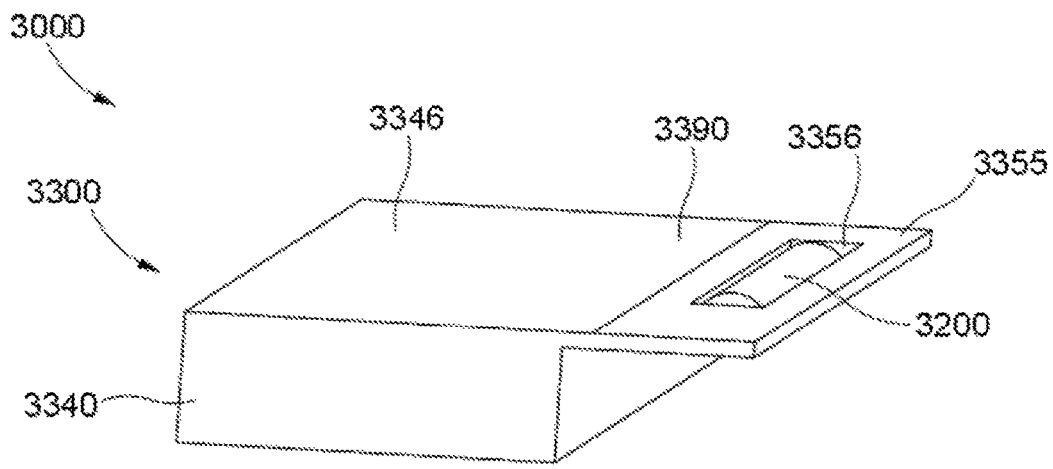
FIGS. 9-12 are schematic illustrations of a kit according to an embodiment, in a first configuration, second configuration, third configuration, and fourth configuration, respectively.

The packaging assembly 3300 includes a first (or outer) tray member 3340, a second (or inner) tray member 3365 (see FIGS. 7 and 8), and a cover member (also referred to a lid) 3390. The first tray member 3340 includes a first portion 3346 and a second portion 3355. The first portion 3346, which is also described as the sterile portion, defines a first volume 3347 and an opening that provides access to the first volume 3347. As described below, the second tray member 3365 is received within the first volume 3347. The second portion 3355, which is also described as the non-sterile portion, defines a container volume 3356 and an opening that provides access to the container volume 3356. As shown in FIG. 9, the container volume 3356 is configured to receive the medicament container 3200. The second portion 3355 can include any suitable retainer or lock portion (not shown) that maintains the medicament container 3200 within the container volume 3356. For example, in some embodiments, the second portion 3355 can include a series of retention protrusions within the container volume 3356 that correspond to portions of the medicament container 3200. In this manner, the medicament container 3200 can be fixedly, but removably retained within the container volume 3356 when the kit 3000 is in its first configuration, as shown in FIG. 9. Specifically, such ribs, protrusions, or the like can produce an interference fit with the medicament container 3200, and to keep the container 3200 from inadvertently slipping out of the container volume 3356.

The first tray member 3340 can be of any suitable shape or size. For example, although shown as being substantially rectangular, in other embodiments, the first tray member 3340 (and any of the tray members described herein) can have a circular cross-sectional shape, an oval cross-sectional shape, or a polygonal cross-sectional shape (e.g. five-sided, six-sided, or the like). Moreover, although the first tray member 3340 is shown as having a substantially constant cross-sectional size (i.e., the cross-sectional size along the axis of height is non-tapered), in other embodiments, the shape of the first tray member 3340 (or any other tray members described herein) can be variable over the height of the tray member, or can otherwise be irregular.

Figure 11:
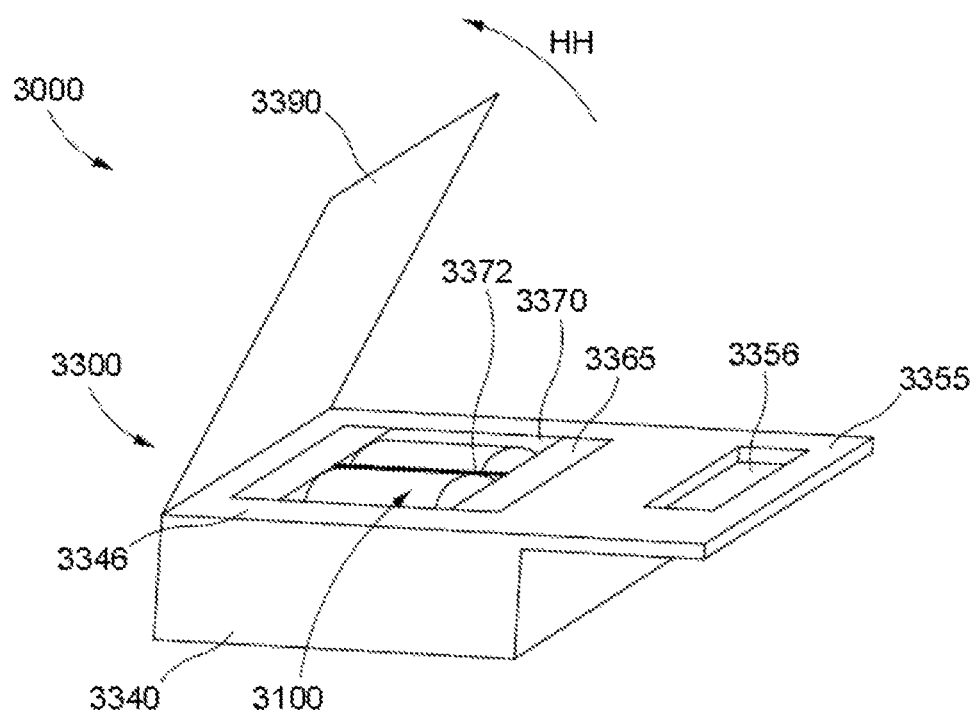
Figure 12:
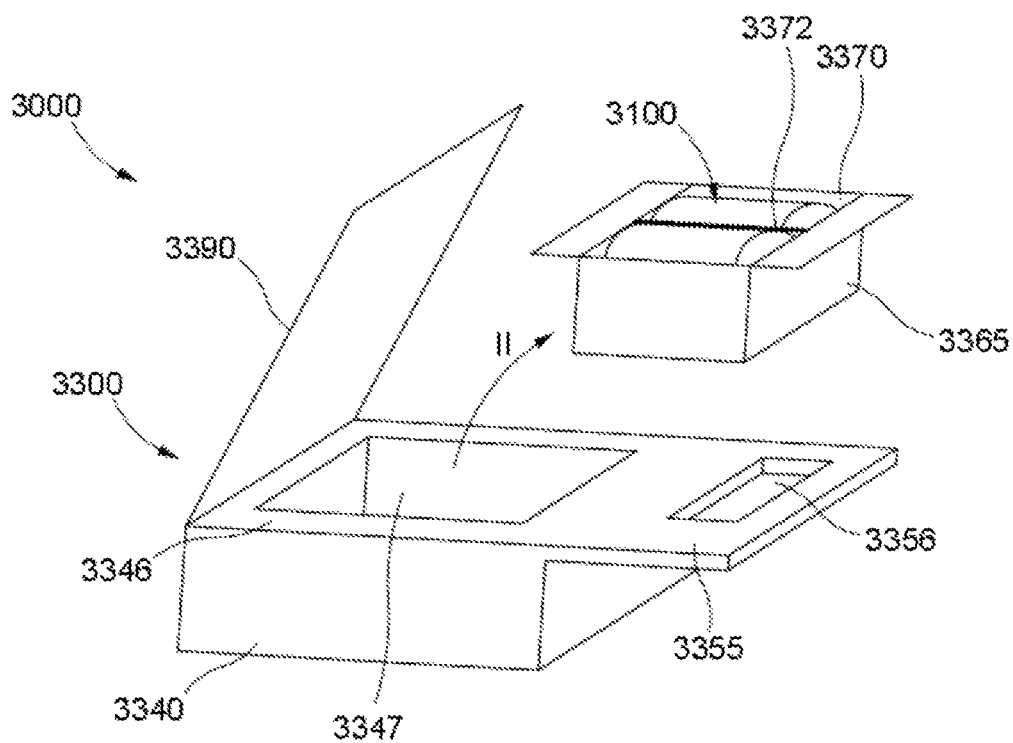

Referring to FIGS. 11 and 12, the second tray member 3365 defines a second volume 3370 that is of any suitable shape and/or size to contain or receive at least a portion of the medicament delivery device 3100. For example, as shown, the second volume 3370 can be a continuous volume within which the portion of the medicament delivery device 3100 is contained. In other embodiments, the second volume 3370 can be a series of disconnected (or non-contiguous) volumes defined by a wall of the second tray member 3365, within which different portions of the medicament delivery device 3100 are contained. For example, in some embodiments, the second volume 3370 (or any of the second volumes described herein) can include a first "cut-out" or volume that receives a barrel of a medical injector, a second distinct "cut-out" or volume that receives a needle of the medical injector, and a third distinct "cut-out" or volume that receives yet another portion of the medical injector. Additionally, the second tray member 3365 includes a retainer 3372 that retains, contains and/or holds at least a portion of the medicament deliver device 3100 within the second volume 3370. For example, in some embodiments, the retainer 3372 can be a portion of a wall of the second tray member 3365 that defines an opening within which the portion of the medicament delivery device 3100 is press fit. In other embodiments, the retainer 3372 can include a band, a rotatable arm or other movable member that engages and/or contacts the portion of the medicament delivery device 3100 to retain the device 3100 within the second volume 3370.

The second tray member 3365 is configured to be disposed within first volume 3347 such that, when the medicament delivery kit is in its first configuration (see FIG. 9), the medicament delivery device 3100 is enclosed the within the first volume 3347. Similarly stated, the when the medicament delivery kit 3000 is assembled (i.e., in its first configuration, as shown in FIG. 9), the first tray member 3340 and the second tray member 3365 surround the medicament delivery device 3100. In this manner, after the first volume is sterilized (e.g., during assembly of the kit 3000), the medicament delivery device 3100 is maintained within the sterile first volume 3347.

Although the second tray member 3365 is shown as being disposed within the first volume 3347 in an upright position (i.e., with the opening providing access to the second volume 3370 facing upward), in other embodiments, the second tray member 3365 can be disposed within the first volume 3347 in any suitable orientation. For example, in some embodiments, the second tray member 3365 can be positioned within the first tray member 3340 such that the opening of the first tray member 3340 is obstructed by a bottom wall of the second tray member 3365, as described herein with reference to the kit 1000 and the kit 2000. In some embodiments, the second tray member 3365 can be positioned within the first tray member 3340 such that the opening of the second tray member 3365 is obstructed by a bottom wall of the first tray member 3340, as described herein with reference to the kit 1000 and the kit 2000.

Either the first tray member 3340 or the second tray member 3365, or both (or any other tray members described herein) can be constructed from any suitable material. For example, in some embodiment, any of the first tray member 3340, the second tray member 3365, or any other tray member described herein can be constructed from a thin, medical grade medical grade material suitable for sterilization. Examples of materials include metal foils, ceramics, or polymers. The polymer may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly (butyric acid), poly(valeric acid), polyurethanes and copolymers and blends thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof. In some embodiments, either (or both) of the second tray 3365 and the first tray 3340 can be thermoformed, and can be constructed of styrene or LDPE.

Figure 10:
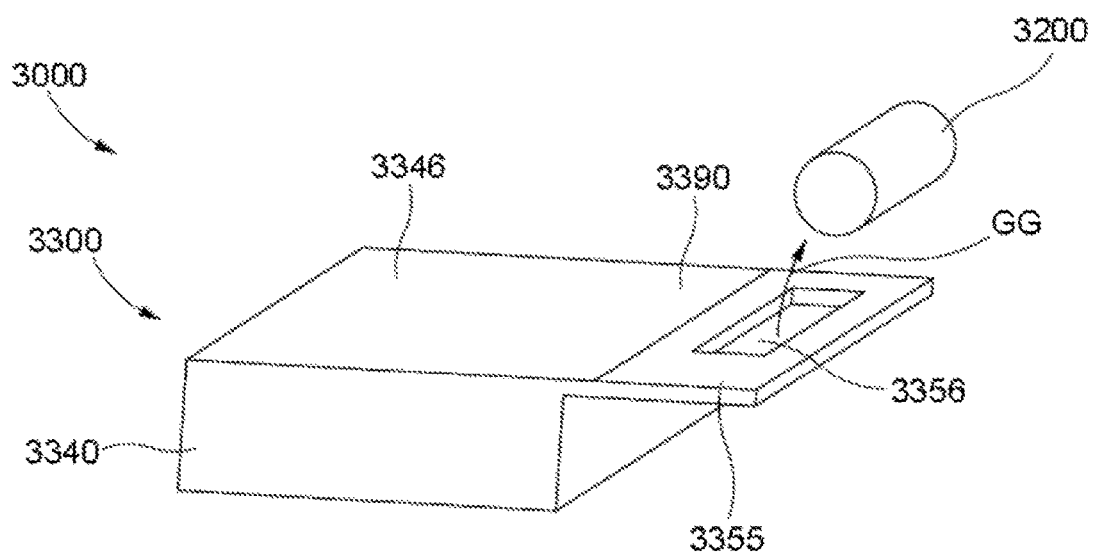

As shown in FIGS. 9 and 10, the cover member 3390 (also referred to as a "lid" or "sterile barrier") is coupled to the first tray member 3340 about (or covering) the first volume 3347. When the kit 3000 is in its first (FIG. 9) or second (FIG. 10) configuration, however, the container volume 3356 is exposed. Similarly stated, when the cover member 3390 is coupled to the first tray member 3340 about the first volume 3347 the container volume 3356 remains exposed and/or accessible. Thus, the first volume 3347 can be maintained as a sterile environment (within which the medicament delivery device 3100 is contained), while the container volume can be maintained in a non-sterile environment. In this manner, as described herein, the medicament delivery device 3100 can be assembled, packaged, and sterilized in a separate operation from the assembly or inclusion of the medicament container within the kit 3000.

The cover member 3390 is constructed from any suitable material formulated to resist and/or substantially prevent microbial penetration therethrough, and thus can maintain the sterility of the first volume 3347. For example, in some embodiments, the cover member 3390 (or any of the cover members described herein, including the cover members 1390, 3390) can be constructed from a porous polymer that is formulated to allow a sterilant gas or substance to pass therethrough, while substantially preventing pathogens or microbes from passing therethrough. In some embodiments, the cover member 3390 can be constructed from any one of polyethylene, high-density polyethylene (i.e., Tyvek®), polypropylene, polytetrafluoroethylene, or thermoplastic polyurethane. The packaging assembly 3300 (including the cover 3390), and any other packaging assemblies described herein, can be used with any suitable sterilization technique or medium, including ethylene oxide, gamma radiation, e-beam radiation, ultraviolet radiation, steam, plasma, or hydrogen peroxide.

The cover member 3390 can be coupled to the first tray member 3340 in any suitable manner to allow for removal from about the first volume 3347 during use (see, e.g., FIG. 11). For example, in some embodiments, the cover member 3390 can be coupled to the first tray member 3340 via a heat seal, an adhesive, a laser weld, or the like. Although the cover member 3390 is shown as being substantially rigid, in other embodiments the cover member 3390 (or any of the cover members described herein) can be flexible, and can be peeled from a flange of the first tray member 3340 when removed. In yet other embodiments, the cover member 3390 (or any of the cover members described herein) can include perforations (or stress concentration risers) to allow a portion of the cover member to be torn, separated and/or ruptured when removed from the first tray member 3340.

In use, the medicament delivery kit 3000 can be stored and shipped in its first configuration, as shown in FIG. 9. When in the first configuration, the second tray member 3365 is disposed within the first volume 3347 and the cover member 3390 is coupled about the first volume 3347. As described above, the container volume 3356 is accessible. In this manner, the first volume 3347 can be maintained as a sterile environment within which the medicament delivery device 3100 and any other accessories are stored, while the container need not be maintained in the sterile environment. To prepare the medicament delivery device 3100 for use, the medicament container 3200 is removed from the container volume 3356 as shown by the arrow GG in FIG. 10, thereby placing the kit 3000 in its second configuration. Although shown as being the first operation in preparing the drug product for use, in other embodiments, the medicament container 3200 can be removed after the medicament delivery device 3100 and/or the second tray member 3365 are removed.

The packaging assembly 3300 is opened (i.e., it is placed in its third configuration). The packaging assembly 3300 is opened by removing the cover member 3390 from about the first volume 3347, as shown by the arrow HH in FIG. 11. The cover member 3390 can be removed, for example, by lifting up (or peeling) an edge of the cover member 3390 from the first tray member 3340, or any other method as described herein. When the packaging assembly 3300 is in the third configuration (i.e., with the cover member 3390 removed and/or the first volume 3347 exposed), the second tray member 3365 can be released (or removed) from within the first volume 3347, as shown by the arrow II, and placed on the desired work surface (not shown). For example, as described herein, the second tray member 3365 can be placed on a surface within a sterile field, within which the medicament delivery device 3100 and the medicament container 3200 can be manipulated to prepare the drug product for use. For example, in some embodiments, a dose of medicament from within the medicament container can be withdrawn and/or conveyed into a reservoir of the medicament delivery device 3100. In other embodiments, a needle, mouthpiece, or other delivery member can be coupled to the medicament delivery device 3100 to prepare the device for drug delivery.

The packaging assembly 3300 facilitates such preparation within the sterile field. For example, the retainer 3372 to maintains the medicament delivery device 3100 within the second volume 3370 when the second tray member 3365 is being moved. Similarly stated, the second tray member 3365 and the retainer 3372 can limit movement of the medicament delivery device 3100 relative to the second tray member 3365 until the user is prepared to use the device (e.g., the packaging assembly prevents the medicament delivery device 3100 from rolling out of the sterile field). Similarly, the raised wall(s) of the second tray member 3265 (and the other tray members described herein, such as the tray member 1365, 2365) provide an obstruction that facilitates maintaining the integrity of the sterile field.

Although the second tray member 3265 is shown as being removed from the first volume 3247 while being "right-side up," in other embodiments, the second tray member 3265 can be oriented such that the opening of the first tray member is oriented downward.

In some embodiments, the first tray member 3340 and/or the second tray member 3365 (or any other tray members described herein) can include a lock, retainer, or other suitable feature to maintain the second tray member 3365 within the first volume 3347. Similarly stated, in some embodiments, the first tray member 3340 and/or the second tray member 3365 (or any other tray members described herein) can be configured to retain the the second tray member 3365 within the first tray member 3340 to keep the second tray member 3365 from inadvertently falling out of the first tray member 3340 after the cover member 3390 is removed. For example, in some embodiments, the first tray member 3340 can include a locking portion (not shown, e.g., a recess, a protrusion, or the like) configured to matingly engage a flange or protrusion (not shown) of the second tray member 3365 to couple the second tray member 3365 within the first volume 3351. In other embodiments, the second tray member 3365 can includes a locking portion (not shown, e.g., a recess, a protrusion, or the like) configured to matingly engage a flange or protrusion (not shown) of the first tray member 3340 to couple the second tray member 3365 within the first volume 3351.

Although the kit 2000 and the kit 3000 are shown and described as include any suitable type of medicament delivery device, in some embodiments, any of the kits described herein can include a medical injector. In some embodiments, for example, a kit for ocular injection can include a medicament container (or vial) containing the drug for injection, an injection assembly, and the packaging (and additional components) to facilitate the desired injection processes, as described herein and in International Patent Application No. WO2015/19584, entitled "METHODS AND DEVICES FOR TREATING POSTERIOR OCULAR DISORDERS" and U.S. Pat. No. 9,180,047, entitled "APPARATUS AND METHODS FOR OCULAR INJECTION," each of which is incorporated herein by reference in its entirety. For example, FIGS. 13-49 show various views of a medicament delivery kit 1000 (also referred to as a medicament delivery system, or simply a kit)) according to an embodiment. The kit 1000 includes an injector assembly 1100 (see e.g., FIGS. 17, 18, 24, and 25), a set of needle assemblies 1160A and 1160B (see e.g., FIGS. 17 and 18), a medicament container 1200 (see e.g., FIGS. 16 and 36), a container adapter 1220 (also referred to as a vial adapter, see e.g., FIGS. 19-23), and a packing assembly 1300 (see e.g., FIGS. 13-17).

Figure 13:
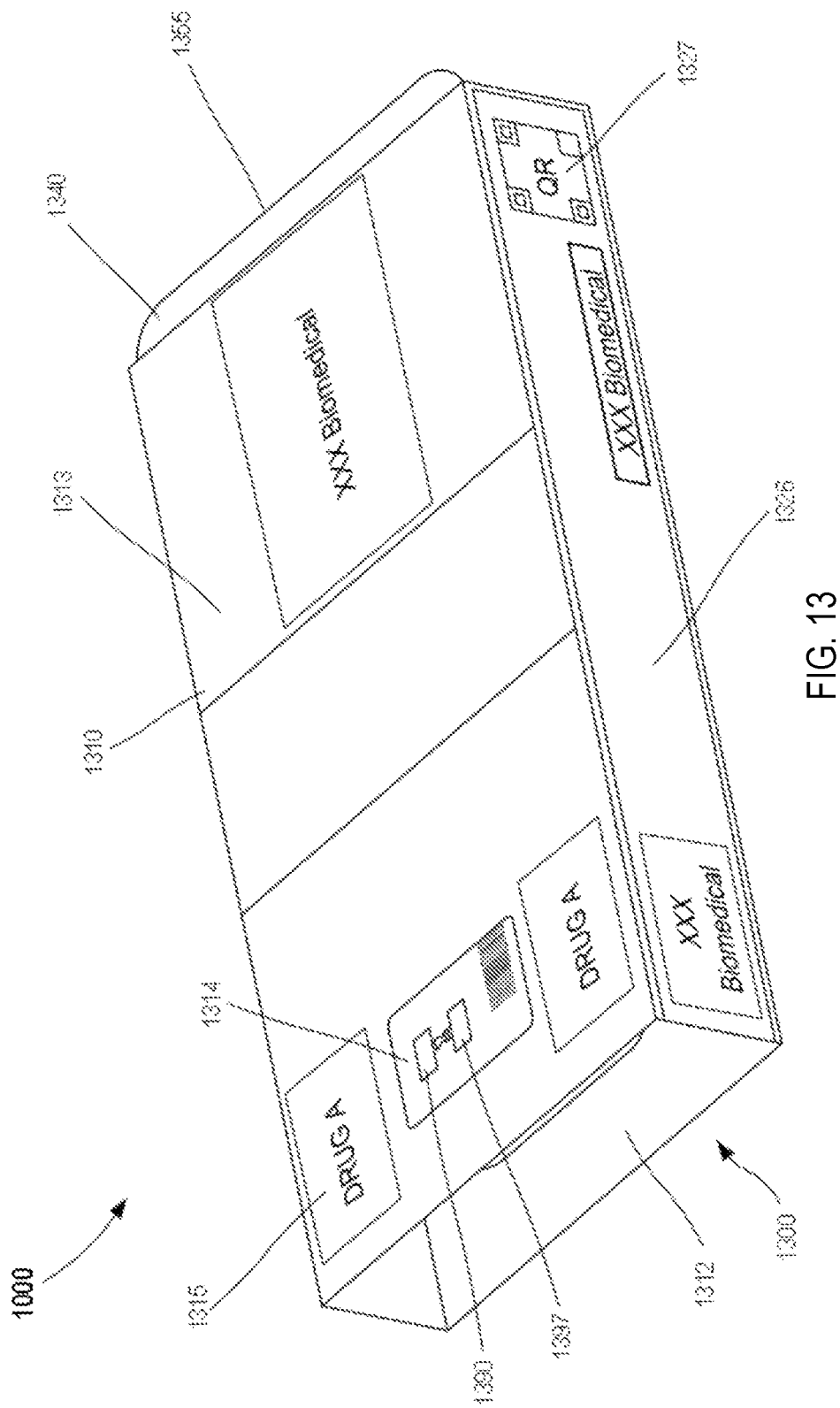
FIGS. 13 and 14 are a top perspective view and a bottom perspective view, respectively, of a kit according to an embodiment.

As shown in FIGS. 13-17, the packaging assembly 1300 includes a sleeve 1310, a first (or outer) tray 1340, a second (or inner) tray 1365, and a lid (or cover) 1390. The assembly of the first tray 1340, the second tray 1390 and the components therein are referred to herein as the tray assembly 1301. The sleeve 1310 defines a volume 1312 within which at least a portion of the tray assembly 1301 is disposed when the kit 1000 is in a first (or storage) configuration, as shown in FIG. 13. The sleeve 1310 defines a first (or front) outer surface 1313, a second (or back) outer surface 1320, a third (or side) outer surface 1325, and a fourth (or side) outer surface 1326. The front outer surface 1313 defines an opening 1314 through which an indicium 1397 (e.g., a printed instruction, a machine-readable indicator, a characteristic color, or the like) on the cover 1390 can be viewed when the kit is in the first configuration. In this manner, information specific to the tray assembly 1301 that is conveyed by the indicium 1397 can be viewed by a user (either visually or via a scanner) without the need to remove the tray assembly 1301 from within the sleeve 1310. Such information can include, for example, the lot number associated with the kit 1000, the range of needle sizes included with the injector assembly 1100, manufacturing information associated with the injector assembly 1100, identification of the drug and dosage, expiration dates, and the like. In some embodiments, the opening 1314 can be a through-opening, while in other embodiments, the opening 1314 can be covered with a transparent covering that allows the indicia 1397 to be viewed.

The front outer surface 1313 also includes indicia 1315. The indicia 1315 can be any suitable markings, indicators, or machine-readable code associated with the kit 1000, the therapeutic regimen or the like. For example, the indicia 1315 can specify or correspond to the different dose of the therapeutic regimen (e.g., adult dose, pediatric dose or the like). The indicia 1315 can include instructions, such as, for example, drug labeling, warnings, or the like. The indicia 1315 can be text, figures, a machine-readable code, or any other suitable format to convey information to a user (either manually or via a computer-assisted reader).

Figure 14:
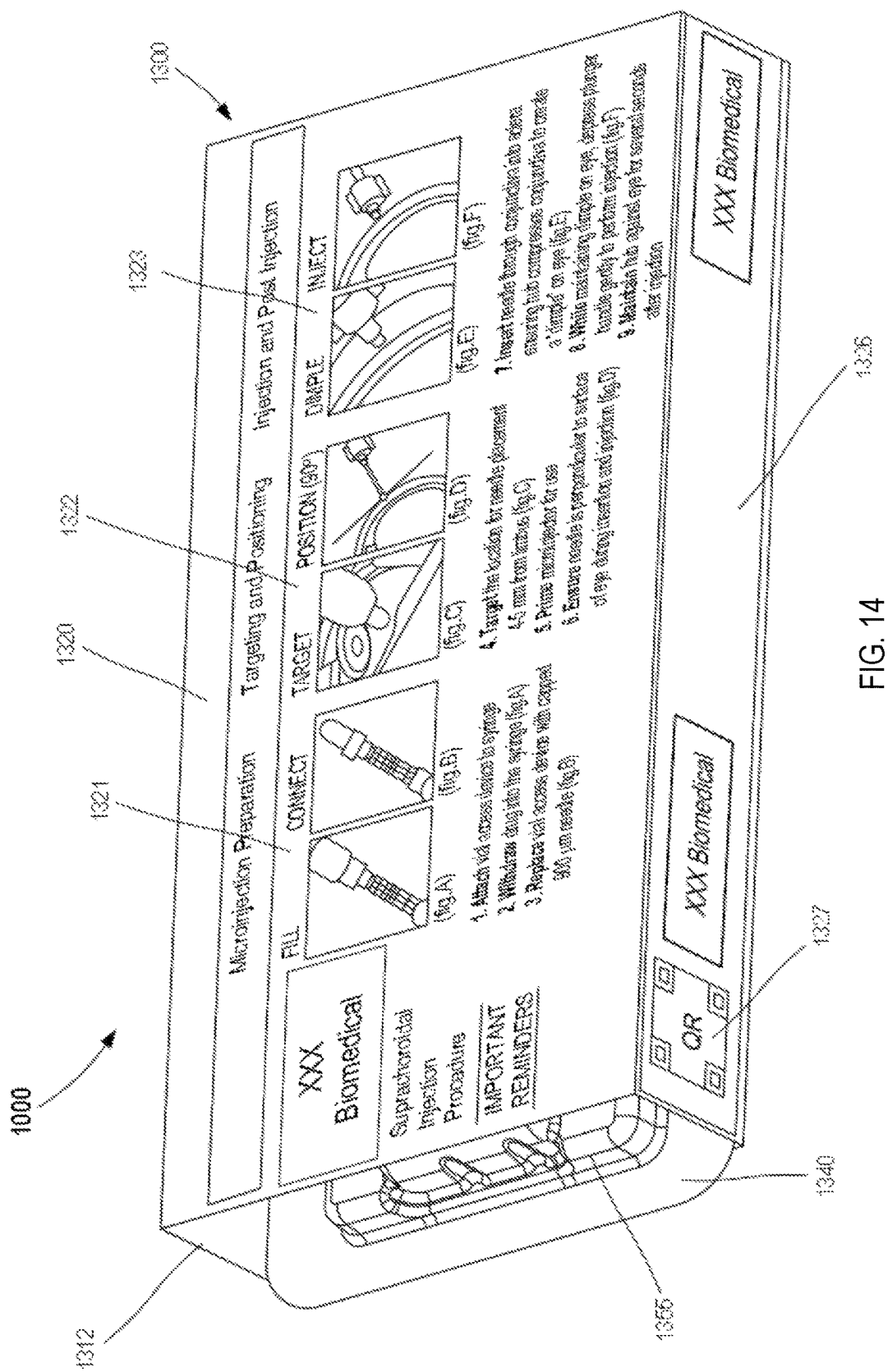

As shown in FIG. 14, the back outer surface 1320 includes a series of instruction indicia. More specifically, the back outer surface 1320 includes a first instruction indicium 1321, a second instruction indicium 1322, and a third instruction indicium 1323. The instruction indicia can include instructions, pictures, text or the like to provide information to the user in connection with the use of the kit. In some embodiments, the back outer surface 1320 (or any other portion of the sleeve 1310) can include instructions related to the opening and/or unwrapping of the kit 1000, instructions associated with the maintenance of a sterile field or the like. The instruction indicia can be text, figures, a machine-readable code, or any other suitable format to convey information to a user (either manually or via a computer-assisted reader). As shown in FIG. 14, the side surface 1326 includes a machine-readable code 1327.

Although shown as being substantially rectangular, in other embodiments, the sleeve 1310 can be any suitable shape. For example, in some embodiments, a kit can include a cylindrical sleeve. Moreover, the sleeve 1310 can be constructed from any suitable material, such as, for example, a medical grade paper and/or cardboard that is resistant to bacteria, is "low particulate" in nature, or the like. For example, in some embodiments, the sleeve 1310 can include a coating (e.g., a wax coating, a bacteria-resistant coating, or the like).

As shown in FIGS. 15 and 16, and described in more detail below, the tray assembly 1301 (which includes the outer (or first) tray 1340, the inner (or second) tray 1365 and the cover 1390) is slidably disposed within the inner volume 1312 of the sleeve 1310. Accordingly, the sleeve 1310 can be sized to maintain the tray assembly 1301 therein. Similarly stated, the sleeve 1310 can be sized to exert a slight pressure (or friction force) upon the tray assembly 1301 to limit the likelihood of the tray assembly 1301 inadvertently slipping out of the sleeve 1310 during shipping. In some embodiments, the kit 1000 can include a wrap (e.g., a clear, plastic wrap) about the sleeve 1310 that maintains the kit 1000 in its first (or storage) configuration.

Figure 36:
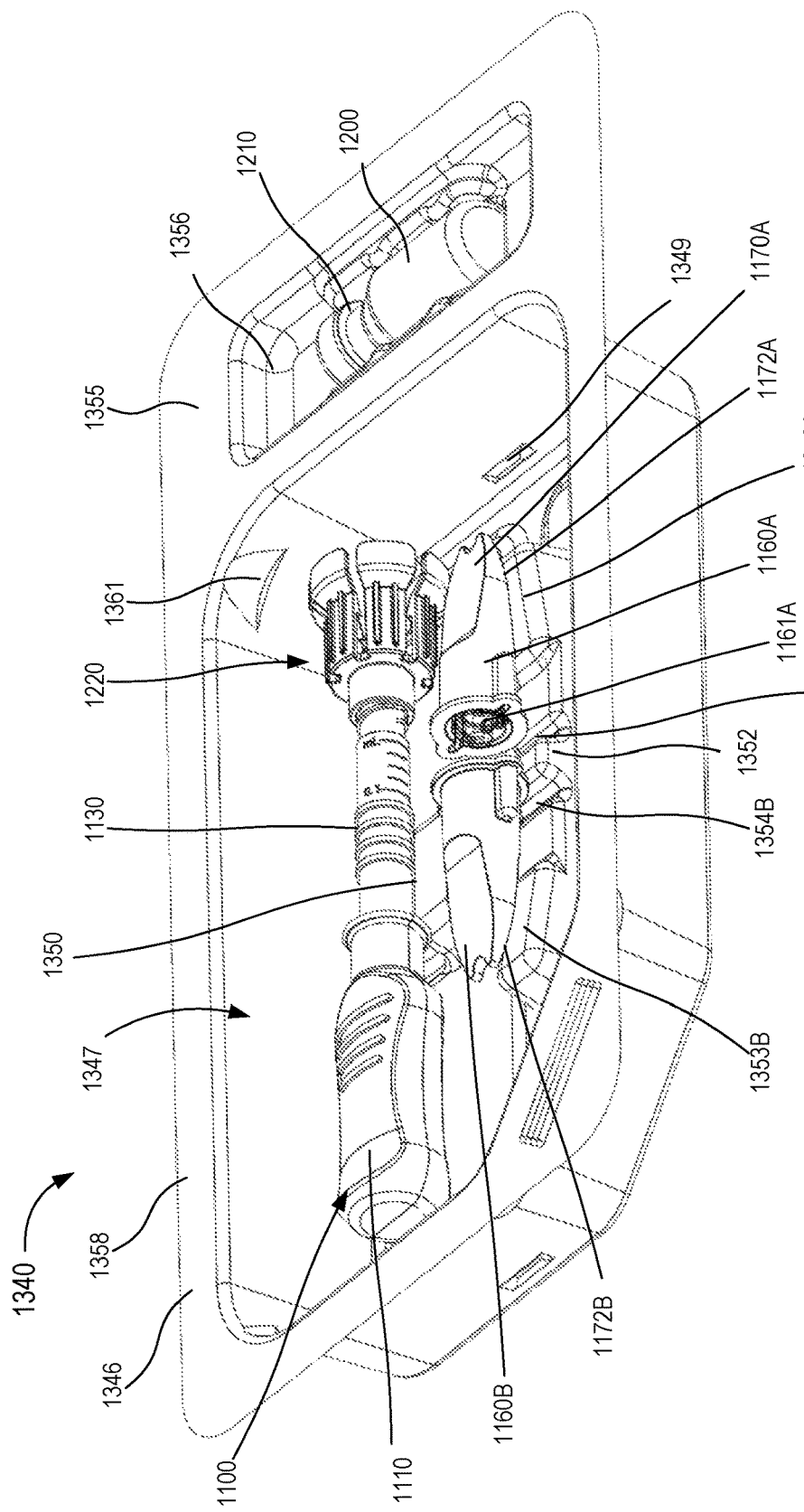
FIG. 36 is a perspective view of a portion of the kit shown in FIGS. 13 and 14, including the first tray member.
Figure 47:
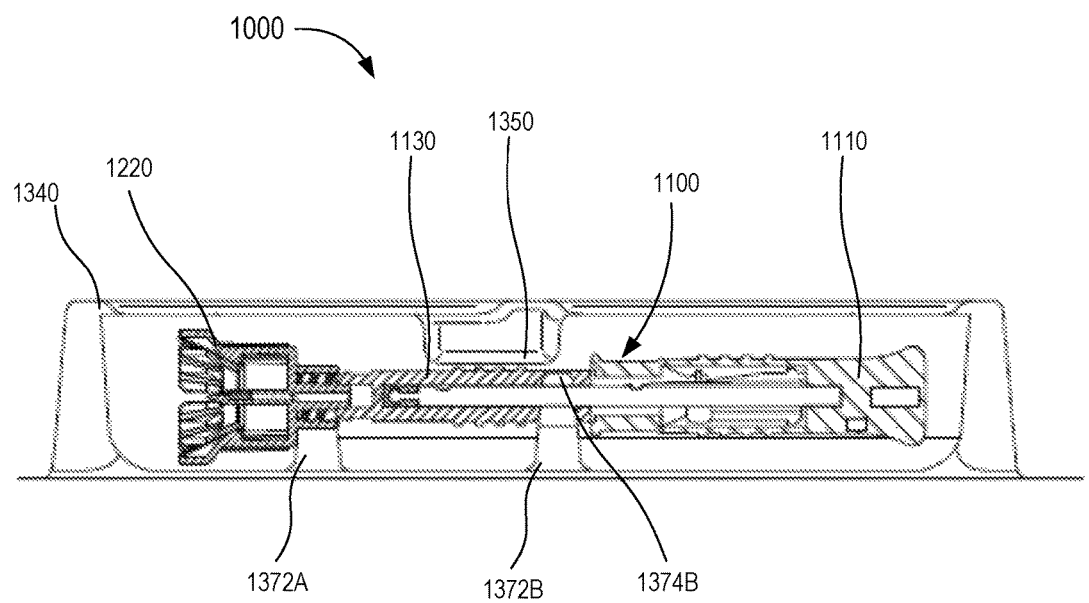

As shown in FIGS. 17, 26-28, the outer tray 1340 includes a first (or outer) side surface 1341 and a second (or inner) side surface 1342. The outer tray 1340 also includes a first (or sterile) portion 1346 and a second (or non-sterile) portion 1355. The first portion 1346 includes a side wall (also referred to as a wall or body) 1348, and defines a first volume 1347. The volume 1347 is defined on the second (or inner) side surface 1342, as shown. As described in more detail, the first volume is maintained as a sterile volume, and contains the second tray member 1365, the injector assembly 1100, and the two needle assemblies 1160A, 1160B when the kit 1000 is in its first (or storage) configuration. More specifically, the side wall 1348 includes an injector retention protrusion 1350, a needle retention portion 1352, and two locking protrusions 1349A, 1349B. As shown in FIGS. 36 and 47, the injector retention protrusion 1350 includes a surface against which a portion of the injector barrel 1130 can rest when the kit 1000 is in its first configuration. As shown in FIG. 47, the protrusion 1350, the first injector retention member 1372A (of the second tray 1360, described below), and the second injector retention member 1372B (of the second tray 1360) maintain the injector barrel 1130 and/or the injector 1100 in a fixed position within the volume 1347 when the kit 1000 is in its first configuration. Specifically, the injector barrel 1130 is disposed "horizontally" within the volume 1347. Similarly stated, a longitudinal axis of the injector barrel 1130 is substantially parallel to the bottom outer surface 1341 of the first tray 1340 and/or the bottom outer surface 1366 of the second tray 1365 when the kit 1000 is in its first configuration. In this configuration, the first injector retention member (or retainer) 1372A engages a first portion of the barrel 1130, the second injector retention member (or retainer) 1372B engages a second portion of the barrel 1130, and the protrusion 1350 contacts a third portion of the barrel 1130 that is between the first portion and the second portion. Because the protrusion 1350 exerts a compressive force (i.e., a downward force, as viewed in FIG. 47) on the barrel 1130, the spatial relationship between the first injector retainer 1372A, the second injector retainer 1372B, and the protrusion 1350 (i.e., being spaced apart along the longitudinal axis of the barrel 1130) maintains the injector 1100 in a stable, fixed position. Said another way, when the kit 1000 is in the first configuration, the protrusion 1350 exerts a compressive force on the barrel 1130 that urges the barrel 1130 into contact with the first injector retainer 1372A and the second injector retainer 1372B.

Figure 46:
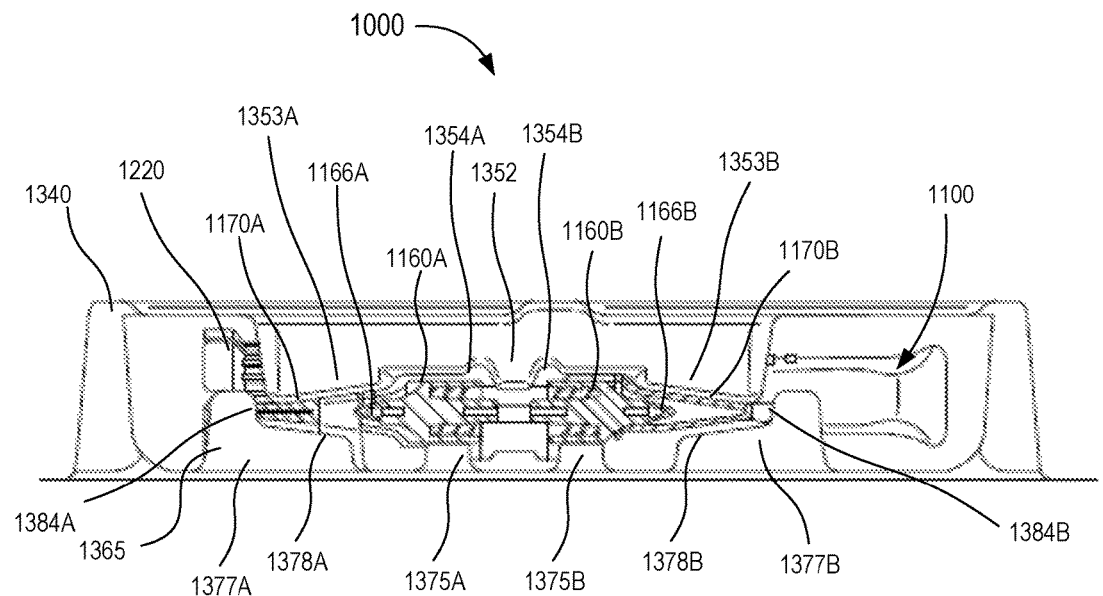
FIGS. 46 and 47 are cross-sectional views of the kit shown in FIGS. 13 and 14 taken along lines $X_1$-$X_1$ and $X_2$-$X_2$ in FIG. 45, respectively.

The needle retention portion 1352 includes a first tapered surface 1353A and defines a first recess 1354A. The needle retention portion 1352 also includes a second tapered surface 1353B and defines a second recess 1354B. The tapered surfaces 1353A, 1353B correspond to the tapered surface 1172 of the needle cap 1170, and the recesses 1354A, 1354B correspond to and/or receive a portion of the outer flange 1171 of the needle cap 1170. As shown in FIG. 46, the first tapered surface 1353A, the first recess 1354A, and the first needle retention portion 1376A (of the second tray 1360, described below) maintain the needle assembly 1160A in a fixed position within the volume 1347 when the kit 1000 is in its first configuration. Specifically, the first tapered surface 1353A exerts a compressive force (i.e., a downward force, as viewed in FIG. 46) on the needle assembly 1160A to maintain the needle assembly 1160A in a stable, fixed position. Said another way, when the kit 1000 is in the first configuration, the first tapered surface 1353A exerts a compressive force on the needle assembly 1160A that urges the needle assembly 1160A into contact with first needle retention portion 1376A. Similarly, the second tapered surface 1353B exerts a compressive force (i.e., a downward force, as viewed in FIG. 46) on the needle assembly 1160B to maintain the needle assembly 1160B in a stable, fixed position. Said another way, when the kit 1000 is in the first configuration, the second tapered surface 1353B exerts a compressive force on the needle assembly 1160B that urges the needle assembly 1160B into contact with second needle retention portion 1376B.

This structure enables the packaging assembly 1300 to maintain the injector assembly 1100 and the two needle assemblies 1160A, 1160B in a fixed position within the sterile first volume 1347 during storage and when the kit 1000 is being prepared for use. Specifically, the packaging assembly 1300 maintains the needle assemblies 1160A, 1160B in their respective positions spaced part from (i.e., not connected to) the injector assembly 1100.

The locking protrusions 1349A, 1349B are located towards the bottom of the first volume 1347, and engage a portion of the flange 1380 of the inner (or second) tray 1365 to retain or lock the inner tray 1365 within the outer tray 1340. As described in more detail below, the locking protrusions 1349A, 1349B are configured to releasably retain the flange 1380 such that when a force is exerted against outer surface 1341 of the outer tray 1340, a portion of the side wall 1348, the locking protrusions 1349A, 1349B, and/or the flange 1380 deform to release the flange 1380. The side wall 1348 also includes four shoulder surfaces 1361 located towards the top of the first volume 1347. The shoulder surfaces 1361 facilitate shipping and/or stacking of multiple outer trays.

The second (or non-sterile) portion 1355 includes a side wall (also referred to as a wall or body) 1357, and defines a second (also referred to as a container) volume 1356. As described in more detail, the container volume 1356 can be maintained as a non-sterile volume, and contains the medicament container (or vial) 1200. More specifically, the side wall 1357 includes a series of retention protrusions that correspond to portions of the medicament container 1200, such as for example, the sides or the neck 1210. In this manner, the medicament container 1200 can be fixedly retained within the second volume 1356 when the kit 1000 is in its first configuration. The side wall 1357 can include ribs, protrusions, or the like to produce an interference fit with the medicament container 1200, and to keep the container 1200 from inadvertently slipping out of the outer tray 1340.

The outer tray 1340 includes a flange 1358 that surrounds the first portion 1346 and the second portion 1355. The flange 1358 includes a corner portion having a series of peel protrusions 1359. As shown in FIG. 16, the cover 1390 is coupled to the outer tray 1340 such that a peel portion 1399 of the cover 1390 is coupled about the peel protrusions 1359.

The peel protrusions 1359 produce a region of discontinuity to assist the user in peeling the protective cover 1390 from about the first volume 1347.

The cover 1390 is constructed from any suitable material formulated to resist and/or substantially prevent microbial penetration therethrough, and thus can maintain the sterility of the volume about which the cover 1390 is disposed (e.g., the first volume 1347). For example, in some embodiments, the cover 1390 can be constructed from a porous polymer that is formulated to allow a sterilant gas or substance to pass therethrough, while substantially preventing pathogens or microbes from passing therethrough. In some embodiments, the cover 1390 can be constructed from any one of polyethylene, high-density polyethylene (i.e., Tyvek®), polypropylene, polytetrafluoroethylene, or thermoplastic polyurethane. The packaging assembly 1300 (including the cover 1390) can be used with any suitable sterilization technique or medium, including ethylene oxide, gamma radiation, e-beam radiation, ultraviolet radiation, steam, plasma, or hydrogen peroxide.

More specifically, as shown in FIG. 16, the cover 1390 is disposed about the first volume 1347, but does not cover the second volume 1356 (or the second portion 1355). In this manner, the tray assembly, and more specifically the outer tray 1340, includes a sterile portion (e.g., the first portion 1346) and a non-sterile portion (e.g., the second portion 1355). This arrangement allows the injector assembly 1100 and the needle assemblies 1160A, 1160B to be assembled into the kit 1000 and sterilized in a distinct manufacturing operation from the inclusion of the vial 1200 in the kit 1000. Thus, the kit 1000 increases the flexibility of manufacturing and assembly by allowing the vial 1200 to be added to the kit in a non-sterile environment and/or in a different step. Moreover, as described in more detail below, the dual-tray nature of the kit 1000 maintains the integrity of the sterile field during use.

Figure 37:
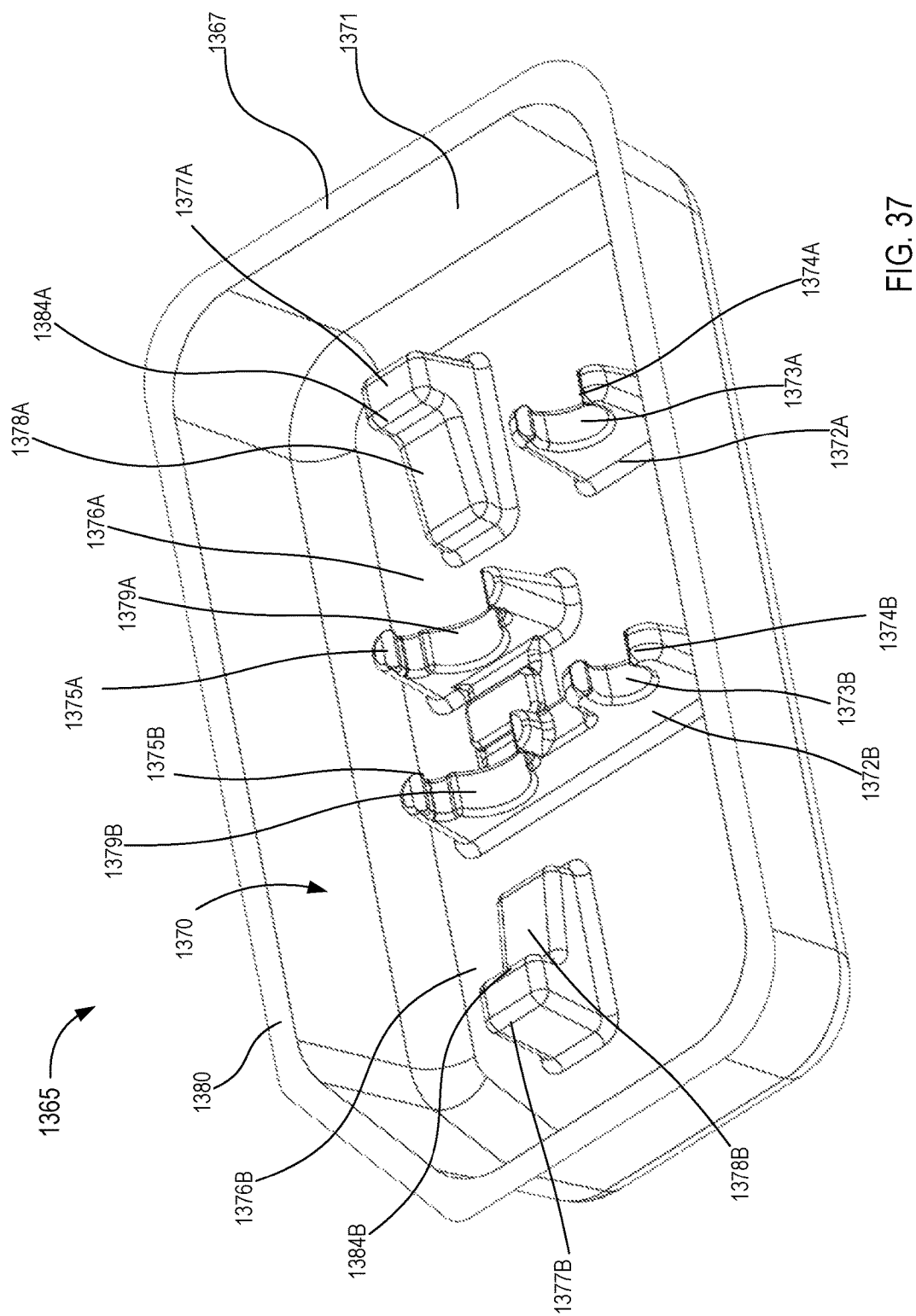
FIGS. 37 and 38 are a top perspective views of a second tray member included in the kit shown in FIGS. 13 and 14.
Figure 38:
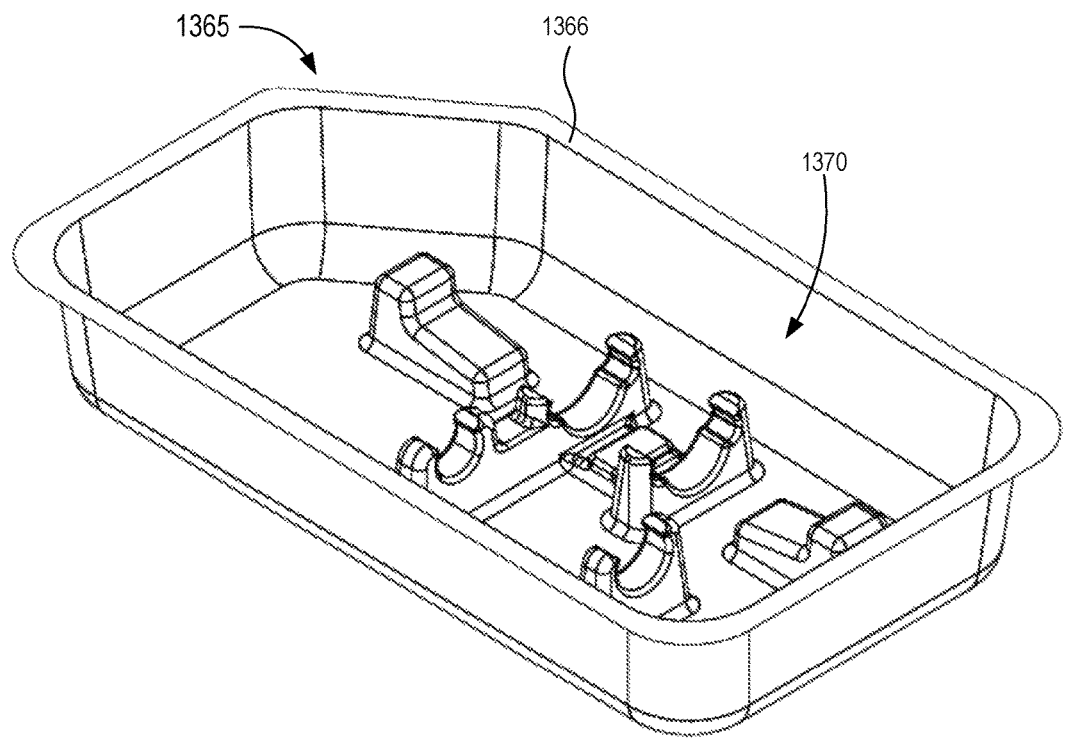
Figure 39:
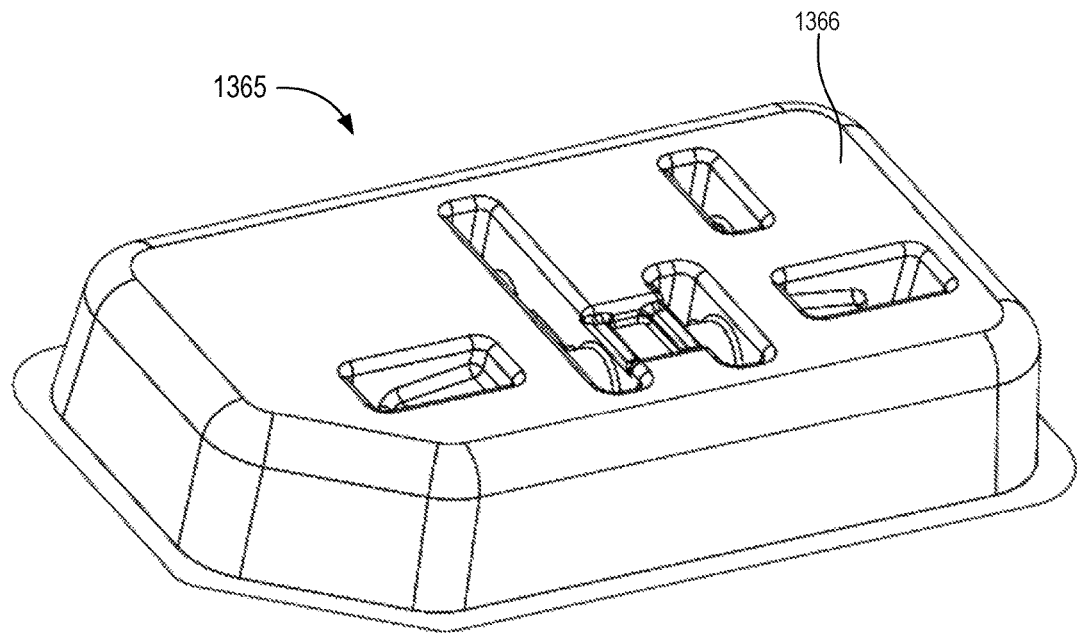
FIG. 39 is a bottom perspective view of the second tray member shown in FIGS. 37 and 38.
Figure 40:
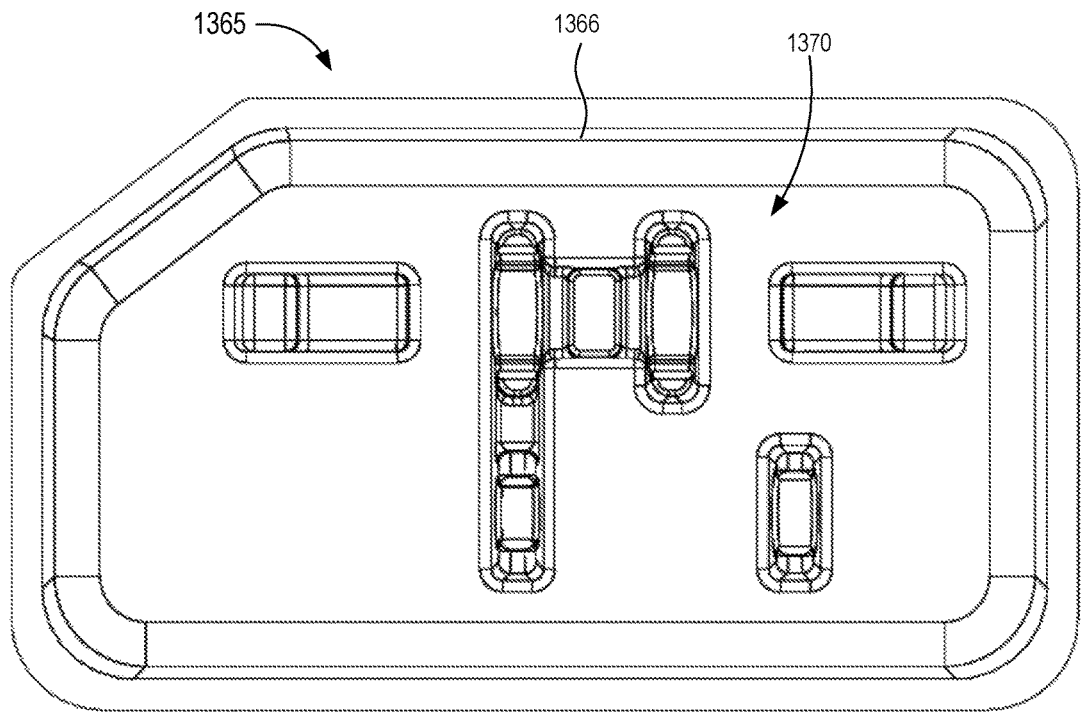
FIGS. 40 and 41 are a top view and a bottom view, respectively, of the second tray member shown in FIGS. 37 and 38.
Figure 41:
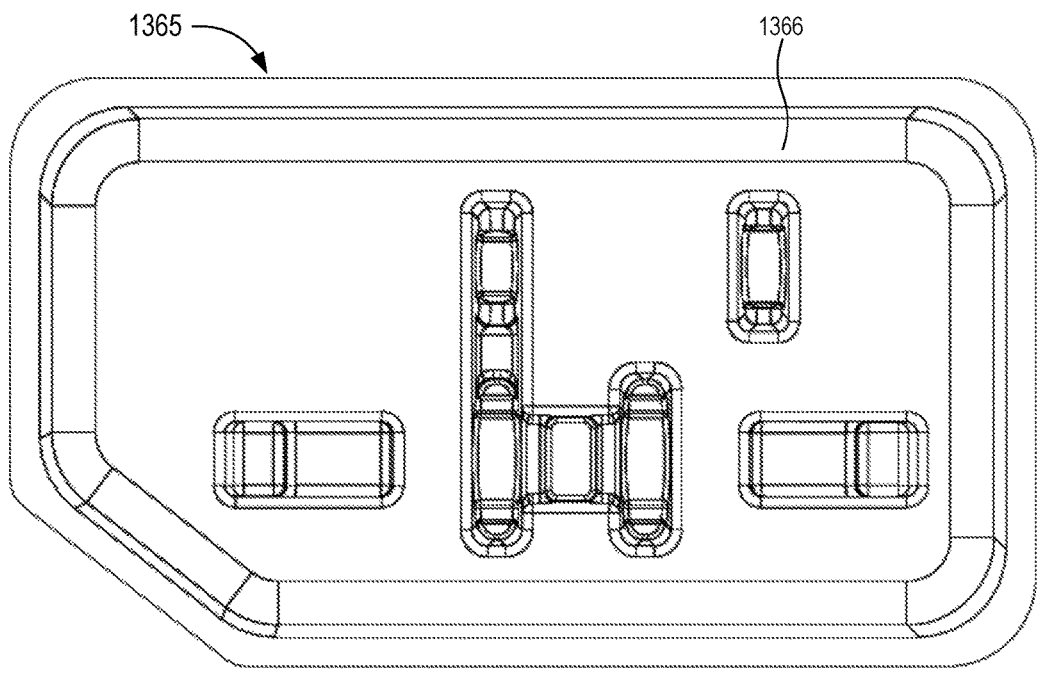
Figure 42:
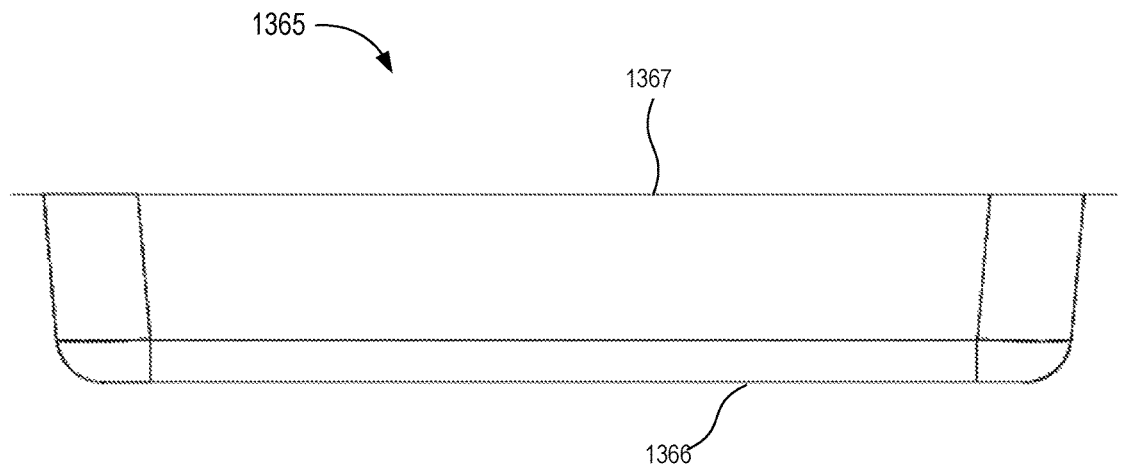
FIGS. 42 and 43 are a front side view and a right side view, respectively, of the second tray member shown in FIGS. 37 and 38.
Figure 43:
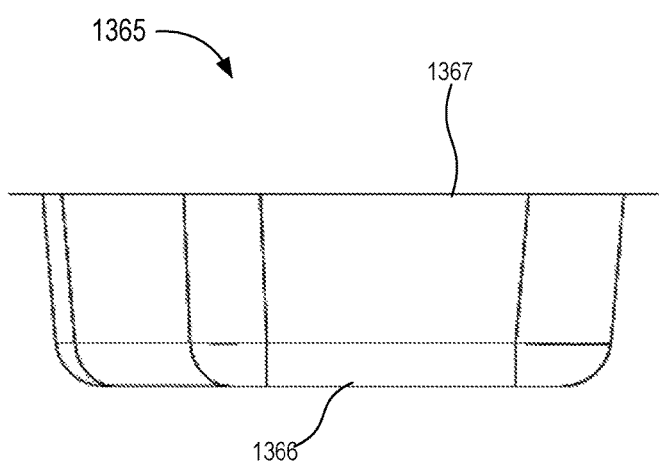
Figure 44:
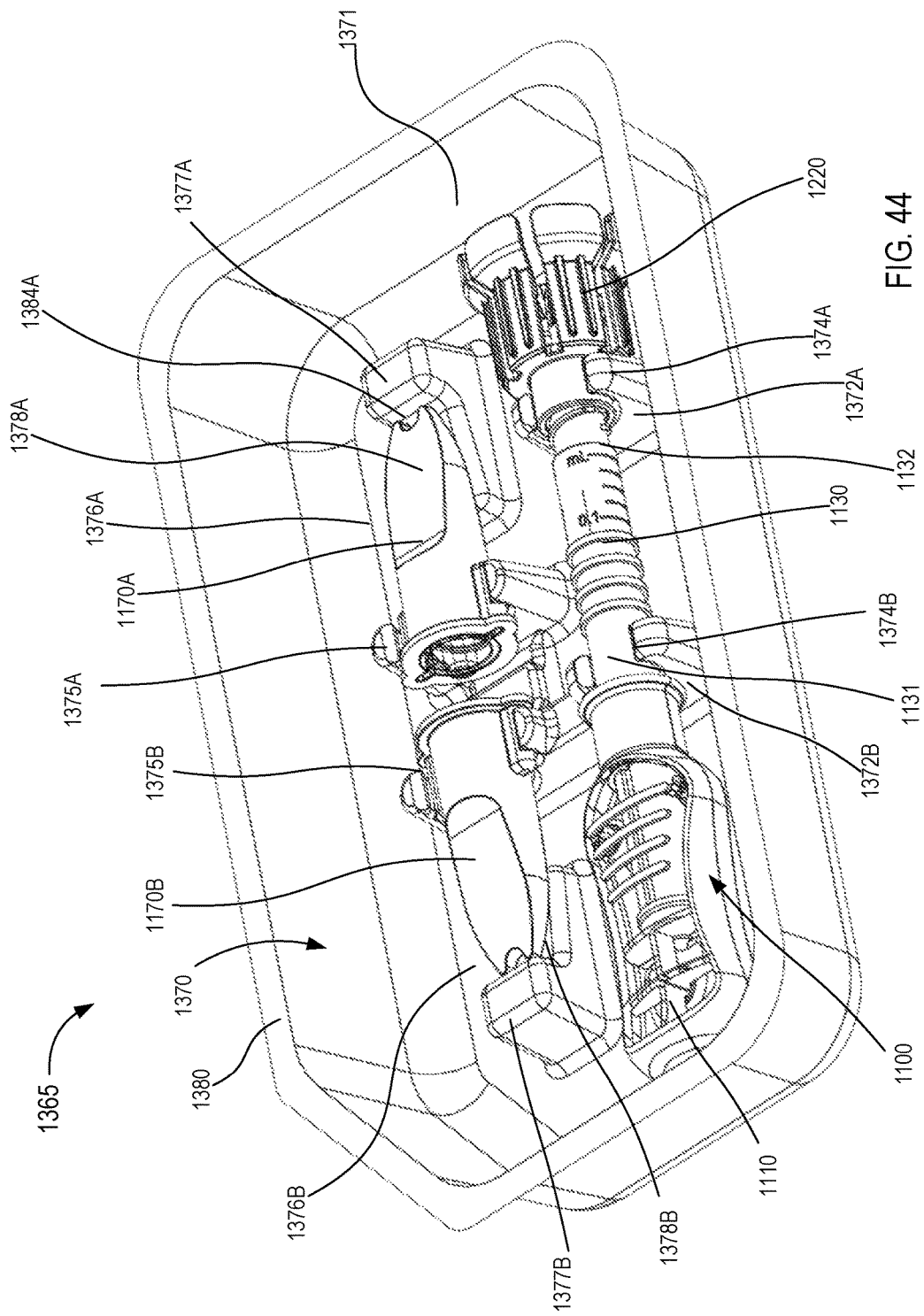
FIG. 44 is a perspective view of a portion of the kit shown in FIGS. 13 and 14, including the second tray member.

As shown in FIGS. 17, 37-45, the inner tray 1365 includes a first (or outer) side surface 1366 and a second (or inner) side surface 1367. The inner tray 1365 further includes a side wall (also referred to as a wall or body) 1371, and defines a volume 1370. As described in more detail, the volume 1370 is maintained as a sterile volume when the kit 1000 is in the first configuration, and contains the injector assembly 1100, and the two needle assemblies 1160A, 1160B (see FIG. 44). More specifically, the side wall 1371 includes a first injector retention member (or retainer) 1372A, a second injector retention member (or retainer) 1372B, a first needle retention portion 1376A, and a second needle retention portion 1376B. As shown in FIG. 37, the first injector retention member 1372A includes a retainer (or hook) 1374A that defines an opening 1373A, and the second injector retention member 1372B includes a retainer (or hook) 1374B that defines an opening 1373B. As shown in FIGS. 44 and 47, when the kit 1000 is in the first (or storage) configuration, a portion of the injector barrel 1130 is retained within the opening 1373B by the retainer 1374B. Similarly, the proximal end 1221 of the vial adapter 1220 is retained within the opening 1373A by the retainer 1374A. The retainers 1374A, 1374B are sized to produce an interference (or snap) fit to maintain the injector assembly 1100 in a secure position during storage, shipping, and when the kit 1000 is being prepared for use, as described herein. As described above, the injector protrusion 1350 of the outer tray 1340 also exerts pressure against the injector barrel 1130 to maintain the injector assembly 1100 in a secure position during storage, shipping, and when the kit 1000 is being prepared for use.

As shown in FIG. 37, the first needle retention portion 1376A includes a protrusion 1377A and a retainer 1375A. The protrusion 1377A has an end stop 1384A and a tapered surface 1378A that corresponds to the tapered surface 1172 of the needle cap 1170. The retainer 1375A defines a central opening and a pair of side openings 1379A. Similarly, the second needle retention portion 1376B includes a protrusion 1377B and a retainer 1375B. The protrusion 1377B has an end stop 1384B and a tapered surface 1378A that corresponds to the tapered surface 1172 of the needle cap 1170. The retainer 1375B defines a central opening and a pair of side openings 1379A. As shown in FIGS. 44 and 46, when the kit 1000 is in the first (or storage) configuration, the outer protrusions 1175 of the needle caps 1170A, 1170B are retained within the side openings 1379A, 1379B, respectively by the retainers 1375A, 1375B, respectively. The retainers 1375A, 1375B are sized to produce an interference (or snap) fit to maintain the needle assemblies 1160A, 1160B, respectively, in a secure position during storage, shipping, and when the kit 1000 is being prepared for use, as described herein. Moreover, the tapered surfaces 1378A, 1378B are maintained in contact with the tapered surface of the needle caps 1170A, 1170B, respectively. Additionally, as described above, the tapered surfaces 1353A, 1353B of the outer tray 1340 are maintained in contact with the opposite side of the tapered surface of the needle caps 1170A, 1170B, respectively.

As shown in FIG. 44, the needle caps 1170A, 1170B are maintained in contact with or in close proximity to the end stops 1384A, 1384B, respectively. This arrangement limits contact between the user and the distal end tips of the needle caps 1170A, 1170B. For example, in some methods, the distal end tips can be used to measure and/or mark the surface of the eye, and thus minimizing contact between the user and the areas that will directly contact the eye is advantageous. Similarly, the arrangement of the needle assemblies 1160A, 1160B within the inner tray 1365 can limit contact with other portions of the needle assemblies, such as the proximal end portion that is directly coupled to the injector barrel 1130.

The inner tray 1365 includes a flange 1380 that surrounds the volume 1370. As described above, the flange 1380 is releasably retained within the locking protrusions 1349A, 1349B the outer tray 1340. As described in more detail below, the locking protrusions 1349A, 1349B are configured to releasably retain the flange 1380 such that when a force is exerted against the outer tray 1340, a portion of the side wall 1348, the locking protrusions 1349A, 1349B, and/or the flange 1380 deform to release the flange 1380.

Figure 45:
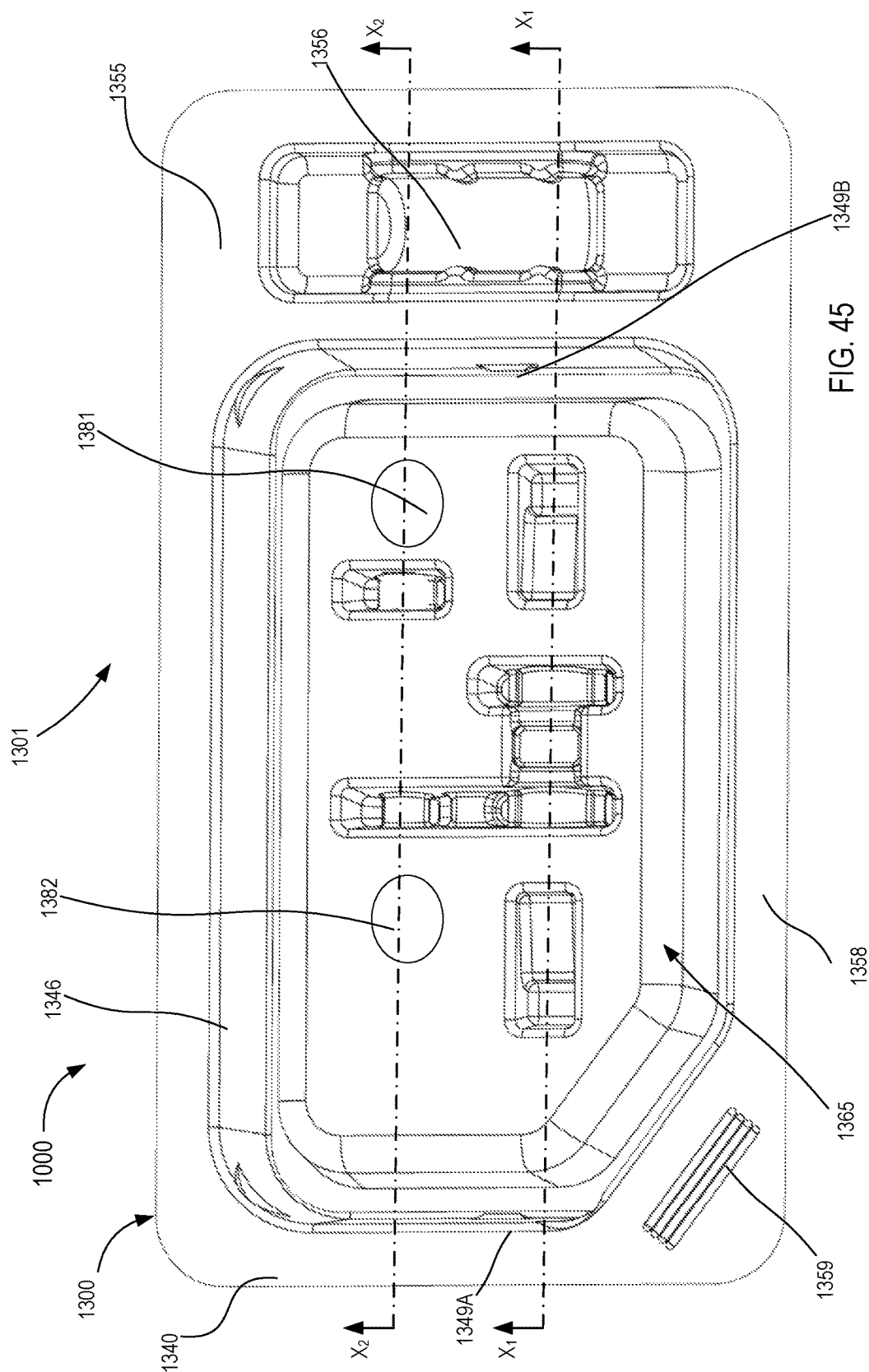
FIG. 45 is a top perspective view of a portion of the kit shown in FIGS. 13 and 14, including the first tray member and the second tray member.

Moreover, as shown in FIG. 45, in some embodiments, the bottom of the inner tray 1365 includes a first vent opening 1381 and a second vent opening 1382. The vent openings provide fluid communication between the volume 1370 of the inner tray 1365 and the first volume 1347 of the outer tray 1340. This arrangement allows for repeatable release of the inner tray 1365 from the outer tray 1340 (e.g., by reducing any air lock that maintains the parts together). This arrangement also allows for more efficient sterilization by permitting the passage of a sterilant gas, such as ethylene oxide, which could be used to sterilize the contents of the tray. Although the vent openings are shown as having a circular shape, in other embodiments, the vent openings can have any suitable shape (e.g., oval, rectangular, or any suitable discontinuous shape). The inner tray 1365 can have any number of vent openings. In yet other embodiments, the inner tray 1365 can be devoid of any vent openings.

Figure 17:
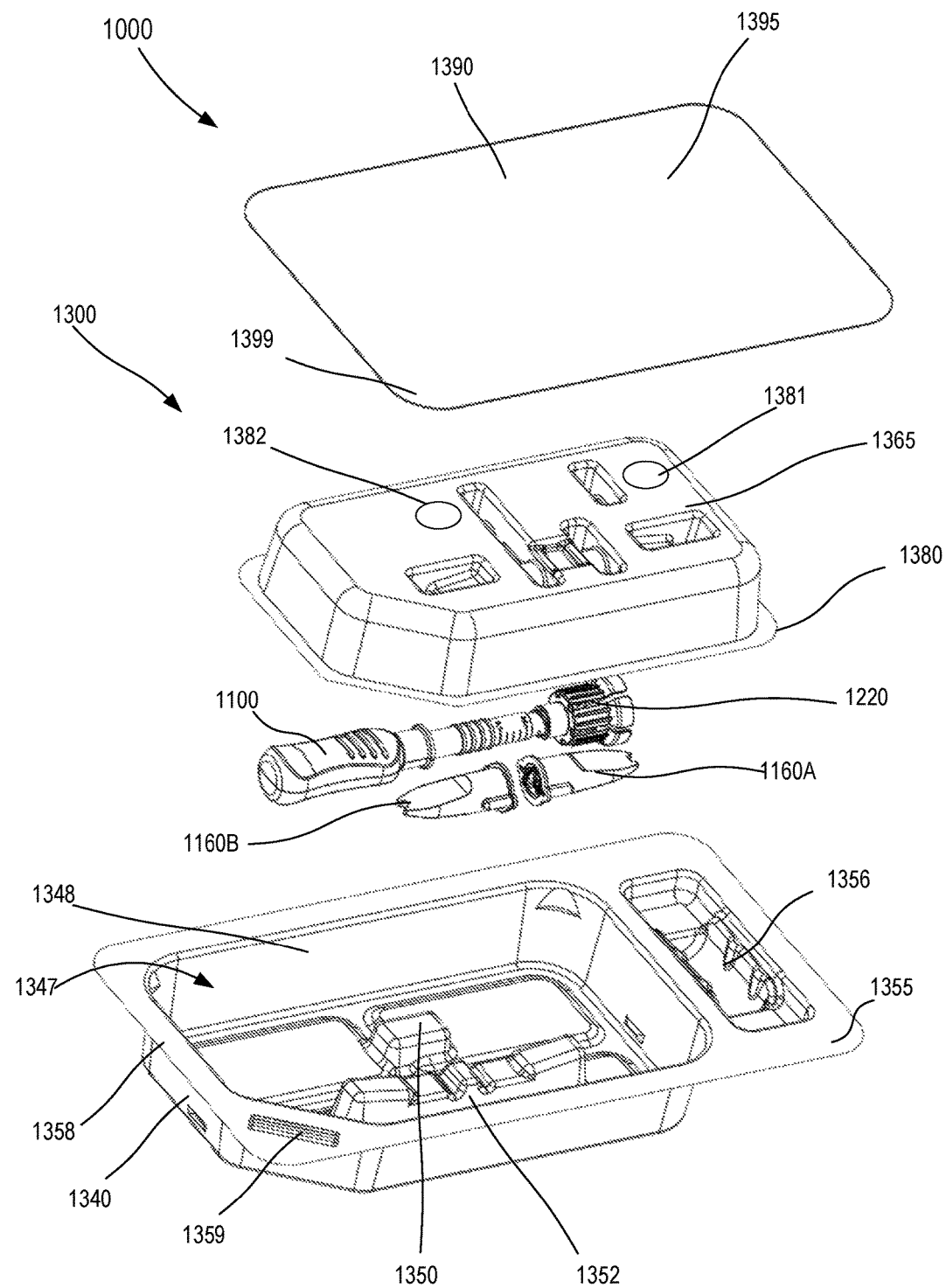
FIG. 17 is an exploded perspective view of a tray assembly portion of the kit shown in FIGS. 13 and 14.
Figure 18:
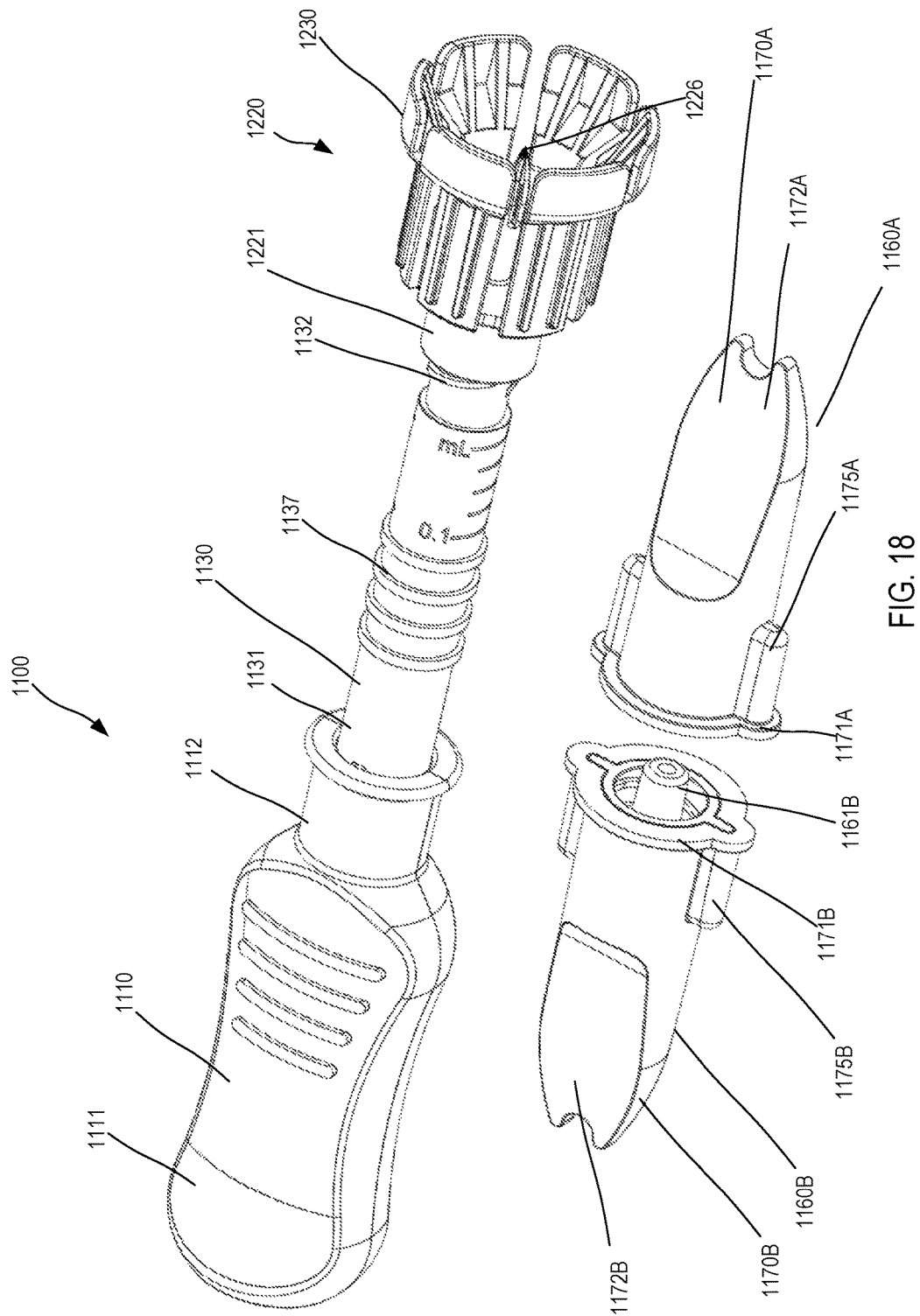
FIG. 18 is a perspective view of an injector assembly included in the kit shown in FIGS. 13 and 14.
Figure 22:
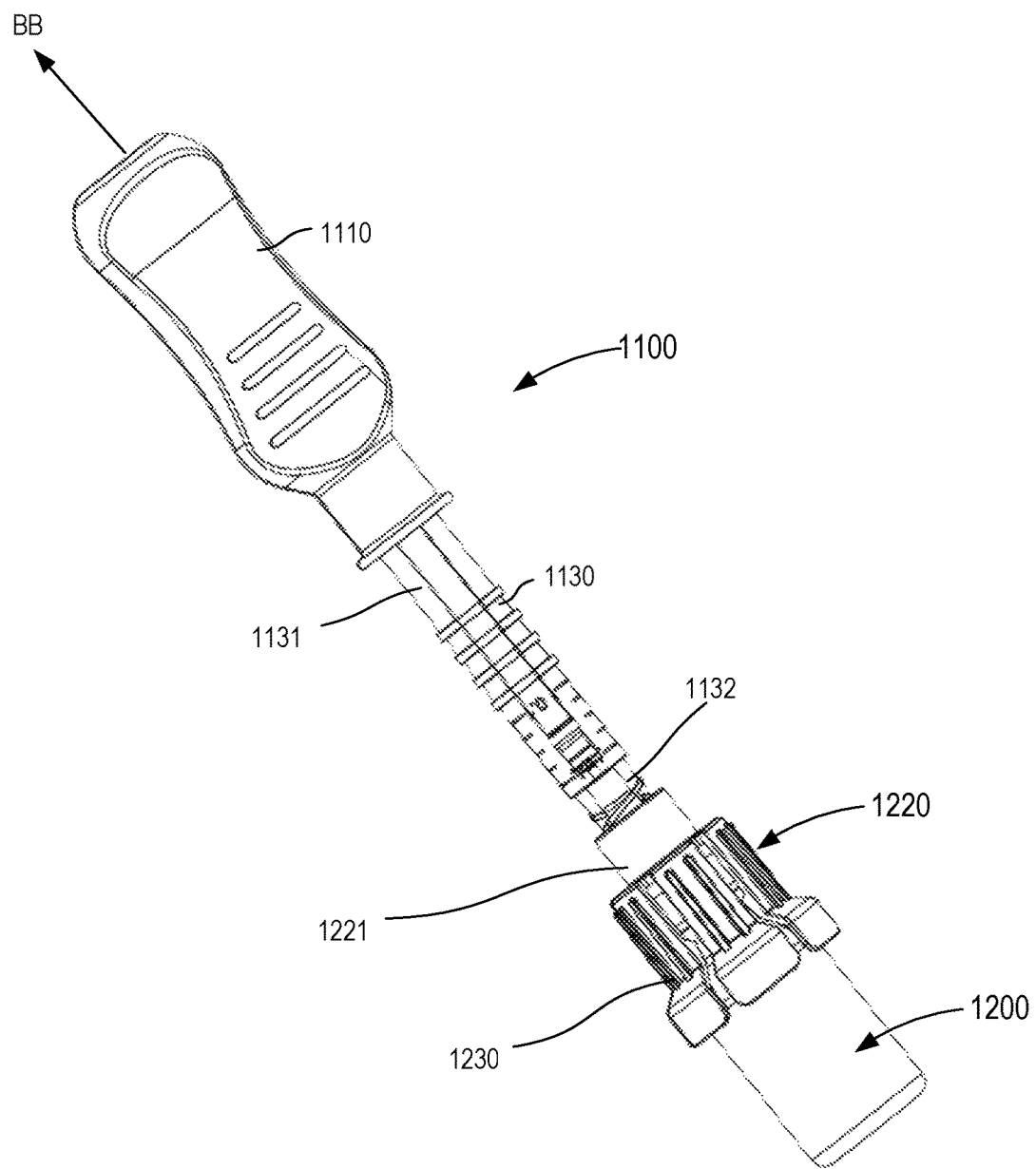
FIG. 22 is as perspective view of the injector assembly shown in FIG. 18 in use with the vial adapter shown in FIGS. 19 and 20, according to an embodiment.
Figure 23:
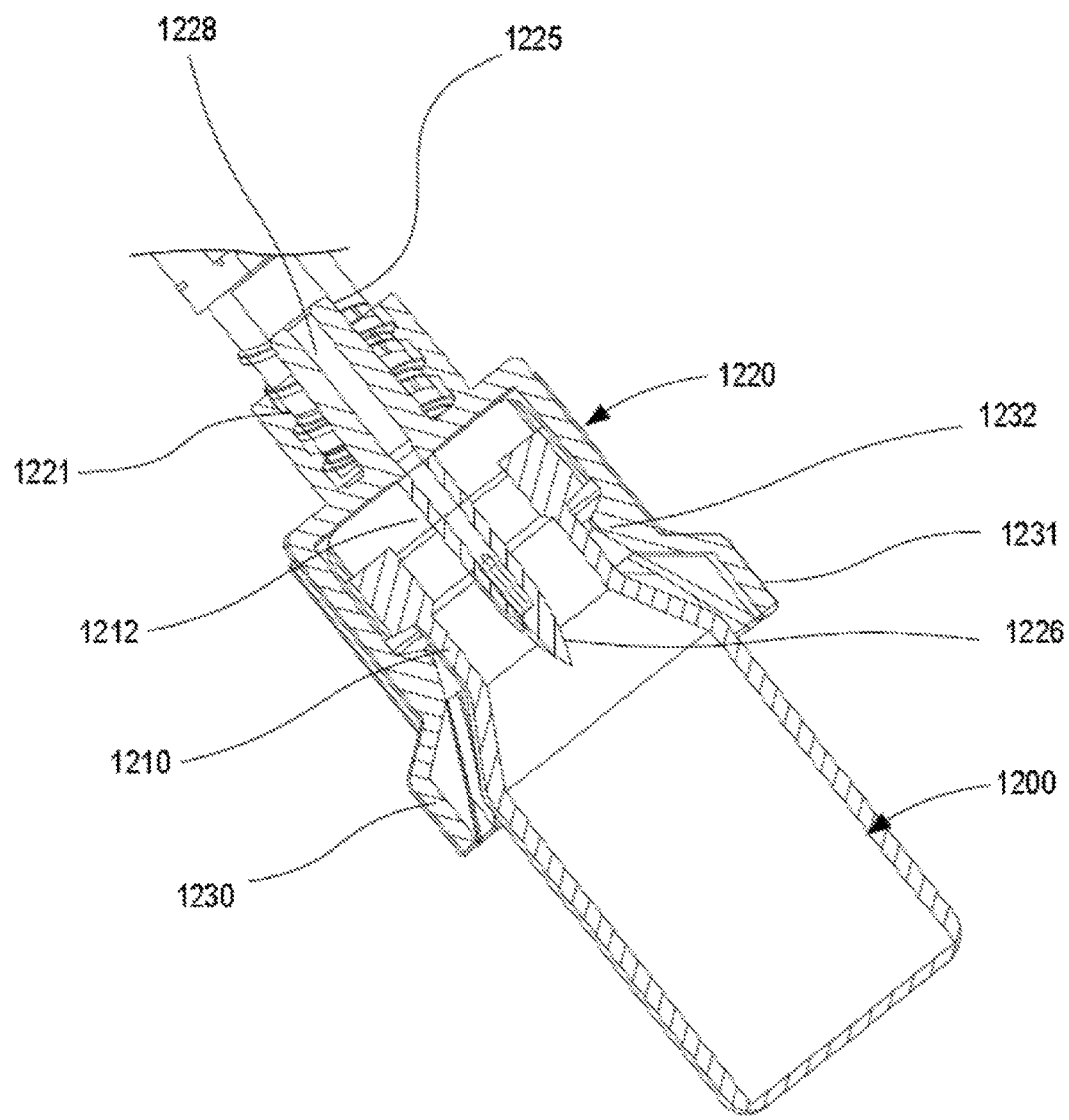
FIG. 23 is a side cross-sectional view of the vial adapter and injector assembly shown in FIG. 22.
Figure 24:
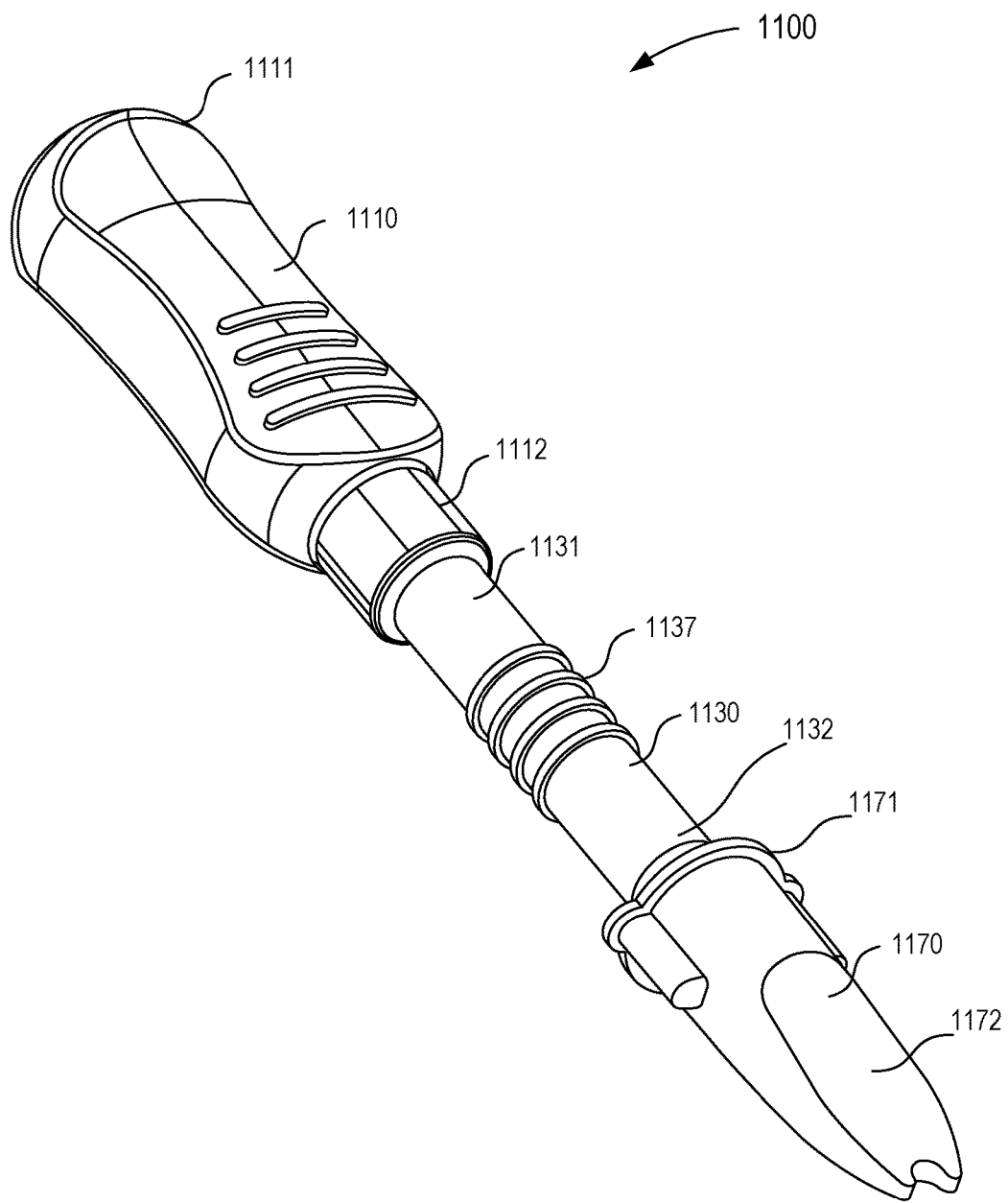
FIGS. 24 and 25 are perspective views of the injector assembly shown in FIG. 18 in various stages of use.
Figure 25:
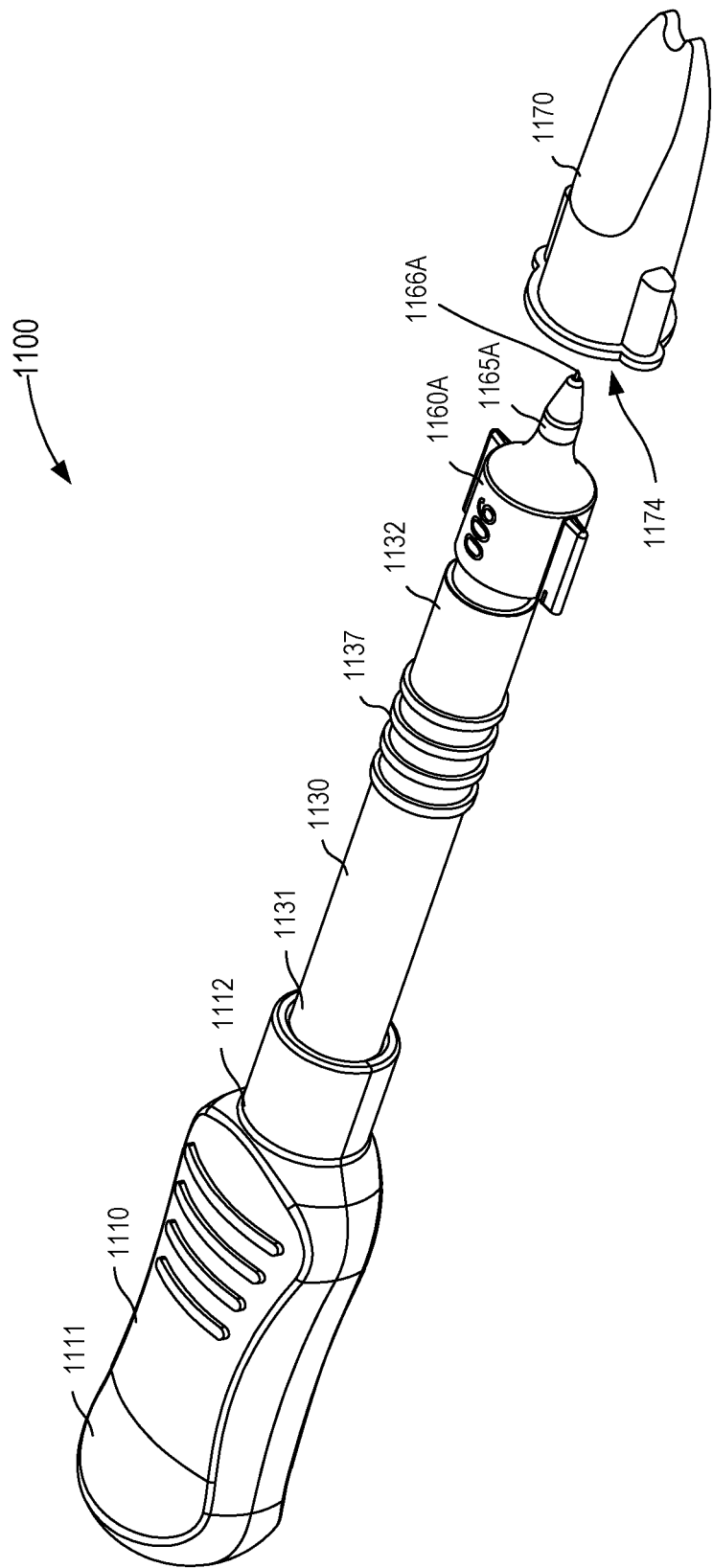
Figure 26:
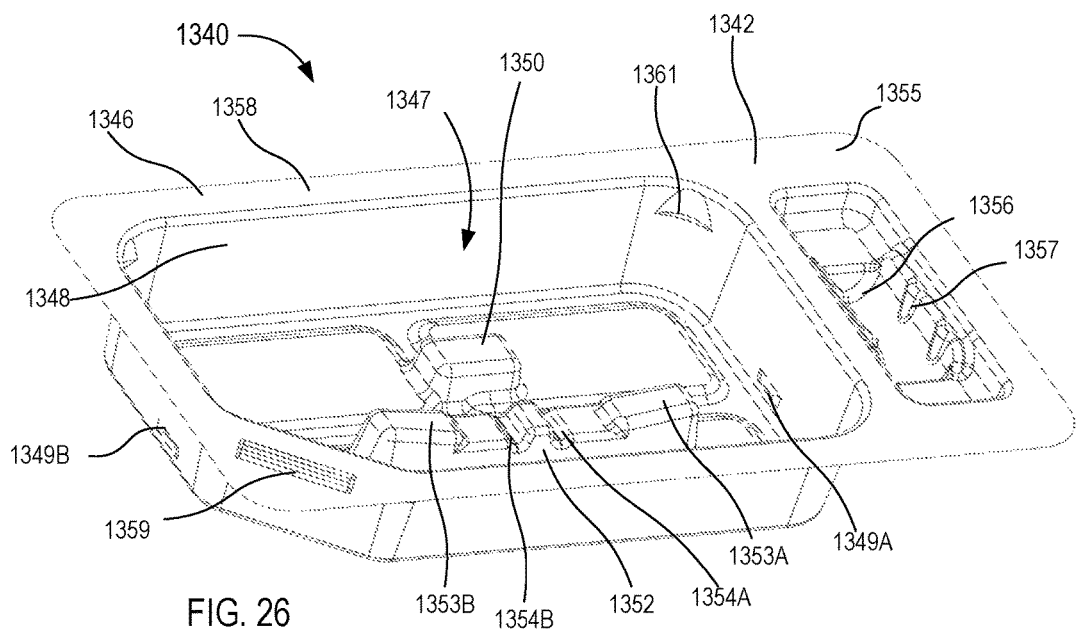
FIGS. 26-28 are top perspective views of a first tray member included in the kit shown in FIGS. 13 and 14.
Figure 27:
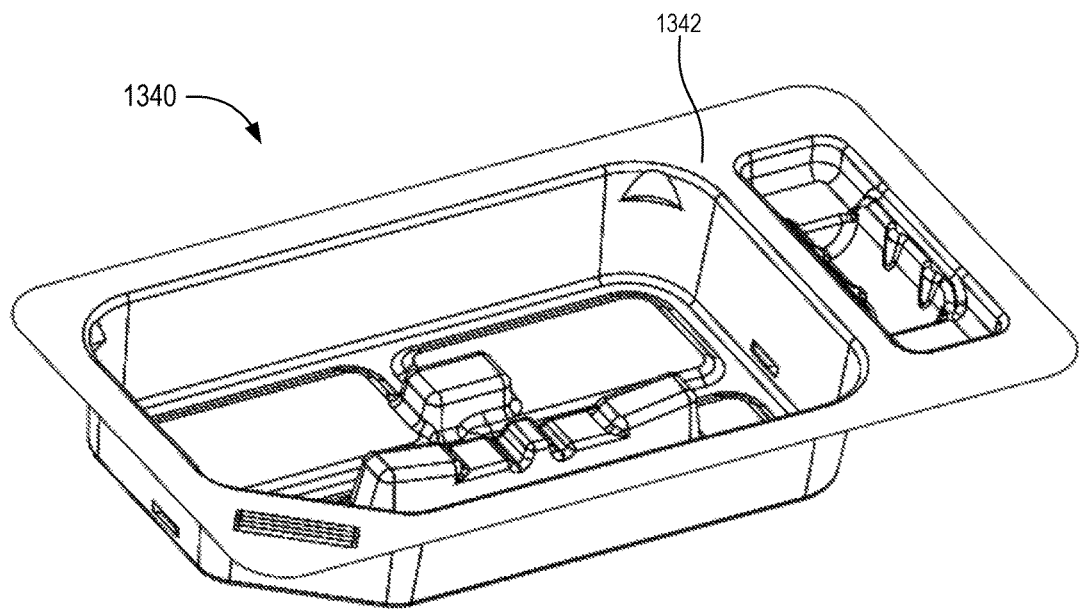
Figure 28:
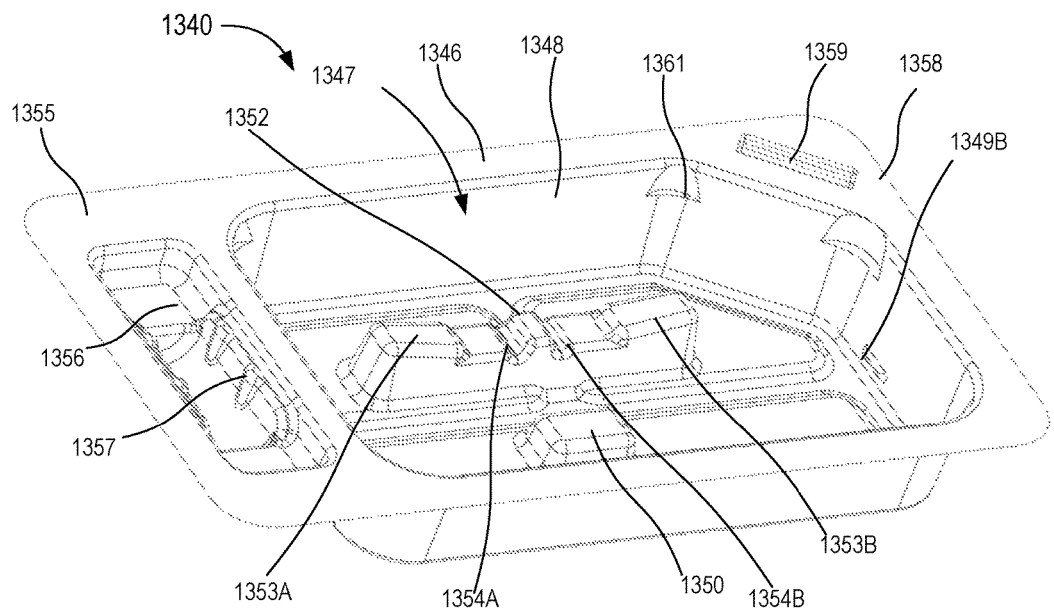
Figure 29:
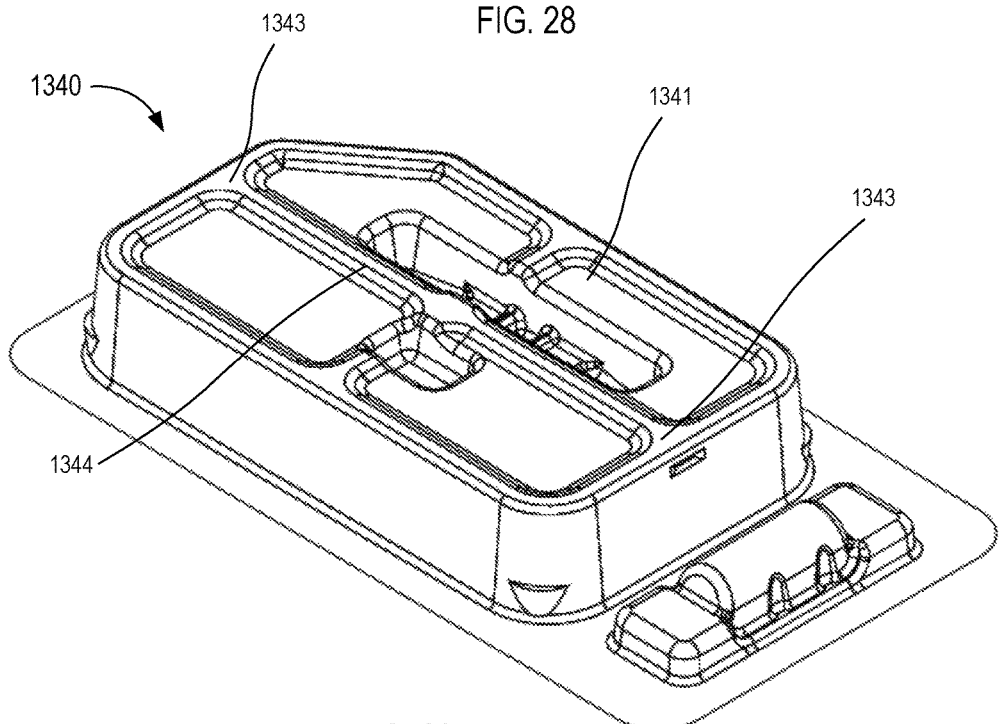
FIG. 29 is a bottom perspective view of the first tray member shown in FIGS. 26-28.
Figure 30:
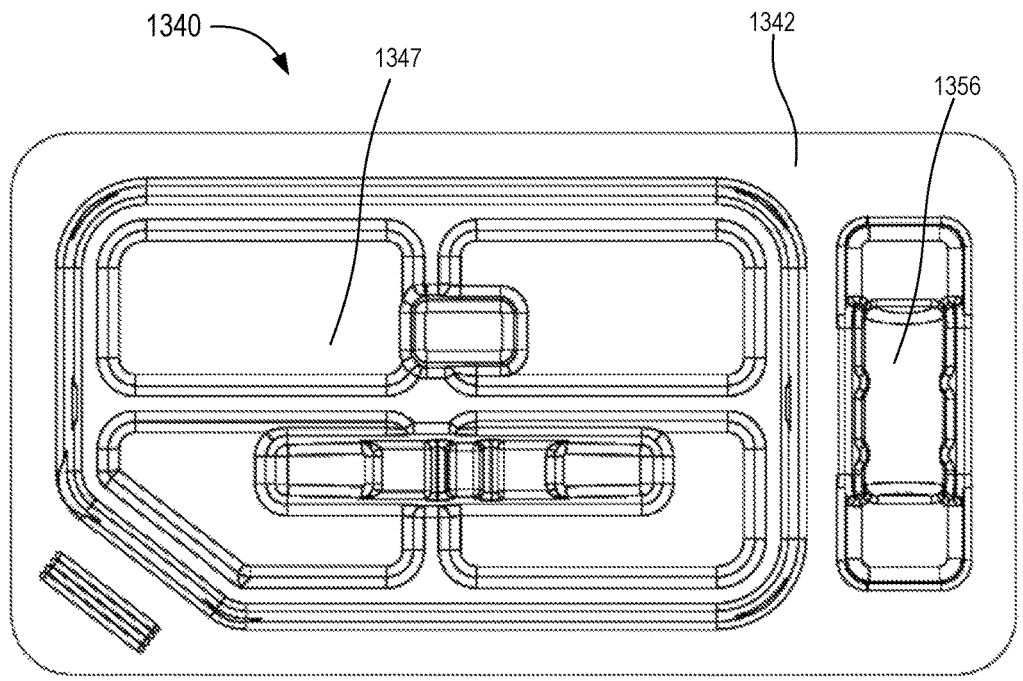
FIGS. 30 and 31 are a top view and a bottom view, respectively, of the first tray member shown in FIGS. 26-28.
Figure 31:
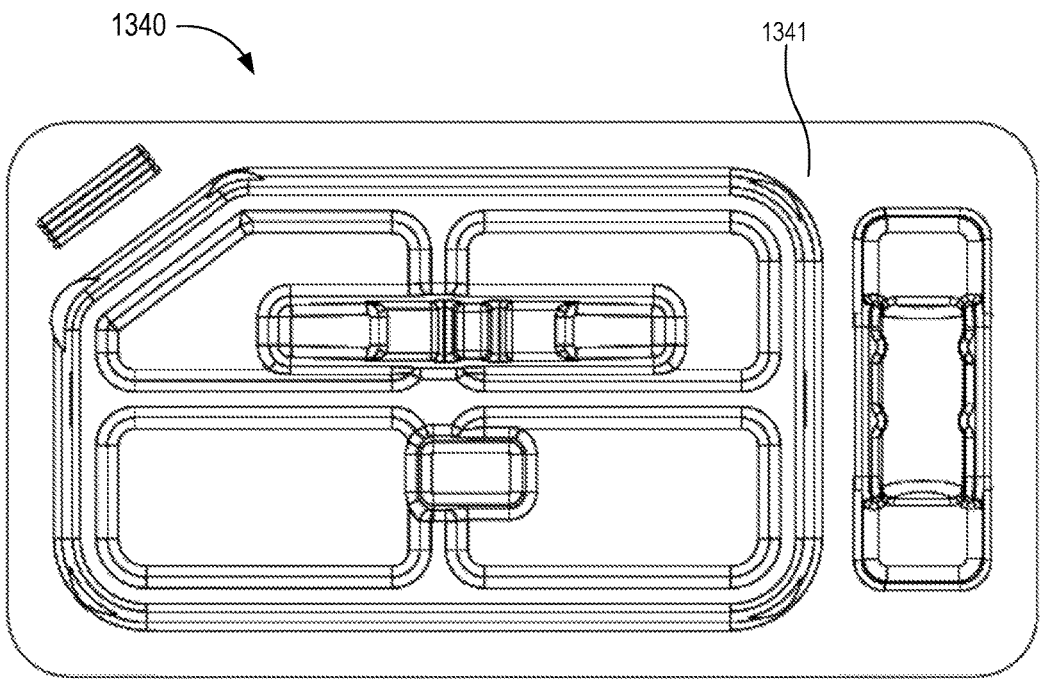
Figure 32:
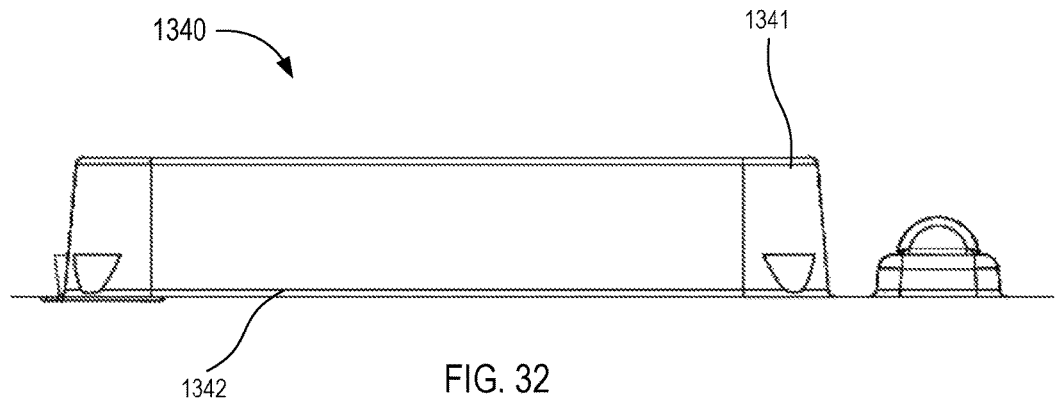
FIGS. 32 and 33 are a front side view and a back side view, respectively, of the first tray member shown in FIGS. 26-28.
Figure 33:
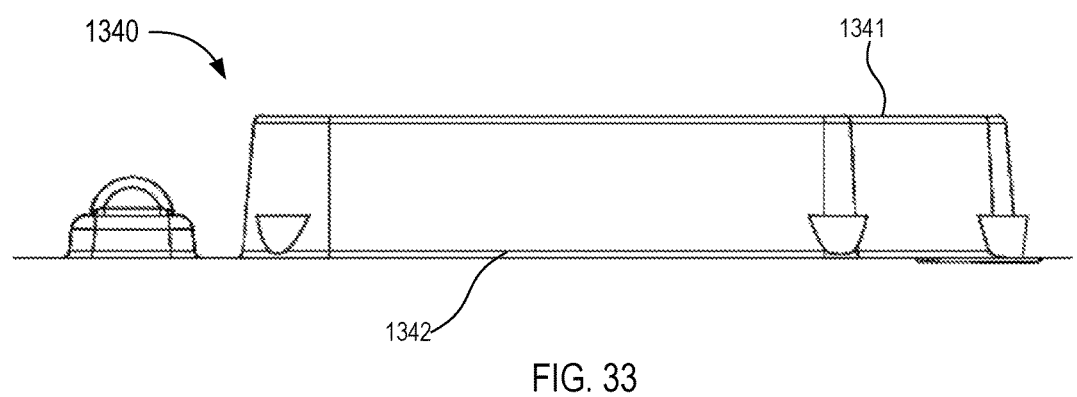
Figure 34:
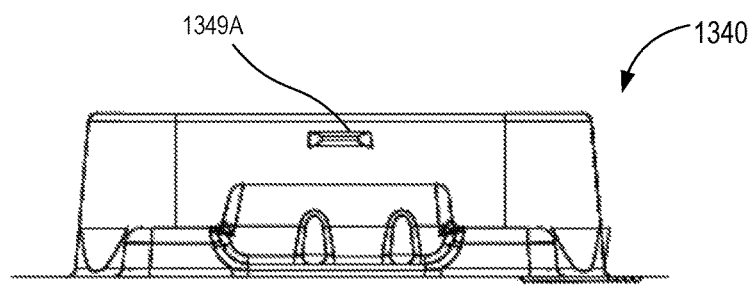
FIGS. 34 and 35 are a right side view and a left side view, respectively, of the first tray member shown in FIGS. 26-28.
Figure 35:
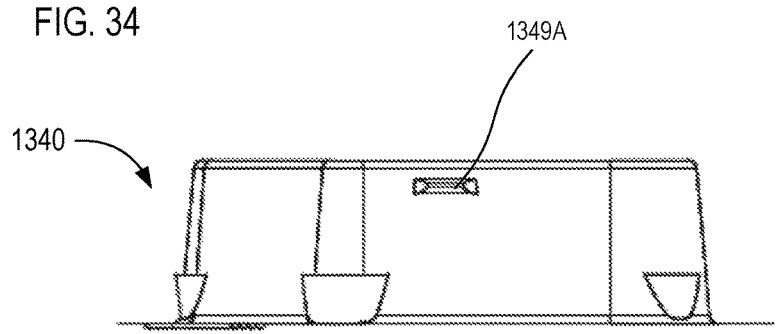

As shown in FIG. 17, the kit 1000 includes an injector assembly 1100, a vial adapter 1220, and two needle assemblies 1160A, 1160B. FIGS. 22 and 23 show the injector assembly 1100 coupled to the vial 1200 via the vial adapter 1220, for example, to withdraw the medicament from the vial 1200. FIGS. 24 and 25 are perspective views of the injector assembly 1100 coupled to one of the needle assemblies (identified as the needle assembly 1160A). The injector assembly 1100 (also referred to as the medical injector) is configured to deliver a medicament to ocular tissue according to the methods described in International Patent Application No. WO2015/19584, entitled "METHODS AND DEVICES FOR TREATING POSTERIOR OCULAR DISORDERS" and U.S. Pat. No. 9,180,047, entitled "APPARATUS AND METHODS FOR OCULAR INJECTION," each of which is incorporated herein by reference in its entirety.

As shown, the injector assembly 1100 includes a handle 1110, a barrel 1130, a piston (not shown), and a needle assembly 1160A (also referred to as a hub or hub assembly. The handle 1110 can be any suitable shape, size, and/or configuration. For example, in some embodiments, the handle 1110 can have an ergonomic shape and/or size, which can enable a user to manipulate the injector 1100 with one hand or with two hands. The handle 1110 has a proximal end portion 1111 and a distal end portion 1112, and defines an inner volume that receives and/or is configured to house at least a portion of the barrel 1130 and the piston. More specifically, a proximal end portion of the piston is coupled within the inner volume of the handle 1110 and a distal end portion of the piston is movably disposed within the barrel 1130. The distal end portion of the piston can be coupled to an elastomeric member (or plunger) within the barrel. In this manner, movement of the handle 1110 relative to the barrel 1130 causes the piston (and thus, the elastomeric member) to move within the barrel 1130 either to produce a vacuum (to draw a dose of medicament into the barrel) or to produce to a positive pressure (to deliver the dose of medicament out of the barrel).

The barrel 1130 of the injector 1100 can be any suitable shape, size, or configuration. As shown in FIGS. 24 and 25, the barrel 1130 has a proximal end portion 1131 and a distal end portion 1132 and defines a lumen therethrough. In addition, the barrel 1130 has an outer surface that includes a grip portion 1137. The grip portion 1137 can facilitate the use of the medical injector by providing a user with a predetermined location to engage the injector 1100. The grip portion 1137 can have any suitable surface finish or the like, which can, in some instances, increase a friction between the grip portion 1137 and a user's fingers and/or hand. In other embodiments, the barrel 1130 does not include a grip portion.

As described above, the barrel 1130 movably receives at least a portion of the piston (not shown), and defines a medicament volume configured to receive, store, house, and/or otherwise contain a medicament (e.g., a corticosteroid such as triamcinolone acetonide, or any other medicament described herein). In some embodiments, at least a portion of the barrel 1130 can be substantially transparent and/or can include an indicator or the like configured to allow a user to visually inspect a volume of fluid (e.g., medicament/therapeutic formulation) therein. In some instances, such an indicator can be, for example, any number of lines and/or markings associated with a volume of fluid disposed within the barrel 1130. In other embodiments, the barrel 1130 can be substantially opaque and/or does not include an indicator or the like.

The proximal end portion 1131 of the barrel 1130 includes a flanged end that is disposed within the inner volume of the handle 1110. Specifically, at least the proximal end portion 1131 of the barrel 1130 can be inserted into the handle 1110 in such a manner that the handle 1110 can be moved relative to the barrel 1130. In other words, at least the proximal end portion 1131 of the barrel 1130 is movably disposed within the inner volume defined by the handle 1110. In this manner, during the dose preparation operation, substantially all of the force applied by the user will urge the handle 1110 (and therefore the piston) in the proximal direction (arrow BB in FIG. 22). During the injection operation, substantially all of the force applied by the user will urge the handle 1110 (and therefore the piston) in the distal direction.

The distal end portion 1132 of the barrel 1130 includes and/or forms a coupler configured to be physically and fluidically coupled to the needle assembly 1160A (and the needle assembly 1160B) and the vial adapter 1220. In some embodiments, the distal end portion 1132 of the barrel includes threads that can matingly engage threads of the needle assembly 1160A and the vial adapter 1220.

The needle assembly 1160A has a proximal end portion and a distal end portion. The proximal end portion of the needle assembly 1160A is configured to be coupled to the distal end portion 1132 of the barrel 1130. For example, the needle assembly 1160A can include threads that can matingly engage threads of the barrel 1130 to couple the needle assembly 1160A to the barrel 1130 and to place the needle assembly 1160A in fluid communication with the barrel 1130. In some embodiments, the needle assembly 1160A can be coupled to the barrel 1130 by a locking mechanism and/or the like such as, for example, a Luer-Lok® (or other locking mechanism) configured to form a fluid tight seal with the distal end portion 1132 of the barrel 1130 when coupled thereto.

The distal end portion of the needle assembly 1160A includes and/or is coupled to a base 1165A, which in turn, is coupled to and/or forms a microneedle 1166A, as described below. As shown, the needle assembly 1160A can include an indicia provide a visual indication associated with one or more characteristics of the microneedle 1166A. For example, in this embodiment, the indicator portion provides a visual indication associated with an effective length of the microneedle 1166A (e.g., "900" micrometers, as shown in FIG. 25).

The cap 1170 of the injector 1100 is removably disposed adjacent the distal end portion 1132 of the barrel 1130 and is configured to substantially house, cover, enclose, protect, isolate, etc. at least a portion of the needle assembly 1160A (and the needle assembly 1160B). More specifically, the cap 1170 can be moved relative to the remaining portions of the injector assembly 1100 to position at least a portion of the needle assembly 1160A within an inner volume 1174 (see, e.g., FIG. 25) of the cap 1170. As such, the cap 1170 can have a size and/or shape that is associated with and/or at least partially based on a size and/or shape of the needle assembly 1160A. In some embodiments, the cap 1170 and a portion of the needle assembly 1160A can collectively define a friction fit or the like, which can be operable in maintaining the cap 1170 in a substantially fixed position relative to the needle assembly 1160A. In addition, in some embodiments, the cap 1170 and the portion of the needle assembly 1160A can collectively form a substantially fluid tight and/or substantially hermetic seal, which in turn, can maintain the sterility of a microneedle 1166 prior to use of the injector assembly 1100. For example, although not shown, the cap 1170 can include a plug, a seal, a sterilization member (e.g., wipe, pad, etc.), and/or the like configured to maintain the sterility of the microneedle 1166 prior to use.

Figure 19:
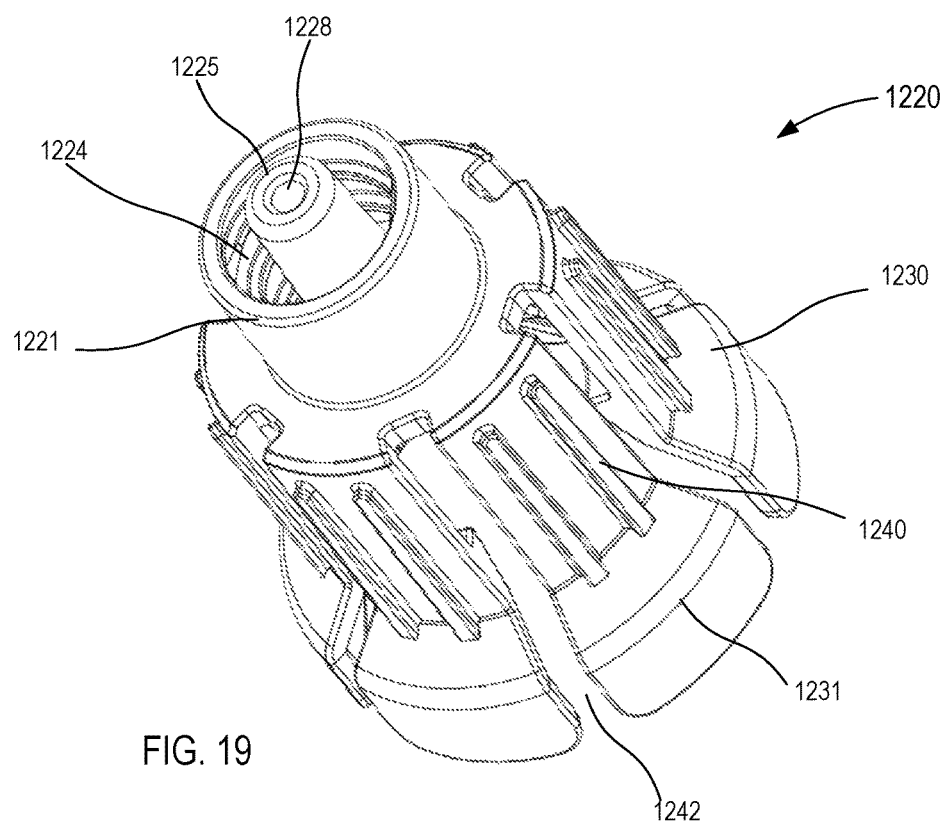
FIGS. 19 and 20 are perspective views of a vial adapter included in the kit shown in FIGS. 13 and 14.
Figure 20:
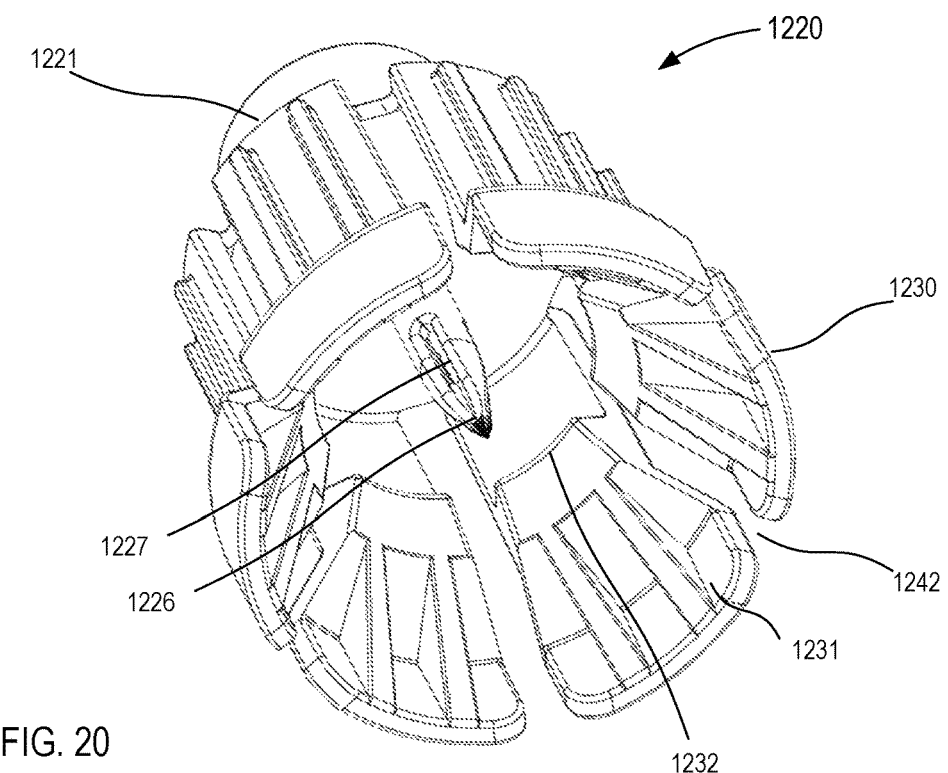
Figure 21:
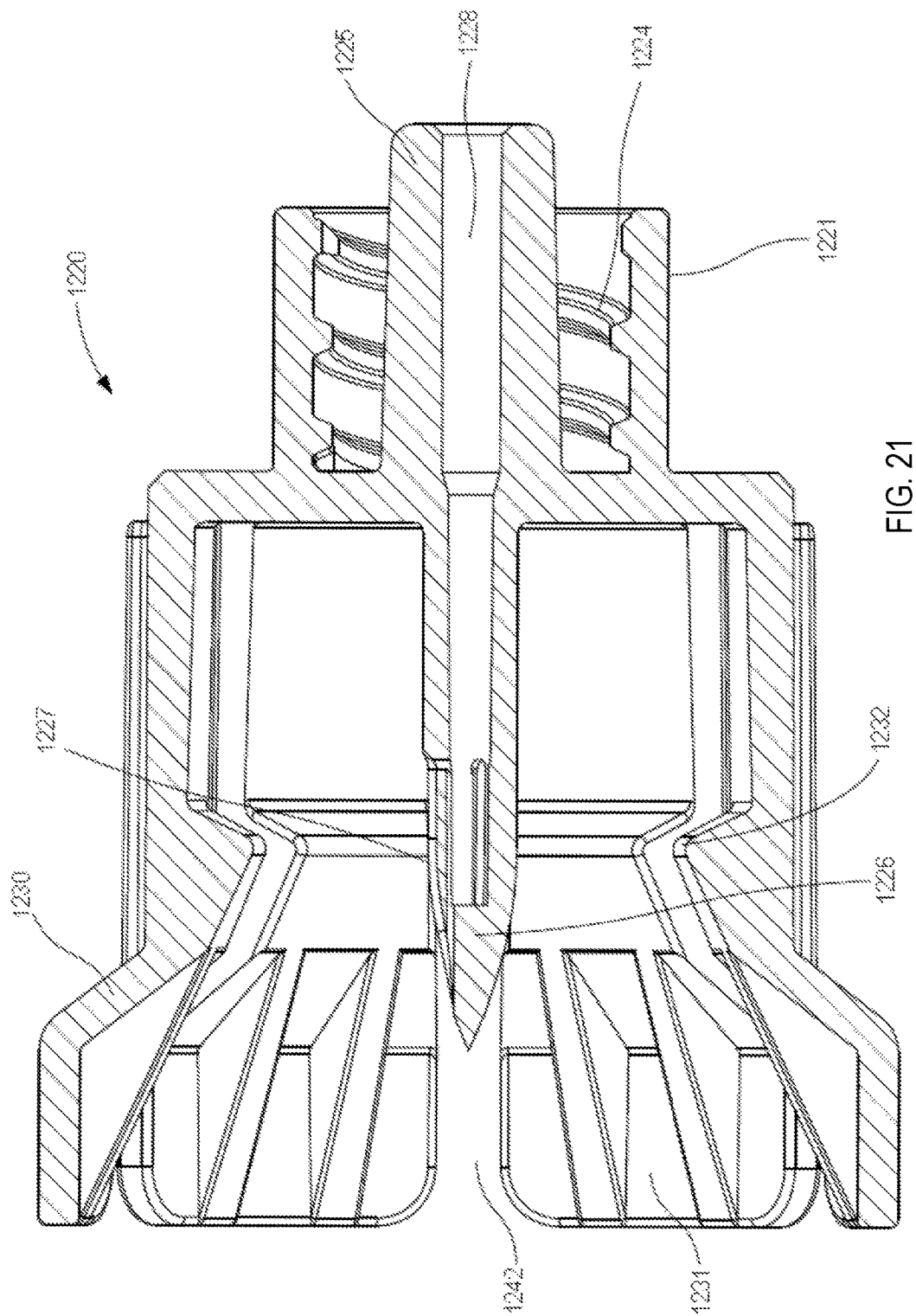
FIG. 21 is a side cross-sectional view of the vial adapter shown in FIGS. 10 and 20.

As described in more detail below, the vial adapter 1220 is used to couple the injector assembly 1100 to the vial 1200 to transfer and/or extract a medicament from within the vial 1200 (or medicament container) to the medicament volume of the barrel 1130. As shown in FIGS. 19-20, the vial adapter 1220 has a proximal end portion 1221 and a distal end portion 1230. The proximal end portion 1221 includes a coupling portion 1224, which is a set of threads that can matingly engage threads of the barrel 1130 to couple the vial adapter 1220 to the barrel 1130. The proximal end portion 1221 also includes a delivery protrusion 1225 and a puncture member 1226 that collectively define a delivery path 1228. In this manner, when the vial adapter 1220 is coupled to the barrel 1130, a portion of the protrusion 1225 is disposed within the barrel 1130, thereby placing the barrel 1130 in fluid communication with the delivery path 1228. In some embodiments, the vial adapter 1220 can be coupled to the barrel 1130 by a locking mechanism and/or the like such as, for example, a Luer-Lok® (or other locking mechanism) configured to form a fluid tight seal with the distal end portion 1132 of the barrel 1130 when coupled thereto. In some embodiments, the outer surface of the protrusion 1225 can be tapered, and can matingly fit within the barrel 1130 to define a fluid tight seal.

The puncture member 1226 includes a sharp tip that pierces the frangible seal (or septum) 1212 at the end portion 1211 of the vial 1200 (see e.g., FIG. 23). The puncture member 1226 defines a series of side openings 1227 in fluid communication with the delivery path 1228. In this manner, when the puncture member 1226 pierces the frangible seal 1212, the interior of the vial 1200 is placed in fluid communication with the delivery path 1228. Moreover, the side openings 1227 limit the likelihood that portions of the frangible seal 1212 will become lodged in the delivery path 1228.

The distal end portion 1230 of the vial adapter 1220 includes a series of flexible members 1231, each being separated by two slots 1242. Each flexible member 1231 includes a shoulder 1232 configured to be matingly received within the neck 1210 of the vial 1220 (see e.g., FIG. 23). The flexible members 1231 are configured to elastically deform, bend and/or flex, to allow the flexible members 1231 to be pressed over the end portion 1211 of the vial 1200 and snapped into place within the neck 1210. When the vial adapter 1220 is coupled to the vial 1200, the shoulder 1232 of each flexible member 1231 is disposed within the neck 1211 to maintain the coupling between the vial adapter 1220 and the vial 1200.

In some embodiments, the vial adapter 1220 can be similar to the adapter 21280 shown and described in International Patent Application Publication No. WO2014/179698 (Application No. PCT/US2014/036590), filed May 2, 2014 and entitled "Apparatus and Method for Ocular Injection," which is incorporated by reference herein in its entirety for all purposes.

In some embodiments, a method includes preparing the injector assembly 1100 and the desired needle assembly 1160A, 1160B for use in an ocular injection procedure. Such methods can include, for example, establishing and maintaining a sterile field, and positioning the components within the sterile field in a manner that limits the likelihood of contamination or other compromise of the sterile field. FIG. 50 is a flow chart of a method 10 of kit preparation according to an embodiment, and is described in conjunction with the kit 1000 shown and described above. In other embodiments, however, the method 10 can be performed in conjunction with any suitable kit. In use, the tray assembly 1301 is first removed from within the sleeve 1310 to move the kit from a first (or storage) configuration to a second configuration, at 12. This operation is shown in by the arrow AA in FIG. 15. The tray assembly 1301 includes the injector assembly 1100, the needle assemblies 1160A, 1160B, the vial adapter 1220, and the medicament container 1200 (or drug vial).

In some embodiments, the drug vial 1200 is removed from the outer tray 1340 and placed within the field of use, to move the kit from the second configuration to a third configuration. In other embodiments, the vial 1200 can be oriented and/or positioned within the lower tray 1340 such that the frangible seal (or septum) 1212 is facing upwards for easy access by the injector assembly 1100. In some embodiments, the method optionally includes removing the cover 1390 from the tray assembly 1301 to move the kit from the third configuration to a fourth configuration, at 13. This is performed by peeling the peel portion 1399 of the cover from about the peel protrusions 1359 of the outer tray. Removal of the cover 1390 exposes the first volume 1347 of the outer tray 1340, which is within the sterile portion of the kit 1000.

The method then includes orienting the tray assembly 1301 such that an opening defined by the outer (or first) tray 1340 that provides access to the first volume 1347 is facing downward towards a sterile surface, at 14. Moreover, the orienting is performed while maintaining the tray assembly 1301 spaced apart from the sterile surface. In this manner, the non-sterile, outer portions of the outer tray 1340 do not contact the sterile surface, thereby maintaining the integrity of the sterile field established for the injection procedure. This operation is shown in FIG. 48, which shows the tray assembly 1301 being inverted (the sterile surface is not shown).

Figure 49:
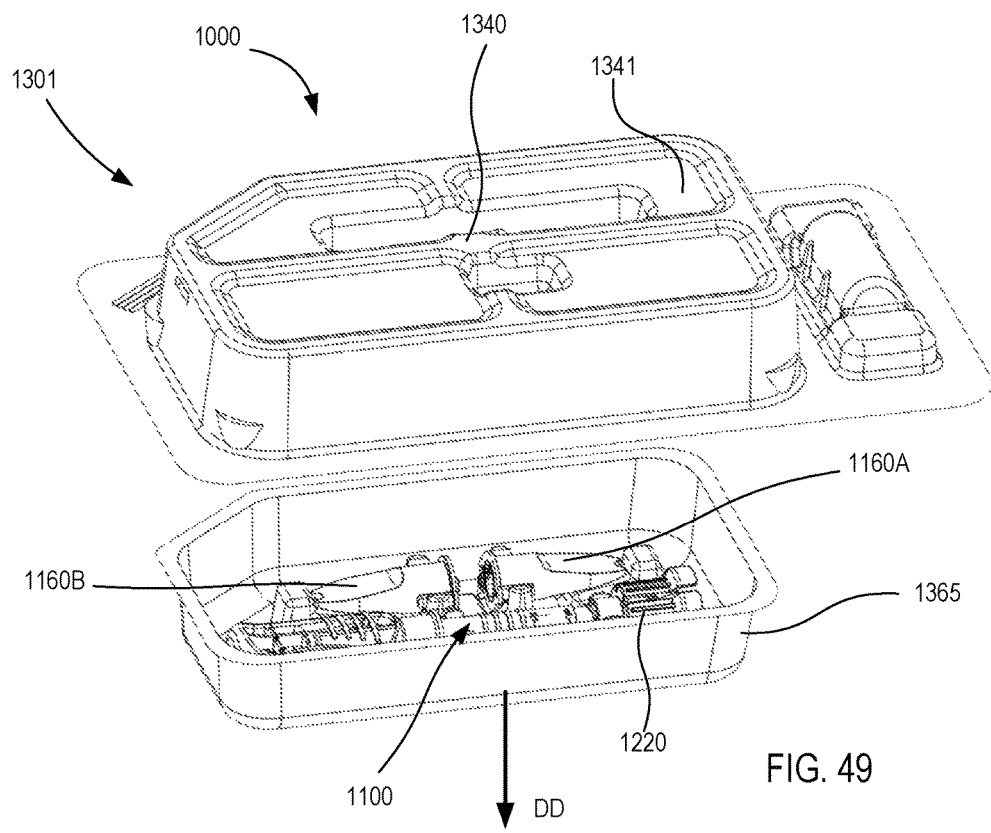

The inner (or second) tray 1365 is then released from within the first volume 1347 of the outer tray 1340 to place the second tray 1365 on the sterile surface, at 16. When the second tray 1365 is released, the kit is in a fifth configuration. This operation is shown in FIG. 49, which shows the inner tray 1365 being released from the outer tray 1340 by the arrow DD. As shown, the inner tray 1365, is in the upright position so that the injector assembly 1100, the needle assemblies 1160A, 1160B, and the vial adapter 1220 can be accessed after the inner tray 1365 is released. Similarly stated, the inner tray 1365 is released such that an opening defined by the inner tray 1365 and providing access to the volume 1370 is facing opposite the sterile surface (not shown in FIG. 49). Moreover, the first injector retention portion 1372A and the second injector retention portion 1372B maintain the injector 1100 in a fixed position second tray 1365. The first needle retention portion 1376A and the second needle retention portion 1376B maintain the first needle assembly 1160A and the second needle assembly 1160B, respectively, in a fixed position second tray 1365.

Figure 48:
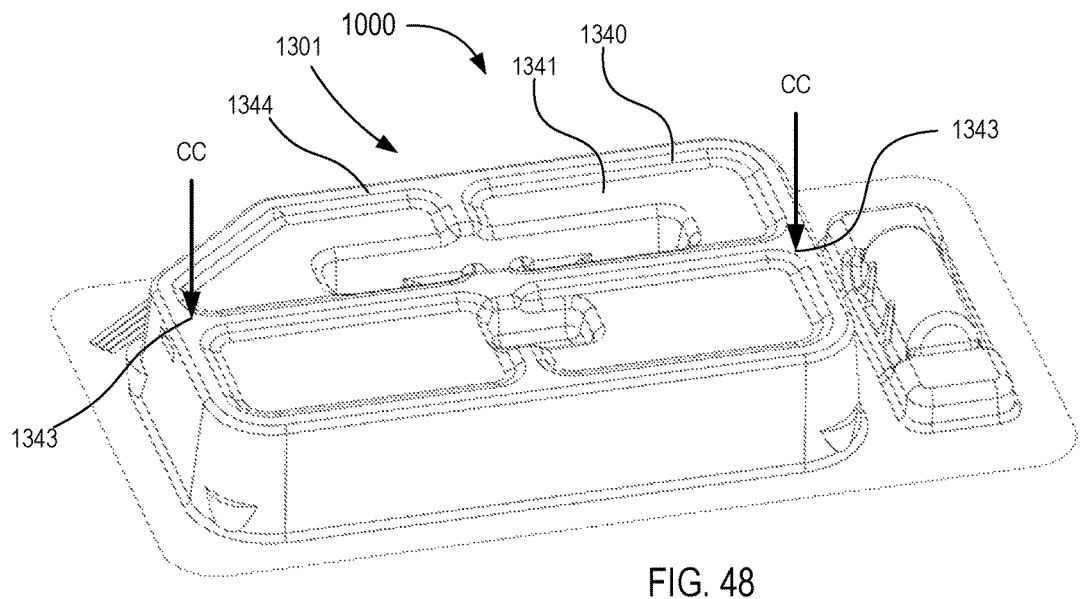
FIGS. 48 and 49 are side perspective views of the kit shown in FIGS. 13 and 14 being transitioned from the second configuration to a third configuration.

In some embodiments, the inner tray 1365 is released by applying a force against an actuation portion 1343 on the outer surface 1341 of the outer tray 1340, as shown by the arrows CC in FIG. 48. More particularly, in some embodiments, the second tray 1365 can include a raised portion 1344 that includes one or more actuation portions 1343 against which pressure will deform the outer tray 1340 sufficiently to release the flange 1380 of the inner tray 1365 from the retention protrusions 1349A, 1349B, thereby allowing the inner tray 1365 to drop down to the sterile surface. Moreover, as shown in FIG. 45 and described above, the inner tray 1365 can include one or more vent openings (e.g., openings 1381, 1382) that limit the creation of a vacuum within the volume 1370 that may otherwise retain the inner tray 1365 within the outer tray 1340.

Referring to FIGS. 22 and 23, the desired dosage from the drug vial 1200 can be transferred into the injector assembly 1100 by coupling the vial adapter 1220 to the barrel 1130 and the vial 1200. In some embodiments, the vial adapter 1220 can be pre-coupled to the injector assembly 1100 within the kit 1000. The coupling of the vial adapter 1220 to the barrel 1130 and/or the vial 1200 can be facilitated by the ridges (or gripping surfaces) 1240. When the vial adapter 1220 is coupled to the vial, the puncture member 1226 places the vial 1200 in fluid communication with the barrel 1130. With the barrel 1130 in fluid communication with the vial 1200, the user can manipulate the injector 1100 by moving the handle 1110 relative to the barrel 1130 in the proximal direction, as shown by the arrow BB in FIG. 23. This, in turn, moves the piston within the barrel 1130 in the proximal direction to draw in a portion of the medicament from the vial 1200.

The dose preparation operation can be performed above and/or within the sterile inner tray 1365. The side wall 1371 of the inner tray 1365 enhances the preservation of the sterile field by providing a physical barrier that prevents the inadvertent encroachment of non-sterile objects into the field and/or the movement of the sterile objects (e.g., a needle assembly 1160A) from moving outside of the sterile field. Similarly stated, the wall 1371 of the inner tray 1365 includes the outer surface 1366 and a lateral portion that extends from and surrounds the outer surface 1366. The lateral portion provides a barrier to preserve the integrity of the second volume 1370.

With the desired amount of drug formulation contained in the barrel 1130, the user can, for example, decouple the barrel 1130 from the vial adapter 1220 by rotating or "unscrewing" the vial adapter 1220. The user can manipulate the injector 1100 to couple the desired needle assembly 1160A, 1160B to the distal end portion 1132 of the barrel 1130, thereby placing the microneedle 1166 in fluid communication with the barrel 1130. With the needle assembly 1160A coupled to the barrel 1130, the user can remove the cap 1170 and proceed with the ocular injection. The ocular injection can be performed according to any suitable method, such as the methods shown and described in International Patent Application No. WO2015/19584, entitled "METHODS AND DEVICES FOR TREATING POSTERIOR OCULAR DISORDERS" and U.S. Pat. No. 9,180,047, entitled "APPARATUS AND METHODS FOR OCULAR INJECTION," each of which is incorporated herein by reference in its entirety.

Although the method 10 is shown and described as being performed with an injector, in other embodiments, a method can include preparing any medicament delivery device (such as the device 1100, 2100, and 3100) shown and described herein. Such preparation can include removal of the device and a medicament container from a packaging assembly in a manner that preserves a sterile field. Such preparation can also include preparing a dose of medicament (e.g., by transferring or conveying a predetermined amount of medicament from a container into the medicament delivery device). In some embodiments, a method includes preparing an injector assembly, such as the injector assembly 1100. Such methods can include, for example, establishing and maintaining a sterile field, and positioning the components within the sterile field in a manner that limits the likelihood of contamination or other compromise of the sterile field. FIG. 51 is a flow chart of a method 20 of preparing a medicament delivery device and/or drug product according to an embodiment, and is described in conjunction with the kit 1000 shown and described above. In other embodiments, however, the method 20 can be performed in conjunction with any suitable kit and/or medicament delivery device. The method 20 optionally includes removing the tray assembly 1301 is from within the sleeve 1310 to move the kit from a first (or storage) configuration to a second configuration, at 22. This operation is shown in by the arrow AA in FIG. 15. The tray assembly 1301 includes the medicament delivery device (e.g., the injector 1100). As described above, the tray assembly includes a first tray member and a second tray member. The first tray member defines a first volume and an opening providing access to the first volume. The second tray member defines a second volume within which the medicament delivery device is retained. The second tray member is coupled within first volume such that a wall of the second tray member and a wall of the first tray member enclose the medicament delivery device. In this manner the first volume and the medicament delivery device can be sterile.

In some embodiments, the method optionally includes removing a cover member (e.g., the cover member 1390, 2390, 3390) from the tray assembly from about the first volume, at 23. In some embodiments, this operation can be performed by peeling a peel portion (e.g., the peel portion 1399) of the cover from about the peel protrusions of the first tray. In other embodiments, the cover member can be removed by tearing or severing a portion of the cover member. Removal of the cover member exposes the first volume of the first tray (e.g., the tray 1340), which is within the sterile portion of the kit.

The method includes orienting the tray assembly such that the opening defined by the outer (or first) tray (e.g., the first tray 1340, 2340) is spaced apart from and facing downward towards a sterile surface, at 24. In this manner, the non-sterile, outer portions of the outer (or first) tray do not contact the sterile surface, thereby maintaining the integrity of the sterile field established for the injection procedure. Examples of this operation are shown in FIG. 7, which shows the assembly 2300 being inverted toward the work surface 2410, and FIG. 48, which shows the tray assembly 1301 being inverted.

The inner (or second) tray (e.g., the tray 1365) is then released from within the first volume of the outer tray (e.g., the tray 1340) to place the second tray on the sterile surface, at 26. This operation is shown in FIG. 8, which shows the second tray 2365 being released from the first tray 2340 by the arrow FF. Another example of this operation is shown in FIG. 49, which shows the inner tray 1365 being released from the outer tray 1340 by the arrow DD. As shown, the inner tray is in the upright position so that an opening defined by the inner (or second) tray and providing access to the by the inner (or second) tray is facing opposite the sterile surface. Moreover, a retainer of the second tray member maintains the medicament delivery device in a fixed position. In some embodiments, the inner (or second) tray is released by applying a force against an actuation portion (e.g., the actuation portion 1343) on the outer surface (e.g., the outer surface 1341) of the outer tray (see, e.g., the arrows CC in FIG. 48).

In some embodiments, the method optionally includes removing a medicament container (e.g., the drug vial 1200) from a container volume defined by the first tray, at 31. This operation can be done at any point in the method, and need not be performed after the second tray member is released from the first tray member. In some embodiments, the medicament container can be oriented and/or positioned within the first tray such that a frangible seal (or septum) is facing upwards for easy access.

In some embodiments, the kit can include an adapter, such as the vial adapter 1220. Further, in some embodiments, the adapter can be stored within the kit coupled to the medicament delivery device. In such embodiments, the method optionally includes coupling, after the releasing the second tray member, the medicament delivery device to the medicament container via the adapter, at 32. The method can also optionally include actuating the medicament delivery device to withdraw a dose of the medicament from the medicament container into the reservoir of the medicament delivery device, at 33. The dose preparation operations can be performed using the vial adapter 1220 as described above with reference to the method 10.

With the desired amount of drug formulation contained in the reservoir of the medicament delivery device, the user can, for example, decouple the medicament delivery device from the adapter (e.g., the vial adapter 1220). The user can manipulate the medicament delivery device within the sterile field to couple the desired delivery member (e.g., needle assembly 1160A, 1160B) to the device. The user can the perform any suitable method to deliver the medicament. Such methods can include, for example, the ocular injection methods shown and described in International Patent Application No. WO2015/19584, entitled "METHODS AND DEVICES FOR TREATING POSTERIOR OCULAR DISORDERS" and U.S. Pat. No. 9,180,047, entitled "APPARATUS AND METHODS FOR OCULAR INJECTION," each of which is incorporated herein by reference in its entirety.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although the kit 1000 is shown and described as including two needle assemblies, in other embodiments, a kit (or methods of use) can include or employ any number of delivery members. For example, in some embodiments, a kit can include a single needle assembly. In other embodiments, a kit can include one or more nasal delivery members or oral delivery members.

For example, although the sleeve 1310 is shown as maintaining a rectangular shape during removal of the tray assembly therefrom, in other embodiments the sleeve 1310 can include perforations, stress concentration risers and the like to facilitate tearing of the sleeve 1310 to access the tray assembly.

Although the sleeve 1310 is shown as having an opening on each through which the tray assembly can be inserted or removed from the volume 1312, in other embodiments, the sleeve can have one or both ends closed.

Although the sleeve 1310 is shown as including various instructions, markings and indicia, in other embodiments, any portion of the kit 1100 can include any suitable markings, instructions and/or indicia. For example, in some embodiments either (or both) of the inner tray 1365 and the outer tray 1340 can include indicia, such as pad printing of lettering, diagrams, pictures, or the like. For example, in some embodiments, an indicium can be formed on either (or both) of the inner tray 1365 and the outer tray 1340 via the tray tooling.

Although the indicia are described above as including identification, manufacturing information, and instructions, any of the indicia or labels described herein can include any suitable information, such as instructions, warnings, cautions or the like.

Any of the tray assembly components described herein, such as the outer tray 1340 and the inner tray 1365 can be formed or constructed of one or more materials suitable for sterilization and/or containing sterilized components. Examples of materials include metal foils, ceramics, or polymers. The polymer may be biodegradable or non-biodegradable. Examples of suitable biodegradable polymers include polylactides, polyglycolides, polylactide-coglycolides (PLGA), polyanhydrides, polyorthoesters, polyetheresters, polycaprolactones, polyesteramides, poly(butyric acid), poly(valeric acid), polyurethanes and copolymers and blends thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

In some embodiments, either (or both) of the inner tray 1365 and the outer tray 1340 can be thermoformed, and can be constructed of styrene or LDPE.

A wide range of ocular diseases and disorders may be treated by the methods and with the kits described herein. Non-limiting examples of such ocular diseases include uveitis, glaucoma, diabetic macular edema or retinopathy, macular degeneration, retinoblastoma, and genetic diseases. The methods described herein are particularly useful for the local delivery of drugs that need to be administered to the posterior region of the eye, for example the retinochoroidal tissue, macula, and optic nerve in the posterior segment of the eye. In one embodiment, the delivery methods and devices described herein may be used in gene-based therapy applications. For example, the methods may administer a fluid drug formulation into the suprachoroidal space to deliver select DNA, RNA, or oligonucleotides to targeted ocular tissues.

Any of the medicament containers (e.g., vials) and/or kits shown and described herein can include and/or be used with any suitable drug, medicament or therapeutic agent of the types mentioned herein. As used herein, the term "drug" refers to any prophylactic, therapeutic, or diagnostic agent (e.g., a contrast agent). The drug may be selected from suitable proteins, peptides and fragments thereof, which can be naturally occurring, synthesized or recombinantly produced. Representative examples of types of drugs for delivery to ocular tissues include antibodies, anti-viral agents, chemotherapeutic agents (e.g., topoisomerase inhibitors), analgesics, anesthetics, aptamers, antihistamines, anti-inflammatory agents, and anti-neoplastic agents. In one embodiment, the drug is triamcinolone or triamcinolone acetonide.

The term "antibody" is intended to refer broadly to any immunologic binding agent such as IgG, IgM, IgA, IgD and IgE. An antibody can be monoclonal or polyclonal, and in one embodiment, is a humanized antibody. The term "antibody" is also used to refer to any antibody-like molecule that has an antigen binding region, and includes antibody fragments such as Fab', Fab, F(ab')2, single domain antibodies (DABs), Fv, scFv (single chain Fv), and engineering multivalent antibody fragments such as dibodies, tribodies and multibodies. The techniques for preparing and using various antibody-based constructs and fragments are well known in the art (see, e.g., Antibodies: A Laboratory Manual, Cold Spring Harbor Laboratory, 1988; incorporated herein by reference).

Non-limiting examples of specific drugs and classes of drugs include β-adrenoceptor antagonists (e.g., carteolol, cetamolol, betaxolol, levobunolol, metipranolol, timolol), miotics (e.g., pilocarpine, carbachol, physostigmine), sympathomimetics (e.g., adrenaline, dipivefrine), carbonic anhydrase inhibitors (e.g., acetazolamide, dorzolamide), topoisomerase inhibitors (e.g., topotecan, irinotecan, camptothecin, lamellarin D, etoposide, teniposide, doxorubicin, mitoxantrone, amsacrine), prostaglandins, anti-microbial compounds, including anti-bacterials and anti-fungals (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines), anti-viral compounds (e.g., acyclovir, cidofovir, idoxuridine, interferons), aldose reductase inhibitors, anti-inflammatory and/or anti-allergy compounds (e.g., steroidal compounds such as betamethasone, clobetasone, dexamethasone, fluorometholone, hydrocortisone, prednisolone and non-steroidal compounds such as antazoline, bromfenac, diclofenac, indomethacin, lodoxamide, saprofen, sodium cromoglycate), artificial tear/dry eye therapies, local anesthetics (e.g., amethocaine, lignocaine, oxbuprocaine, proxymetacaine), cyclosporine, diclofenac, urogastrone and growth factors such as epidermal growth factor, mydriatics and cycloplegics, mitomycin C, and collagenase inhibitors and treatments of age-related macular degeneration such as pegagtanib sodium, ranibizumab, aflibercept and bevacizumab.

In some embodiments, a kit and/or vial includes an integrin antagonist, a selectin antagonist, an adhesion molecule antagonist (e.g., intercellular adhesion molecule (ICAM)-1, ICAM-2, ICAM-3, platelet endothelial adhesion molecule (PCAM), vascular cell adhesion molecule (VCAM)), a leukocyte adhesion-inducing cytokine or growth factor antagonist (e.g., tumor necrosis factor-α (TNF-α), interleukin-1β (IL-1β), monocyte chemotactic protein-1 (MCP-1), or a vascular endothelial growth factor (VEGF)). In some embodiments, a vascular endothelial growth factor (VEGF) inhibitor is included within a kit and/or administered with one of the microneedles described herein. In some embodiments, two drugs are included within a kit and/or are delivered by the methods described herein. The compounds may be administered in one formulation, or administered serially, in two separate formulations. For example, both a VEGF inhibitor and VEGF are provided. In some embodiments, the VEGF inhibitor is an antibody, for example a humanized monoclonal antibody. In further embodiments, the VEGF antibody is bevacizumab. In another embodiment, the VEGF inhibitor is ranibizumab, aflibercept or pegaptanib. In still other embodiments, the devices and methods described herein can be used to deliver one or more of the following VEGF antagonists: AL8326, 2C3 antibody, AT001 antibody, HyBEV, bevacizumab (Avastin), ANG3070, APX003 antibody, APX004 antibody, ponatinib (AP24534), BDM-E, VGX100 antibody (VGX100 CIRCADIAN), VGX200 (c-fos induced growth factor monoclonal antibody), VGX300, COSMIX, DLX903/1008 antibody, ENMD2076, Sutent (sunitinib malate), INDUS815C, R84 antibody, KD019, NM3, allogenic mesenchymal precursor cells combined with an anti-VEGF agent or antibody, MGCD265, MG516, VEGF-Receptor kinase inhibitors, MP0260, NT503, anti-DLL4/VEGF bispecific antibody, PAN90806, Palomid 529, BD0801 antibody, XV615, lucitanib (AL3810, E3810), AMG706 (motesanib diphosphate), AAV2-sFLT01, soluble FM receptor, Cediranib (Recentin), AV-951 (Tivozanib, KRN-951), Stivarga (regorafenib), Volasertib (BI6727), CEP11981, KH903, Lenvatinib (E7080), terameprocol (EM1421), ranibizumab (Lucentis), Votrient (pazopanib hydrochloride), PF00337210, PRS050, SPO1 (curcumin), Carboxyamidotriazole orotate, hydroxychloroquine, linifanib (ABT869, RG3635), Iluvien (fluocinolone acetonide), ALG1001, AGN150998, DARPin MP0112, AMG386, ponatinib (AP24534), AVA101, Vargatef (nintedanib), BMS690514, KH902, golvatinib (E7050), Afinitor (everolimus), Dovitinib lactate (TKI258, CHIR258), ORA101, ORA102, Axitinib (Inlyta, AG013736), Plitidepsin (Aplidin), Lenvatinib mesylate, PTC299, aflibercept (Zaltrap, Eylea), pegaptanib sodium (Macugen, LI900015), Visudyne (verteporfin), bucillamine (Rimatil, Lamin, Brimani, Lamit, Boomiq), R3 antibody, AT001/r84 antibody, troponin (BLS0597), EG3306, vatalanib (PTK787), Bmab100, GSK2136773, Anti-VEGFR Alterase, Avila, CEP7055, CLT009, ESBA903, HuMax-VEGF antibody, GW654652, HMPL010, GEM220, HYB676, JNJ17029259, TAK593, XtendVEGF antibody, Nova21012, Nova21013, CP564959, Smart Anti-VEGF antibody, AG028262, AG13958, CVX241, SU14813, PRS055, PG501, PG545, PTI101, TG100948, ICS283, XL647, enzastaurin hydrochloride (LY317615), BC194, quinolines, COT601M06.1, COT604M06.2, MabionVEGF, SIR-Spheres coupled to anti-VEGF or VEGF-R antibody, Apatinib (YN968D1), and AL3818. In addition, delivery of a VEGF inhibitor or VEGF antagonist using the microneedle devices and methods disclosed herein may be combined with one or more agents listed herein or with other agents known in the art.

In one embodiment, delivery of a VEGF antagonist to the suprachoroidal space of the eye using the kits, devices, and methods disclosed herein is used to treat, prevent and/or ameliorate a disease or disorder selected from leukemia, relapsed/refractory leukemia, acute lymphoblastic leukemia, Acute myelogenous leukemia, relapsed or refractory acute myeloid leukemia, atopic dermatitis, recurrent or metastatic carcinoma of the urothelium, advanced urothelial carcinoma, blood disorders, myelofibrosis, brain tumor, glioblastoma, glioma, meningioma, cancer, carcinomatous meningitis (neoplastic meningitis), choroidal neovascularization (CNV), subfoveal choroidal neovascularization, chronic lymphocytic leukemia, chronic myelogenous leukemia, refractory chronic myelogenous leukemia, colon cancer, colorectal cancer, degenerative nerve diseases, Neurodegenerative diseases, diabetic macular edema, visual Impairment due to diabetic macular edema, diabetic retinopathy, dry eye syndrome (inflammation and corneal tissue damage of dry Eye), endometrial cancer, eye diseases, ocular diseases, ocular neovascularization, eye cancer, Neurofibromatosis Type II, head and neck cancer, hematological malignancies, Kaposi's Sarcoma, Hepatocellular Carcinoma, Lung cancer, macular degeneration, age related macular degeneration, exudative age-related macular degeneration, neovascular (wet) age-related macular degeneration (AMD)), subfoveal Neovascular Age-Related macular degeneration, macular edema, macular edema associated with Branch Retinal Vein Occlusion, macular edema following retinal vein occlusion, macular edema with Retinal Vein Occlusion (RVO), multiple myeloma, relapsed or refractory multiple myeloma, multiple sclerosis, myopia, pathological myopia, neuroendocrine tumor, carcinoid tumor, neuroendocrine tumor, non-Hodgkin's Lymphoma, Diffuse Large B-Cell Lymphoma, Non-Small-Cell Lung cancer, Non-Squamous Non-Small-Cell Lung cancer, Non-small-cell-lung Adenocarcinoma, Squamous Non-Small-Cell Lung cancer, corneal graft rejection, osteoarthritis, recurrent symptomatic malignant ascites, peripheral T-cell lymphoma, androgen Independent Psoriasis, pulmonary Fibrosis, Idiopathic Pulmonary Fibrosis, respiratory diseases, retinal detachment, retinal disorders, retinitis pigmentosa, retinal vein occlusion, branch retinal vein occlusion, central retinal vein occlusion, rheumatoid arthritis, sarcoma, alveolar soft part sarcoma, soft tissue sarcoma, scleroderma/systemic sclerosis, solid tumors, refractory germ cell tumors, thyroid cancer, differentiated or medullar thyroid cancer, and West Syndrome (Infantile Spasm).

In certain embodiments, the drug delivered to the suprachoroidal space using the kits, devices, and methods disclosed herein is rapamycin (Sirolimus, Rapamune). In one embodiment, the devices (e.g., microneedle devices) and methods disclosed herein are used in conjunction with rapamycin to treat, prevent and/or ameliorate a wide range of diseases or disorders including, but not limited to: abdominal neoplasms, acquired immunodeficiency syndrome, acute coronary syndrome, acute lymphoblastic leukemia, acute myelocytic leukemia, acute non-lymphoblastic leukemia, adenocarcinoma, adenoma, adenomyoepithelioma, adnexal diseases, anaplastic astrocytoma, anaplastic large cell lymphoma, anaplastic plasmacytoma, anemia, angina pectoris, angioimmunoblastic lymphadenopathy with dysproteinemia, angiomyolipoma, arterial occlusive diseases, arteriosclerosis, astrocytoma, atherosclerosis, autoimmune diseases, B-cell lymphomas, blood coagulation disorders, blood protein disorders, bone cancer, bone marrow diseases, brain diseases, brain neoplasms, breast beoplasms, bronchial neoplasms, carcinoid syndrome, carcinoid Tumor, carcinoma, squamous cell carcinoma, central nervous system diseases, central nervous system neoplasms, choroid diseases, choroid plexus neoplasms, choroidal neovascularization, choroiditis, chronic lymphocytic leukemia, chronic myeloid leukemia, chronic myelomonocytic leukemia, chronic myeloproliferative disorders, chronic neutrophilic leukemia, clear cell renal cell carcinoma, colonic diseases, colonic neoplasms, colorectal neoplasms, coronary artery disease, coronary disease, coronary Occlusion, coronary restenosis, coronary stenosis, coronary thrombosis, cutaneous T-cell lymphoma, diabetes mellitus, digestive system neoplasms, dry eye syndromes, ear diseases, edema, endocrine gland neoplasms, endocrine system diseases, endometrial neoplasms, Endometrial stromal tumors, Ewing's sarcoma, exanthema, eye neoplasms, fibrosis, follicular lymphoma, gastrointestinal diseases, gastrointestinal neoplasms, genital neoplasms, glioblastoma, glioma, gliosarcoma, graft vs host disease, hematologic diseases, hematologic neoplasms, hemorrhagic disorders, hemostatic disorders, Hodgkin disease, Hodgkin lymphoma, homologous wasting disease, immunoblastic lymphadenopathy, immunologic deficiency syndromes, immunoproliferative disorders, infarction, inflammation, intestinal diseases, intestinal neoplasms, ischemia, kidney cancer, kidney diseases, kidney neoplasms, leukemia, B-Cell, leukemia, lymphoid, liver cancer, liver diseases, lung diseases, lymphatic diseases, lymphoblastic lymphoma, lymphoma, macular degeneration, macular edema, melanoma, mouth neoplasms, multiple myeloma, myelodysplastic syndromes, myelofibrosis, myeloproliferative disorders, neuroectodermal tumors, neuroendocrine tumors, neuroepithelioma, neurofibroma, renal cancer, respiratory tract diseases, retinal degeneration, retinal diseases, retinal neoplasms, retinoblastoma, rhabdomyosarcoma, thoracic neoplasms, uveitis, vascular diseases, Waldenstrom Macroglobulinemia, and wet macular degeneration. In addition, delivery of rapamycin using the microneedle devices and methods disclosed herein may be combined with one or more agents listed herein or with other agents known in the art.

In one embodiment, the drug delivered to ocular tissue, for example the sclera or suprachoroidal space, using the kits, microneedle devices, and methods disclosed herein reduces, inhibits, prevents and/or ameliorates inflammation. Examples of drugs that reduce, inhibit, prevent and/or ameliorate inflammation include (but are not limited to): 19AV Agonists, 19GJ agonists, 2MD Analogs, 4SC101, 4SC102, 57-57, 5-HT2 Receptor Antagonist, 64G12, A804598, A967079, AAD2004, AB1010, AB224050, abatacept, Abegrin, Abevac, AbGn134, AbGn168, Abki, ABN912, ABR215062, ABR224050, Abrammune, Abreva, ABS15, ABS4, ABS6, ABT122, ABT325, ABT494, ABT874, ABT963, ABXIL8, ABXRB2, AC430, Accenetra, Acdeam, ACE772, Acebid, Acebloc, aceclofenac, acetaminophen, chlorzoxazone, serrapeptase, tizanidine hydrochloride, betadex, Aceclogesic Plus, Aceclon, Acecloren, Aceclorism, acecrona, Aceffein, acemetacin, Acenac, Acenterine, Acetal-SP, ibuprofen, Acetyl-G, acetylsalicylate dl-lysine, acetylsalicylic acid, Acicot, Acifine, Acik, Aclocen, Acloflam-P, Aclomore, Aclon, A-CQ, ACS15, actarit, Actemra, Acthelea liofilizado, Actifast, Actimab-B, Actiquim, Actirin, Actis PLUS, activated leukocyte cell adhesion molecule antibody, Acular X, AD452, adalimumab, ADAMTS5 Inhibitor, ADC1001, Adco-Diclofenac, Adco-Indomethacin, Adco-Meloxicam, Adco-Naproxen, Adco-Piroxicam, Adcort, Adco-Sulindac, adenosine triphosphate disodium, AdenosineA2a Receptor Agonist, Adimod, Adinos, Adioct, Adiodol, Adipoplus, adipose derived stem and/or regenerative cells, Adizen, Adpep, Advacan, Advagraf, Advel, Adwiflam, AEB071, Aental, Afenac, Affen Plus, Afiancen, Afinitor, Aflamin, Aflazacort, Aflogen, Afloxan, AFM15, AFM16, AFM17, AFM23, Afpred-Dexa, AFX200, AG011, Agafen, aganirsen, AGI1096, Agidex, AGS010, Agudol, A-Hydrocort, AIK1, AIN457, Airtal, AIT110, AJM300, ajulemic acid, AK106, AL-24-2A1, AL4-1A1, Ala Cort, Alanz, Albumin immune-globulin, alclometasone dipropionate, ALD518, aldesleukin, Aldoderma, alefacept, alemtuzumab, Alequel, Alergolon, Alergosone, Aletraxon, Alfenac, Algason, Algin vek coat, Algioflex, Algirex, Algivin Plus, alicaforsen sodium, Alin, Alinia, Aliviodol, Aliviosin, alkaline phosphatase, ALKS6931, allantoin, All-bupen, Allmol, Allochrysine, allogeneic endothelial cells, allogeneic mesenchymal precursor cells, allogeneic mesenchymal stem cells, alminoprofen, alpha 1 antitrypsin, Alpha 7 nicotinic agonists, alpha amylase, alpha chymotrypsin, alpha fetoprotein, alpha linolenic acid, Alpha-1-antitrypsin, Alpha2BetA1 Integrin Inhibitors, Alphacort, Alphafen, alpha-hexidine, alpha-trypsin, Alphintern, Alpinamed mobility omega 3, Alpoxen, AL-Rev1, Alterase, ALX0061, ALX0761, ALXN1007, ALXN1102, AM3840, AM3876, AMAB, AMAP102, Amason, Ambene, AmbezimG, amcinonide, AME133v, Amecin, Ameloteks, A-Methapred, Amevive, AMG108, AMG139, AMG162, AMG181, AMG191, AMG220, AMG623, AMG674, AMG714, AMG719, AMG729, AMG827, Amidol, amifampridine phosphate, Amifenac, Amimethacin, amiprilose hydrochloride, Amiprofen, Ammophos, Amoflam, AMP110, Ampikyy, Ampion, ampiroxicam, amtolmetin guacil, AMX256, AN6415, ANA004, ANA506, Anabu, Anacen, Anaflam, Anaflex ACI, Anaida, anakinra, Analgen Artritis, Anapan, Anaprox, Anavan, Anax, Anco, andrographis, Aneol, Anergix, Anervax.RA, Anflene, ANG797, Anilixin, Anmerushin, Annexin 1 peptides, annexin A5, Anodyne, Ansaid, Anspirin, Antarene, Anti BST2 antibody, Anti C5a MAb, Anti ILT7 antibody, Anti VLA1 antibody, Anti-alpha 11 antibody, Anti-CD4 802-2, Anti-CD86 Monoclonal Antibody, Anti-chemokine, Anti-DC-SIGN, Anti-HMGB-1 MAb, Anti-IL-18 Mab, Anti-IL-1R MAb, Anti-IL-1R MAb, Anti-IL23 BRISTOL, Anti-inflammatory Peptides, Anti-interleukin 1Beta antibody, Anti-LIGHT antibody, Anti-LIGHT antibody, Anti-MIF Antibody, Anti-MIF Antibody, Anti-miR181a, antioxidant inflammation modulators, Antiphlamine, AntiRAGE MAb, antithrombin III, Anti-TIRC-7 MAb, Anusol-HC, Anyfen, AP105, AP1089, AP1189, AP401, AP501, apazone, APD334, Apentac, APG103, Apidone, apilimod mesylate, Apitac, Apitoxin, Apizel, APN Inhibitor, apo-Azathioprine, Apo-Dexamethasone, ApoE mimetics, ApoFasL, apo-Indomethacin, apo-mefenamic, apo-methotrexate, apo-nabumetone, Apo-Napro-NA, apo-Naproxen, aponidin, apo-Phenylbutazone, apo-Piroxicam, apo-Sulin, Apo-Tenoxicam, apo-Tiaprofenic, Apranax, apremilast, apricoxib, Aprofen, Aprose, Aproxen, APX001 antibody, APX007 antibody, APY0201, AqvoDex, AQX108, AQX1125, AQX131135, AQX140, AQX150, AQX200, AQX356, AQXMN100, AQXMN106, ARA290, Arava, Arcalyst, Arcoxia, Arechin, Arflur, ARG098, ARG301, arginine aescin, arginine deiminase (pegylated), ARGX109 antibody, ARGX110, Arheuma, Aristocort, Aristospan, Ark-AP, ARN4026, Arofen, Aroff EZ, Arolef, Arotal, Arpibru, Arpimune, Arpu Shuangxin, ARQ101, Arrestin SP, Arrox, ARRY162, ARRY371797, ARRY614, ARRY872, ART621, Artamin, Arthfree, Artho Tech, Arthrexin, Arthrispray, Arthrotec, Arthrovas, Artifit, Artigo, Artin, Artinor, Artisid, Artoflex, Artren Hipergel, Artridol, Artrilase, Artrocaptin, Artrodiet, Artrofen, Artropan, Artrosil, Artrosilene, Artrotin, Artrox, Artyflam, Arzerra, AS604850, AS605858, Asacol, ASA-Grindeks, Asazipam, Aseclo, ASF1096, ASF1096, ASK8007, ASKP1240, ASLAN003, Asmo ID, Asonep, ASP015K, ASP2408, ASP2409, Aspagin, Aspeol, Aspicam, Aspirimex, aspirin, AST120, astaxanthin, AstroCort, Aszes, AT002 antibody, AT007, AT008 antibody, AT008 antibody, AT010, AT1001, atacicept, Ataspin, Atepadene, Atgam, ATG-Fresenius, Athrofen, ATIO03, atiprimod, ATL1222, ATN103, ATN192, ATR107, Atri, Atrmin, Atrosab antibody, ATX3105, AU801, auranofin, Aurobin, Auropan, Aurothio, aurotioprol, autologous adipose derived regenerative cells, Autonec, Avandia, AVE9897, AVE9940, Avelox, Avent, AVI3378, Avloquin, AVP13546, AVP13748, AVP28225, AVX002, Axcel Diclofenac, Axcel Papain, Axen, AZ17, AZ175, Azacortid, AZA-DR, Azafrine, Azamun, Azanin, Azap, Azapin, Azapren, Azaprin, Azaram, Azasan, azathioprine, AZD0275, AZD0902, AZD2315, AZD5672, AZD6703, AZD7140, AZD8309, AZD8566, AZD9056, Azet, Azintrel, azithromycin, Az-od, Azofit, Azolid, Azoran, Azulene, Azulfidine, Azulfin, B1 antagonists, Baclonet, BAF312, BAFF Inhibitor, Bages, Baily S.P., Baleston, Balsolone, baminercept alfa, bardoxolone methyl, baricitinib, Barotase, Basecam, basiliximab, Baxmune, Baxo, BAY869766, BB2827, BCX34, BCX4208, Becfine, Beclate-C, Beclate-N, Beclolab Q, beclomethasone dipropionate, Beclorhin, Becmet-CG, Begita, Begti, belatacept, belimumab, Belosalic, Bemetson, Ben, Benevat, Benexam, Benflogin, Benisan, Benlysta, Benlysta, benorilate, Benoson, benoxaprofen, Bentol, benzydamine hydrochloride, Benzymin, Beofenac, Berafen, Berinert, Berlofen, Bertanel, Bestamine, Bestofen, Beta Nicip, Betacort, Betacorten G, Betafoam, beta-glucan, Betalar, Beta-M, Betamed, Betamesol, betamethasone, betamethasone dipropionate, betamethasone sodium, betamethasone sodium phosphate, betamethasone valerate, Betane, Betanex, Betapanthen, Betapar, Betapred, Betason, Betasonate, Betasone, Betatrinta, Betaval, Betazon, Betazone, Betesil, Betnecort, Betnesol, Betnovate, Bextra, BFPC13, BFPC18, BFPC21, BFPT6864, BG12, BG9924, BI695500, BI695501, BIA12, Big-Joint-D, BIIB023 antibody, Bi-ksikam, Bingo, BioBee, Bio-Cartilage, Bio-C-Sinkki, Biodexone, Biofenac, Bioreucam, Biosone, Biosporin, BIRB796, Bitnoval, Bitvio, Bivigam, BKT140, BKTP46, BL2030, BL3030, BL4020, BL6040, BL7060, BLI1300, blisibimod, Blokium B12, Blokium Gesic, Blokium, BMS066, BMS345541, BMS470539, BMS561392, BMS566419, BMS582949, BMS587101, BMS817399, BMS936557, BMS945429, BMS-A, BN006, BN007, BNP166, Bonacort, Bonas, bone marrow stromal cell antigen 2 antibody, Bonflex, Bonifen, Boomiq, Borbit, Bosong, BRO2001, BR3-FC, Bradykinin B1 Receptor Antagonist, Bredinin, Brexecam, Brexin, Brexodin, briakinumab, Brimani, briobacept, Bristaflam, Britten, Broben, brodalumab, Broen-C, bromelains, Bromelin, Bronax, Bropain, Brosiral, Bruace, Brufadol, Brufen, Brugel, Brukil, Brusil, BT061, BTI9, BTK kinase inhibitors, BTT1023 antibody, BTT1507, bucillamine, Bucillate, Buco Reigis, bucolome, Budenofalk, budesonide, Budex, Bufect, Bufencon, Bukwang Ketoprofen, Bunide, Bunofen, Busilvex, busulfan, Busulfex, Busulipo, Butartrol, Butarut B12, Butasona, Butazolidin, Butesone, Butidiona, BVX10, BXL628, BYM338, B-Zone, C1 esterase inhibitor, C243, c4462, c5997, C5aQb, c7198, c9101, C9709, c9787, CAB101, cadherin 11 antibody, caerulomycin A, CAL263, Calcort, Calmatel, CAM3001, Camelid Antibodies, Camlox, Camola, Campath, Camrox, Camtenam, canakinumab, *candida albicans* antigen, Candin, cannabidiol, CAP1.1, CAP1.2, CAP2.1, CAP2.2, CAP3.1, CAP3.2, Careram, Carimune, Cariodent, Cartifix, CartiJoint, Cartilago, Cartisafe-DN, Cartishine, Cartivit, Cartril-S, Carudol, CaspaCIDe, CaspaCIDe, Casyn, CAT1004, CAT1902, CAT2200, Cataflam, Cathepsin S inhibitor, Catlep, CB0114, CB2 agonist, CC0478765, CC10004, CC10015, CC1088, CC11050, CC13097, CC15965, CC16057, CC220, CC292, CC401, CC5048, CC509, CC7085, CC930, CCR1 Antagonist, CCR6 Inhibitor, CCR7 Antagonist, CCRL2 antagonist, CCX025, CCX354, CCX634, CD Diclofenac, CD102, CD103 Antibody, CD103 Antibody, CD137 antibody, CD16 antibody, CD18 antibody, CD19 antibody, CD1d Antibody, CD20 antibody, CD200Fc, CD209 antibody, CD24, CD3 antibody, CD30 antibody, CD32A antibody, CD32B antibody, CD4 antibody, CD40 ligand, CD44 antibody, CD64 antibody, CDC839, CDC998, CDIM4, CDIM9, CDK9-Inhibitor, CDP146, CDP323, CDP484, CDP6038, CDP870, CDX1135, CDX301, CE224535, Ceanel, Cebedex, Cebutid, Ceclonac, Ceex, CEL2000, Celact, Celbexx, Celcox, Celebiox, Celebrex, Celebrin, Celecox, celecoxib, Celedol, Celestone, Celevex, Celex, CELG4, Cell adhesion molecule antagonists, CellCept, Cellmune, Celosti, Celoxib, Celprot, Celudex, cenicriviroc mesylate, cenplacel-1, CEP11004, CEP37247, CEP37248, Cephyr, Ceprofen, Certican, certolizumab pegol, Cetofenid, Cetoprofeno, cetylpyridinium chloride, CF101, CF402, CF502, CG57008, CGEN15001, CGEN15021, CGEN15051, CGEN15091, CGEN25017, CGEN25068, CGEN40, CGEN54, CGEN768, CGEN855, CGI1746, CGI560, CGI676, Cgtx-Peptides, CH1504, CH4051, CH4446, chaperonin 10, chemokine C—C motif ligand 2, chemokine C—C motif ligand 2 antibody, chemokine C—C motif ligand 5 antibody, chemokine C—C motif receptor 2 antibody, chemokine C—C motif receptor 4 antibody, chemokine C—X—C motif ligand 10 antibody, chemokine C—X—C motif ligand 12 aptamer, Chemotaxis Inhibitor, Chillmetacin, chitinase 3-like 1, Chlocodemin, Chloquin, chlorhexidine gluconate, chloroquine phosphate, choline magnesium trisalicylate, chondroitin sulfate, Chondroscart, CHR3620, CHR4432, CHR5154, Chrysalin, Chuanxinlian, Chymapra, Chymotase, chymotrypsin, Chytmutrip, CI202, CI302, Cicloderm-C, Ciclopren, Cicporal, Cilamin, Cimzia, cinchophen, cinmetacin, cinnoxicam, Cinoderm, Cinolone-S, Cinryze, Cipcorlin, cipemastat, Cipol-N, Cipridanol, Cipzen, Citax F, Citogan, Citoken T, Civamide, CJ042794, CJ14877, c-Kit monoclonal antibody, cladribine, Clafen, Clanza, Claversal, clazakizumab, Clearoid, Clease, Clevegen, Clevian, Clidol, Clindac, Clinoril, Cliptol, Clobenate, Clobequad, clobetasol butyrate, clobetasol propionate, Clodol, clofarabine, Clofen, Clofenal LP, Clolar, Clonac, Clongamma, clonixin lysine, Clotasoce, Clovacort, Clovana, Cloxin, CLT001, CLT008, C-MAF Inhibitor, CMPX1023, Cnac, CNDO201, CNI1493, CNTO136, CNTO148, CNT01959, Cobefen, CoBenCoDerm, Cobix, Cofenac, Cofenac, COG241, COL179, colchicine, Colchicum Dispert, Colchimax, Colcibra, Coledes A, Colesol, Colifoam, Colirest, collagen, type V, Comcort, complement component (3b/4b) receptor 1, Complement Component C1s Inhibitors, complement component C3, complement factor 5a receptor antibody, complement factor 5a receptor antibody, complement factor D antibody, Condrosulf, Condrotec, Condrothin, conestat alfa, connective tissue growth factor antibody, Coolpan, Copaxone, Copiron, Cordefla, Corhydron, Cort S, Cortan, Cortate, Cort-Dome, Cortecetine, Cortef, Corteroid, Corticap, Corticas, Cortic-DS, corticotropin, Cortiderm, Cortidex, Cortiflam, Cortinet M, Cortinil, Cortipyren B, Cortiran, Cortis, Cortisolu, cortisone acetate, Cortival, Cortone acetate, Cortopin, Cortoral, Cortril, Cortypiren, Cosamine, Cosone, cosyntropin, COT Kinase Inhibitor, Cotilam, Cotrisone, Cotson, Covox, Cox B, COX-2/5-LO Inhibitors, Coxeton, Coxflam, Coxicam, Coxitor, Coxtral, Coxypar, CP195543, CP412245, CP424174, CP461, CP629933, CP690550, CP751871, CPSI2364, C-quin, CR039, CR074, CR106, CRA102, CRAC channel inhibitor, CRACM Ion Channel Inhibitor, Cratisone, CRB15, CRC4273, CRC4342, C-reactive protein 2-methoxyethyl phosphorothioate oligonucleotide, CreaVax-RA, CRH modulators, critic-aid, Crocam, Crohnsvax, Cromoglycic acid, cromolyn sodium, Cronocorteroid, Cronodicasone, CRTX803, CRx119, CRx139, CRx150, CS502, CS670, CS706, CSF1R Kinase Inhibitors, CSL324, CSL718, CSL742, CT112, CT1501R, CT200, CT2008, CT2009, CT3, CT335, CT340, CT5357, CT637, CTP05, CTP10, CT-P13, CTP17, Cuprenil, Cuprimine, Cuprindo, Cupripen, Curaquin, Cutfen, CWF0808, CWP271, CX1020, CX1030, CX1040, CX5011, Cx611, Cx621, Cx911, CXC chemokine receptor 4 antibody, CXCL13 antibodies, CXCR3 antagonists, CXCR4 antagonist, Cyathus 1104 B, Cyclo-2, Cyclocort, cyclooxygenase-2 inhibitor, cyclophosphamide, Cyclorine, Cyclosporin A Prodrug, Cyclosporin analogue A, cyclosporine, Cyrevia, Cyrin CLARIS, CYT007TNFQb, CYT013IL1bQb, CYT015IL17Qb, CYT020TNFQb, CYT107, CYT387, CYT99007, cytokine inhibitors, Cytopan, Cytoreg, CZC24832, D1927, D9421C, daclizumab, danazol, Danilase, Dantes, Danzen, dapsone, Dase-D, Daypro, Daypro Alta, Dayrun, Dazen, DB295, DBTP2, D-Cort, DD1, DD3, DE096, DE098, Debio0406, Debio0512, Debio0615, Debio0618, Debio1036, Decaderm, Decadrale, Decadron, Decadronal, Decalon, Decan, Decason, Decdan, Decilone, Declophen, Decopen, Decorex, Decorten, Dedema, Dedron, Deexa, Defcort, De-flam, Deflamat, Deflan, Deflanil, Deflaren, Deflaz, deflazacort, Defnac, Defnalone, Defnil, Defosalic, Defsure, Defza, Dehydrocortison, Dekort, Delagil, delcasertib, delmitide, Delphicort, Deltacorsolone, Deltacortril, Deltafluorene, Deltasolone, Deltasone, Deltastab, Deltonin, Demarin, Demisone, Denebola, denileukin diftitox, denosumab, Denzo, Depocortin, Depo-medrol, Depomethotrexate, Depopred, Deposet, Depyrin, Derinase, Dermol, Dermolar, Dermonate, Dermosone, Dersone, Desketo, desonide, desoxycorticosterone acetate, Deswon, Dexa, Dexabene, Dexacip, Dexacort, Dexacortisone, Dexacotisil, Dexadic, Dexadrin, Dexadron, Dexafar, Dexahil, Dexalab, Dexalaf, Dexalet, Dexalgen, Dexallion, Dexalocal, Dexalone, Dexa-M, Dexamecortin, Dexamed, Dexamedis, Dexameral, Dexameta, Dexamethasone, dexamethasone acetate, dexamethasone palmitate, dexamethasone phosphate, dexamethasone sodium metasulfobenzoate, dexamethasone sodium phosphate, Dexamine, Dexapanthen, Dexa-S, Dexason, Dexatab, Dexatopic, Dexaval, Dexaven, Dexazolidin, Dexazona, Dexazone, Dexcor, Dexibu, dexibuprofen, Dexico, Dexifen, Deximune, dexketoprofen, dexketoprofen trometamol, Dexmark, Dexomet, Dexon I, Dexonalin, Dexonex, Dexony, Dexoptifen, Dexpin, Dextan-Plus, dextran sulfate, Dezacor, Dfz, diacerein, Diannexin, Diastone, Dicarol, Dicasone, Dicknol, Diclo, Diclobon, Diclobonse, Diclobonzox, Diclofast, Diclofen, diclofenac, diclofenac beta-dimethylaminoethanol, diclofenac deanol, diclofenac diethylamine, diclofenac epolamine, diclofenac potassium, diclofenac resinate, diclofenac sodium, Diclogen AGIO, Diclogen Plus, Diclokim, Diclomed, Diclo-NA, Diclonac, Dicloramin, Dicloran, Dicloreum, Diclorism, Diclotec, Diclovit, Diclowal, Diclozem, Dico P, Dicofen, Dicoliv, Dicorsone, Dicron, Dicser, Difena, Diffutab, diflunisal, dilmapimod, Dilora, dimethyl sulfone, Dinac, D-Indomethacin, Dioxaflex Protect, Dipagesic, Dipenopen, Dipexin, Dipro AS, Diprobeta, Diprobetasone, Diproklenat, Dipromet, Dipronova, Diprosone, Diprovate, Diproxen, Disarmin, Diser, Disopain, Dispain, Dispercam, Distamine, Dizox, DLT303, DLT404, DM199, DM99, DMI9523, dnaJP1, DNX02070, DNX04042, DNX2000, DNX4000, docosanol, Docz-6, Dolamide, Dolaren, Dolchis, Dolex, Dolflam, Dolfre, Dolgit, Dolmax, Dolmina, Dolo Ketazon, Dolobest, Dolobid, Doloc, Dolocam, Dolocartigen, Doloflt, Dolokind, Dolomed, Dolonac, Dolonex, Dolotren, Dolozen, Dolquine, Dom0100, Dom0400, Dom0800, Domet, Dometon, Dominadol, Dongipap, Donica, Dontisanin, doramapimod, Dorixina Relax, Dormelox, Dorzine Plus, Doxatar, Doxtran, DP NEC, DP4577, DP50, DP6221, D-Penamine, DPIV/APN Inhibitors, DR1 Inhibitors, DR4 Inhibitors, DRA161, DRA162, Drenex, DRF4848, DRL15725, Drossadin, DSP, Duexis, Duo-Decadron, Duoflex, Duonase, DV1079, DV1179, DWJ425, DWP422, Dymol, DYN15, Dynapar, Dysmen, E5090, E6070, Easy Dayz, Ebetrexat, EBI007, ECO286, EC0565, EC0746, Ecax, *echinacea purpurea* extract, EC-Naprosyn, Econac, Ecosprin 300, Ecosprin 300, Ecridoxan, eculizumab, Edecam, efalizumab, Efcortesol, Effigel, Eflagen, Efridol, EGFR Antibody, EGS21, eIF5A1 siRNA, Ekarzin, elafin, Eldoflam, Elidel, Eliflam, Elisone, Elmes, Elmetacin, ELND001, ELND004, elocalcitol, Elocom, elsibucol, Emanzen, Emcort, Emifen, Emifenac, emorfazone, Empynase, emricasan, Emtor, Enable, Enbrel, Enceid, EncorStat, Encortolon, Encorton, Endase, Endogesic, Endoxan, Enkorten, Ensera, Entocort, Enzylan, Epanova, Eparang, Epatec, Epicotil, epidermal growth factor receptor 2 antibody, epidermal growth factor receptor antibody, Epidixone, Epidron, Epiklin, EPPA1, epratuzumab, EquiO, Erac, Erazon, ERB041, ERB196, Erdon, EryDex, *escherichia coli* enterotoxin B subunit, Escin, E-Selectin Antagonists, Esfenac, ESN603, esonarimod, Esprofen, estetrol, Estopein, Estrogen Receptor beta agonist, etanercept, etaracizumab, ETC001, ethanol propolis extract, ETI511, etiprednol dicloacetate, Etodin, Etodine, Etodol, etodolac, Etody, etofenamate, Etol Fort, Etolac, Etopin, etoricoxib, Etorix, Etosafe, Etova, Etozox, Etura, Eucob, Eufans, eukaryotic translation initiation factor 5A oligonucleotide, Eunac, Eurocox, Eurogesic, everolimus, Evinopon, EVT401, Exaflam, EXEL9953, Exicort, Expen, Extra Feverlet, Extrapan, Extrauma, Exudase, F16, F991, Falcam, Falcol, Falzy, Farbovil, Farcomethacin, Farnerate, Farnezone, Farnezone, Farotrin, fas antibody, Fastflam, FasTRACK, Fastum, Fauldmetro, FcgammaR1A antibody, FE301, Febrofen, Febrofld, felbinac, Feldene, Feldex, Feloran, Felxicam, Fenac, Fenacop, Fenadol, Fenaflan, Fenamic, Fenaren, Fenaton, Fenbid, fenbufen, Fengshi Gutong, Fenicort, Fenopine, fenoprofen calcium, Fenopron, Fenris, Fensupp, Fenxicam, fepradinol, Ferovisc, Feverlet, fezakinumab, FG3019, FHT401, FHTCT4, FID114657, figitumumab, Filexi, filgrastim, Fillase, Final, Findoxin, fingolimod hydrochloride, firategrast, Firdapse, Fisiodar, Fivasa, FK778, Flacoxto, Fladalgin, Flagon, Flamar, Flamcid, Flamfort, Flamide, Flaminase, Flamirex Gesic, Flanid, Flanzen, Flaren, Flaren, Flash Act, Flavonoid Anti-inflammatory Molecule, Flebogamma DIF, Flenac, Flex, Flexafen 400, Flexi, Flexidol, Flexium, Flexon, Flexono, Flogene, Flogiatrin B12, Flogomin, Flogoral, Flogosan, Flogoter, Flo-Pred, Flosteron, Flotrip Forte, Flt3 inhibitors, fluasterone, Flucam, Flucinar, fludrocortisone acetate, flufenamate aluminum, flumethasone, Flumidon, flunixin, fluocinolone, fluocinolone acetonide, fluocinonide, fluocortolone, Fluonid, fluorometholone, Flur, flurbiprofen, Fluribec, Flurometholone, Flutal, fluticasone, fluticasone propionate, Flutizone, Fluzone, FM101 antibody, fms-related tyrosine kinase 1 antibody, Folitrax, fontolizumab, formic acid, Fortecortin, Fospeg, fostamatinib disodium, FP1069, FP13XX, FPA008, FPA031, FPT025, FR104, FR167653, Framebin, Frime, Froben, Frolix, FROUNT Inhibitors, Fubifen PAP, Fucole ibuprofen, Fulamotol, Fulpen, Fungifin, Furotalgin, fusidate sodium, FX002, FX141L, FX201, FX300, FX87L, Galectin modulators, gallium maltolate, Gamimune N, Gammagard, Gamma-I.V., GammaQuin, Gamma-Venin, Gamunex, Garzen, Gaspirin, Gattex, GBR500, GBR500 antibody, GBT009, G-CSF, GED0301, GED0414, Gefenec, Gelofen, Genepril, Gengraf, Genimune, Geniquin, Genotropin, Genz29155, Gerbin, Gerbin, gevokizumab, GF01564600, Gilenia, Gilenya, givinostat, GL0050, GL2045, glatiramer acetate, Globulin, Glortho Forte, Glovalox, Glovenin-I, GLPG0259, GLPG0555, GLPG0634, GLPG0778, GLPG0974, Gluco, Glucocerin, glucosamine, glucosamine hydrochloride, glucosamine sulfate, Glucotin, Gludex, Glutilage, GLY079, GLY145, Glycanic, Glycefort up, Glygesic, Glysopep, GMCSF Antibody, GMI1010, GMI1011, GMI1043, GMR321, GN4001, Goanna Salve, Goflex, gold sodium thiomalate, golimumab, GP2013, GPCR modulator, GPR15 Antagonist, GPR183 antagonist, GPR32 antagonist, GPR83 antagonist, G-protein Coupled Receptor Antagonists, Graceptor, Graftac, granulocyte colony-stimulating factor antibody, granulocyte-macrophage colony-stimulating factor antibody, Gravx, GRC4039, Grelyse, GS101, GS9973, GSC100, GSK1605786, GSK1827771, GSK2136525, GSK2941266, GSK315234, GSK681323, GT146, GT442, Gucixiaotong, Gufisera, Gupisone, gusperimus hydrochloride, GW274150, GW3333, GW406381, GW856553, GWB78, GXP04, Gynestrel, Haloart, halopredone acetate, Haloxin, HANALL, Hanall Soludacortin, Havisco, Hawon Bucillamin, HB802, HC31496, HCQ 200, HD104, HD203, HD205, HDAC inhibitor, HE2500, HE3177, HE3413, Hecoria, Hectomitacin, Hefasolon, Helen, Helenil, HemaMax, Hematom, hematopoietic stem cells, Hematrol, Hemner, Hemril, heparinoid, Heptax, HER2 Antibody, Herponil, hESC Derived Dendritic Cells, hESC Derived Hematopoietic stem cells, Hespercorbin, Hexacorton, Hexadrol, hexetidine, Hexoderm, Hexoderm Salic, HF0220, HF1020, HFT-401, hG-CSFR ED Fc, Hiberna, high mobility group box 1 antibody, Hiloneed, Hinocam, hirudin, Hirudoid, Hison, Histamine H4 Receptor Antagonist, Hitenercept, Hizentra, HL036, HL161, HMPL001, HMPL004, HMPL004, HMPL011, HMPL342, HMPL692, honey bee venom, Hongqiang, Hotemin, HPH116, HTI101, HuCAL Antibody, Human adipose mesenchymal stem cells, anti-MHC class II monoclonal antibody, Human Immunoglobulin, Human Placenta Tissue Hydrolysate, HuMaxCD4, HuMax-TAC, Humetone, Humicade, Humira, Huons Betamethasone sodium phosphate, Huons dexamethasone sodium phosphate, Huons Piroxicam, Huons Talniflumate, Hurofen, Huruma, Huvap, HuZAF, HX02, Hyalogel, hyaluronate sodium, hyaluronic acid, hyaluronidase, Hyaron, Hycocin, Hycort, Hy-Cortisone, hydrocortisone, hydrocortisone acetate, hydrocortisone butyrate, hydrocortisone hemisuccinate, hydrocortisone sodium phosphate, hydrocortisone sodium succinate, Hydrocortistab, Hydrocortone, Hydrolin, Hydroquine, Hydro-Rx, Hydrosone HIKMA, hydroxychloroquine, hydroxychloroquine sulfate, Hylase Dessau, HyMEX, Hypen, HyQ, Hysonate, HZN602, I.M.75, IAP Inhibitors, Ibalgin, Ibalgin, Ibex, ibrutinib, IBsolvMIR, Ibu, Ibucon, Ibudolor, Ibufen, Ibuflam, Ibuflex, Ibugesic, Ibu-Hepa, Ibukim, Ibumal, Ibunal, Ibupental, Ibupril, Ibuprof, ibuprofen, Ibuscent, Ibusoft, Ibusuki Penjeong, Ibususpen, Ibutard, Ibutop, Ibutra, Ibutrex, IC487892, ichthammol, ICRAC Blocker, IDEC131, IDECCE9.1, Ides, Idicin, Idizone, IDN6556, Idomethine, IDR1, Idyl SR, Ifen, iguratimod, IK6002, IKK-beta inhibitor, IL17 Antagonist, IL-17 Inhibitor, IL-17RC, IL18, IL1Hy1, IL1R1, IL-23 Adnectin, IL23 Inhibitor, IL23 Receptor Antagonist, IL-31 mAb, IL-6 Inhibitor, IL6Qb, Ilacox, Ilaris, ilodecakin, ILV094, ILV095, Imaxetil, IMD0560, IMD2560, Imesel Plus, Iminoral, Immodin, IMMU103, IMMU106, Immucept, Immufine, Immunex Syrup, immunoglobulin, immunoglobulin G, Immunoprin, ImmunoRel, Immurin, IMO8400, IMP731 antibody, Implanta, Imunocell, Imuran, Imurek, Imusafe, Imusporin, Imutrex, IN0701, Inal, INCB039110, INCB18424, INCB28050, INCB3284, INCB3344, Indexon, Indic, Indo, Indo-A, Indobid, Indo-Bros, Indocaf, Indocarsil, Indocid, Indocin, Indomehotpas, Indomen, Indomet, Indometacin, indomethacin, Indomethasone, Indometin, Indomin, Indopal, Indoron, Indotroxin, INDUS830, INDUS83030, Infladase, Inflamac, Inflammasome inhibitor, Inflavis, Inflaxen, Inflectra, infliximab, Ingalipt, Inicox dp, Inmecin, Inmunoartro, Innamit, InnoD06006, INO7997, Inocin, Inoten, Inovan, Inpra, Inside Pap, Insider-P, Instacyl, Instracool, Intafenac, Intaflam, Inteban, Inteban Spansule, integrin, alpha 1 antibody, integrin, alpha 2 antibody, Intenurse, interferon alfa, interferon beta-1a, interferon gamma, interferon gamma antibody, Interking, interleukin 1 Hy1, interleukin 1 antibody, interleukin 1 receptor antibody, interleukin 1, beta antibody, interleukin 10, interleukin 10 antibody, interleukin 12, interleukin 12 antibody, interleukin 13 antibody, interleukin 15 antibody, interleukin 17 antibody, interleukin 17 receptor C, interleukin 18, interleukin 18 binding protein, interleukin 18 antibody, interleukin 2 receptor, alpha antibody, interleukin 20 antibody, Interleukin 21 mAb, interleukin 23 aptamer, interleukin 31 antibody, interleukin 34, Interleukin 6 Inhibitor, interleukin 6 antibody, interleukin 6 receptor antibody, interleukin 7, interleukin 7 receptor antibody, interleukin 8, interleukin 8 antibody, interleukin-18 antibody, Intidrol, Intradex, Intragam P, Intragesic, Intraglobin F, Intratect, Inzel, lomab B, IOR-T3, IP751, IPH2201, IPH2301, IPH24, IPH33, IPI145, Ipocort, IPP201007, I-Profen, Iprox, Ipson, Iputon, IRAK4 Inhibitor, Iremod, Irtonpyson, IRX3, IRX5183, ISA247, ISIS104838, ISIS2302, ISISCRPRx, Ismafron, IsoQC inhibitor, Isox, ITF2357, Iveegam EN, Ivepred, IVIG-SN, IWOOL Izilox, J607Y, J775Y, JAK Inhibitor, JAK3 inhibitor, JAK3 kinase inhibitor, JI3292, JI4135, Jinan Lida, JNJ10329670, JNJ18003414, JNJ26528398, JNJ27390467, JNJ28838017, JNJ31001958, JNJ38518168, JNJ39758979, JNJ40346527, JNJ7777120, JNT-Plus, Joflam, Joint Glucosamin, Jointec, Jointstem, Joinup, JPE1375, JSM10292, JSM7717, JSM8757, JTE051, JTE052, JTE522, JTE607, Jusgo, K412, K832, Kaflam, KAHR101, KAHR102, KAI9803, Kalymin, Kam Predsol, Kameton, KANAb071, Kappaproct, KAR2581, KAR3000, KAR3166, KAR4000, KAR4139, KAR4141, KB002, KB003, KD7332, KE298, keliximab, Kemanat, Kemrox, Kenacort, Kenalog, Kenaxir, Kenketsu Venoglobulin-IH, Keplat, Ketalgipan, Keto Pine, Keto, Ketobos, Ketofan, Ketofen, Ketolgan, Ketonal, Ketoplus Kata Plasma, ketoprofen, Ketores, Ketorin, ketorolac, ketorolac tromethamine, Ketoselect, Ketotop, Ketovail, Ketricin, Ketroc, Ketum, Keyi, Keyven, KF24345, K-Fenac, K-Fenak, K-Gesic, Kifadene, Kilcort, Kildrol, KIM127, Kimotab, Kinase Inhibitor 4SC, Kinase N, Kincort, Kindorase, Kineret, Kineto, Kitadol, Kitex, Kitolac, KLK1 Inhibitor, Klofen-L, Klotaren, KLS-40or, KLS-40ra, KM277, Knavon, Kodolo orabase, Kohakusanin, Koide, Koidexa, Kolbet, Konac, Kondro, Kondromin, Konshien, Kontab, Kordexa, Kosa, Kotase, KPE06001, KRP107, KRP203, KRX211, KRX252, KSB302, K-Sep, Kv 1.3 Blocker, Kv1.3 4SC, Kv1.3 inhibitor, KVK702, Kynol, L156602, Labizone, Labohydro, Labopen, Lacoxa, Lamin, Lamit, Lanfetil, laquinimod, larazotide acetate, LAS186323, LAS187247, LAS41002, Laticort, LBEC0101, LCP3301, LCP-Siro, LCP-Tacro, LCsA, LDP392, Leap-S, Ledercort, Lederfen, Lederlon, Lederspan, Lefenine, leflunomide, Leflux, Lefno, Lefra, Leftose, Lefumide, Lefunodin, Lefva, lenalidomide, lenercept, LentiRA, LE015520, Leodase, Leukine, Leukocyte function-associated antigen-1 antagonist, leukocyte immunoglobulin-like receptor, subfamily A, member 4 antibody, Leukothera, leuprolide acetate, levalbuterol, levomenthol, LFA-1 Antagonist, LFA451, LFA703, LFA878, LG106, LG267 Inhibitors, LG688 Inhibitors, LGD5552, Li Life, LidaMantle, Lidex, lidocaine, lidocaine hydrochloride, Lignocaine hydrochloride, LIM0723, LIM5310, Limethason, Limus, Limustin, Lindac, Linfonex, Linola acute, Lipcy, lisofylline, Listran, Liver X Receptor modulator, Lizak, LJP1207, LJP920, Lobafen, Lobu, Locafluo, Localyn, Locaseptil-Neo, Locpren, Lodine, Lodotra, Lofedic, Loflam, Lofnac, Lolcam, Lonac, lonazolac calcium, Loprofen, Loracort, Lorcam, Lorfenamin, Lorinden Lotio, Lorncrat, lornoxicam, Lorox, losmapimod, loteprednol etabonate, Loteprednol, Lotirac, Low Molecular *Ganoderma Lucidum* Polysaccharide, Loxafen, Loxfenine, Loxicam, Loxofen, Loxonal, Loxonin, loxoprofen sodium, Loxoron, LP183A1, LP183A2, LP204A1, LPCN1019, LT1942, LT1964, LTNS101, LTNS103, LTNS106, LTNS108, LTS1115, LTZMP001, Lubor, lumiracoxib, Lumitect, LX2311, LX2931, LX2932, LY2127399, LY2189102, LY2439821, LY294002, LY3009104, LY309887, LY333013, lymphocyte activation gene 3 antibody, Lymphoglobuline, Lyser, lysine aspirin, Lysobact, Lysoflam, Lysozyme hydrochloride, M3000, M834, M923, mAb hG-CSF, MABP1, macrophage migration inhibitory factor antibody, Maitongna, Majamil prolongatum, major histocompatibility complex class II DR antibody, major histocompatibility complex class II antibody, Malidens, Malival, mannan-binding lectin, mannan-binding lectin-associated serine protease-2 antibody, MapKap Kinase 2 Inhibitor, maraviroc, Marlex, masitinib, Maso, MASP2 antibody, MAT304, Matrix Metalloprotease Inhibitor, mavrilimumab, Maxiflam, Maxilase, Maximus, Maxisona, Maxius, Maxpro, Maxrel, Maxsulid, Maxy12, Maxy30, MAXY4, Maxy735, Maxy740, Mayfenamic, MB 11040, MBPY003b, MCAF5352A, McCam, McRofy, MCS18, MD707, MDAM, MDcort, MDR06155, MDT012, Mebicam, Mebuton, meclofenamate sodium, Meclophen, Mecox, Medacomb, Medafen, Medamol, Medesone, MEDI2070, MEDI5117, MEDI541, MEDI552, MEDI571, Medicox, Medifen, Medisolu, Medixon, Mednisol, Medrol, Medrolon, medroxyprogesterone acetate, Mefalgin, mefenamic acid, Mefenix, Mefentan, Meflen, Mefnetra forte, Meftagesic-DT, Meftal, Megakaryocyte Growth and Development Factor, Megaspas, Megaster, megestrol acetate, Meite, Meksun, Melbrex, Melcam, Melcam, Melflam, Melic, Melica, Melix, Melocam, Melocox, Mel-One, Meloprol, Melosteral, Melox, Meloxan, Meloxcam, Meloxic, Meloxicam, Meloxifen, Meloxin, Meloxiv, Melpred, Melpros, Melurjin, Menamin, Menisone, Menthomketo, Menthoneurin, Mentocin, Mepa, Mepharen, meprednisone, Mepresso, Mepsolone, mercaptopurine, Mervan, Mesadoron, mesalamine, Mesasal, Mesatec, Mesenchymal Precursor Cells, mesenchymal stem cell, Mesipol, Mesren, Mesulan, Mesulid, Metacin, Metadaxan, Metaflex, Metalcaptase, metalloenzyme inhibitors, Metapred, Metax, Metaz, Meted, Metedic, Methacin, Methaderm, Methasone, Methotrax, methotrexate, methotrexate sodium, Methpred, Methyl prednisolone acetate, methyl salicylate, methyl sulphonyl methane, Methylon, Methylpred, methylprednisolone, methylprednisolone acetate, methylprednisolone sodium succinate, methylprednisolone succinate, Methylprednisolone, Methysol, Metindol, Metoart, Metoject, Metolate, Metoral, Metosyn, Metotab, Metracin, Metrex, metronidazole, Metypred, Mevamox, Mevedal, Mevilox, Mevin SR, Mexilal, Mexpharm, Mext, Mextran, MF280, M-FasL, MHC class II beta chain peptide, Micar, Miclofen, Miclofenac, Micofenolato Mofetil, Micosone, Microdase, microRNA 181 a-2 oligonucleotide, MIF Inhibitors, MIFQb, MIKA-Ketoprofen, Mikametan, milodistim, Miltax, Minafen, Minalfen, Minalfene, Minesulin, Minocort, Mioflex, Miolox, Miprofen, Miridacin, Mirloks, Misoclo, Misofenac, MISTB03, MISTB04, Mitilor, mizoribine, MK0359, MK0812, MK0873, MK2 Inhibitors, MK50, MK8457, MK8808, MKC204, MLN0002, MLN0415, MLN1202, MLN273, MLN3126, MLN3701, MLN3897, MLNM002, MM093, MM7XX, MN8001, Mobic, Mobicam, Mobicox, Mobifen Plus, Mobilat, Mobitil, Mocox, Modigraf, Modrasone, Modulin, Mofecept, Mofetyl, mofezolac sodium, Mofilet, Molace, molgramostim, Molslide, Momekin, Momen Gele, Moment 100, Momesone, Momesun, Mometamed, mometasone, mometasone furoate, Monimate, monosodium alpha-luminol, Mopik, MOR103, MOR104, MOR105, MOR208 antibody, MORAb022, Moricam, morniflumate, Mosuolit, Motoral, Movaxin, Mover, Movex, Movix, Movoxicam, Mox Forte, Moxen, moxifloxacin hydrochloride, Mozobil, MP, MP0210, MP0270, MP1000, MP1031, MP196, MP435, MPA, mPGES-1 inhibitor, MPSS, MRX7EAT, MSL, MT203, MT204, mTOR Inhibitor, MTRX1011A, Mucolase, Multicort, MultiStem, muramidase, muramidase, muramidase hydrochloride, muromonab-CD3, Muslax, Muspinil, Mutaze, Muvera, MX68, Mycept, Mycocell, Mycocept, Mycofenolatmofetil Actavis, Mycofet, Mycofit, Mycolate, Mycoldosa, Mycomun, Myconol, mycophenolate mofetil, mycophenolate sodium, mycophenolic acid, Mycotil, myeloid progenitor cells, Myfenax, Myfetil, Myfortic, Mygraft, Myochrysine, Myocrisin, Myprodol, Mysone, nab-Cyclosporine, Nabentac, nabiximols, Nabton, Nabuco, Nabucox, Nabuflam, Nabumet, nabumetone, Nabuton, Nac Plus, Nacta, Nacton, Nadium, Naklofen SR, NAL1207, NAL1216, NAL1219, NAL1268, NAL8202, Nalfon, Nalgesin S, namilumab, Namsafe, nandrolone, Nanocort, Nanogam, Nanosomal Tacrolimus, Napageln, Napilac, Naprelan, Napro, Naprodil, Napronax, Napropal, Naproson, Naprosyn, Naproval, Naprox, naproxen, naproxen sodium, Naproxin, Naprozen, Narbon, Narexsin, Naril, Nasida, natalizumab, Naxdom, Naxen, Naxin, Nazovel, NC2300, ND07, NDC01352, Nebumetone, NecLipGCSF, Necsulide, Necsunim, Nelsid-S, Neo Clobenate, Neo Swiflox FC, Neocoflan, Neo-Drol, Neo-Eblimon, Neo-Hydro, Neoplanta, Neoporine, Neopreol, Neoprox, Neoral, Neotrexate, Neozen, Nepra, Nestacort, Neumega, Neupogen, Neuprex, Neurofenac, Neurogesic, Neurolab, Neuroteradol, Neuroxicam, Neutalin, neutrazumab, Neuzym, New Panazox, New-fenstop, NewGam, Newmafen, Newmatal, Newsicam, NEX1285, sFcRIIB, Nextomab, NF-kappaB Inhibitor, NF-kB inhibitor, NGD20001, NHP554B, NHP554P, NI0101 antibody, NI0401, NI0501 antibody, NI0701, NI071, NI1201 antibody, NI1401, Nicip, Niconas, Nicool, NiCord, Nicox, Niflumate, Nigaz, Nikam, Nilitis, Nimace, Nimaid, Nimark-P, Nimaz, Nimcet Juicy, Nime, Nimed, Nimepast, nimesulide, Nimesulix, Nimesulon, Nimica Plus, Nimkul, Nimlin, Nimnat, Nimodol, Nimpidase, Nimsaid-S, Nimser, Nimsy-SP, Nimupep, Nimusol, Nimutal, Nimuwin, Nimvon-S, Nincort, Niofen, Nipan, Nipent, Nise, Nisolone, Nisopred, Nisoprex, Nisulid, nitazoxanide, Nitcon, nitric oxide, Nizhvisal B, Nizon, NL, NMR1947, NN8209, NN8210, NN8226, NN8555, NN8765, NN8828, NNC014100000100, NNC051869, Noak, Nodevex, Nodia, Nofenac, Noflagma, Noflam, Noflamen, Noflux, Non-antibacterial Tetracyclines, Nonpiron, Nopain, Normferon, Notpel, Notritis, Novacort, Novagent, Novarin, Novigesic, NOXA12, NOXD19, Noxen, Noxon, NPI1302a-3, NPI1342, NPI1387, NPI1390, NPRCS1, NPRCS2, NPRCS3, NPRCS4, NPRCS5, NPRCS6, NPS3, NPS4, nPTery, NU3450, nuclear factor NF-kappa-B p65 subunit oligonucleotide, Nucort, Nulojix, Numed-Plus, Nurokind Ortho, Nusone-H, Nutrikemia, Nuvion, NVO7alpha, NX001, Nyclobate, Nyox, Nysa, Obarcort, OC002417, OC2286, ocaratuzumab, OCTSG815, Oedemase, Oedemase-D, ofatumumab, Ofgyl-O, Ofvista, OHR118, OKi, Okifen, Oksamen, Olai, olokizumab, Omeprose E, Omnacortil, Omneed, Omniclor, Omnigel, Omniwel, onercept, ON04057, ONS1210, ONS1220, Ontac Plus, Ontak, ONX0914, OPC6535, opebacan, OPN101, OPN201, OPN302, OPN305, OPN401, oprelvekin, OPT66, Optifer, Optiflur, OptiMIRA, Orabase Hca, Oradexon, Oraflex, Oral-Fenac, Oralog, Oralpred, Ora-sed, Orasone, orBec, Orbone forte, Orcl, ORE10002, ORE10002, Orencia, Org214007, Org217993, Org219517, Org223119, Org37663, Org39141, Org48762, Org48775, Orgadrone, Ormoxen, Orofen Plus, Oromylase Biogaran, Orthal Forte, Ortho Flex, Orthoclone OKT3, Orthofen, Orthoflam, Orthogesic, Orthoglu, Ortho-II, Orthomac, Ortho-Plus, Ortinims, Ortofen, Orudis, Oruvail, OS2, Oscart, Osmetone, Ospain, Ossilife, Ostelox, Osteluc, Osteocerin, osteopontin, Osteral, otelixizumab, Otipax, Ou Ning, OvaSave, OX40 Ligand Antibody, Oxa, Oxagesic CB, Oxalgin DP, oxaprozin, OXCQ, Oxeno, Oxib MD, Oxibut, Oxicam, Oxiklorin, Oximal, Oxynal, oxyphenbutazone, Oxyphenbutazone, ozoralizumab, P13 peptide, P1639, P21, P2X7 Antagonists, p38 Alpha Inhibitor, p38 Antagonist, p38 MAP kinase inhibitor, p38alpha MAP Kinase Inhibitor, P7 peptide, P7170, P979, PA401, PA517, Pabi-dexamethasone, PAC, PAC10649, paclitaxel, Painoxam, Paldon, Palima, pamapimod, Pamatase, Panafcort, Panafcortelone, Panewin, PanGraf, Panimun Bioral, Panmesone, Panodin SR, Panslay, Panzem, Panzem NCD, PAP1, papain, Papirzin, Pappen K Pap, Paptinim-D, paquinimod, PAR2 Antagonist, Paracetamol, Paradic, Parafen TAJ, Paramidin, Paranac, Parapar, Parci, parecoxib, Parixam, Parry-S, Partaject Busulfan, pateclizumab, Paxceed, PBI0032, PBI1101, PBI1308, PBI1393, PBI1607, PBI1737, PBI2856, PBI4419, PBI4419, P-Cam, PCI31523, PCI32765, PCI34051, PCI45261, PCI45292, PCI45308, PD360324, PD360324, PDA001, PDE4 inhibitor, PDE-IV Inhibitor, PDL241 antibody, PDL252, Pediapred, Pefree, pegacaristim, Peganix, Peg-Interleukin 12, pegsunercept, Pegsunercept, PEGylated arginine deiminase, peldesine, pelubiprofen, Penacle, penicillamine, Penostop, Pentalgin, Pentasa, Pentaud, pentostatin, Peon, Pepdase, Pepser, Peptirase, Pepzen, Pepzol, Percutalgine, Periochip, Peroxisome Proliferator Activated Receptor gamma modulators, Petizene, PF00344600, PF04171327, PF04236921, PF04308515, PF05230905, PF05280586, PF251802, PF3475952, PF3491390, PF3644022, PF4629991, PF4856880, PF5212367, PF5230896, PF547659, PF755616, PF9184, PG27, PG562, PG760564, PG8395, PGE3935199, PGE527667, PH5, PH797804, PHA408, Pharmaniaga Mefenamic acid, Pharmaniaga Meloxicam, Pheldin, Phenocept, phenylbutazone, PHY702, PI3K delta inhibitor, PI3K Gamma/Delta Inhibitor, PI3K Inhibitor, Picalm, pidotimod, piketoprofen, Pilelife, Pilopil, Pilovate, pimecrolimus, Pipethanen, Piractam, Pirexyl, Pirobet, Piroc, Pirocam, Pirofel, Pirogel, Piromed, Pirosol, Pirox, Piroxen, Piroxicam, piroxicam betadex, Piroxifar, Piroxil, Piroxim, Pixim, Pixykine, PKC Theta Inhibitor, PL3100, PL5100 Diclofenac, Placenta Polypeptide, Plaquenil, plerixafor, Plocfen, PLR14, PLR18, Plutin, PLX3397, PLX5622, PLX647, PLX-BMT, pms-Diclofenac, pms-Ibuprofen, pms-Leflunomide, pms-Meloxicam, pms-Piroxicam, pms-Prednisolone, pms-Sulfasalazine, pms-Tiaprofenic, PMX53, PN0615, PN100, PN951, podofilox, POL6326, Polcortolon, Polyderm, Polygam S/D, Polyphlogin, Poncif, Ponstan, Ponstil Forte, Porine-A Neoral, Potaba, potassium aminobenzoate, Potencort, Povidone, povidone iodine, pralnacasan, Prandin, Prebel, Precodil, Precortisyl Forte, Precortyl, Predfoam, Predicort, Predicorten, Predilab, Predilone, Predmetil, Predmix, Predna, Prednesol, Predni, prednicarbate, Prednicort, Prednidib, Prednifarma, Prednilasca, prednisolone, prednisolone acetate, prednisolone sodium phosphate, prednisolone sodium succinate, prednisolone sodium succinate, prednisone, prednisone acetate, Prednitop, Prednol-L, Prednox, Predone, Predonema, Predsol, Predsolone, Predsone, Predval, Preflam, Prelon, Prenaxol, Prenolone, Preservex, Preservin, Presol, Preson, Prexige, Priliximab, Primacort, Primmuno, Primofenac, prinaberel, Privigen, Prixam, Probuxil, Procarne, Prochymal, Procider-EF, Proctocir, Prodase, Prodel B, Prodent, Prodent Verde, Proepa, Profecom, Profenac L, Profenid, Profenol, Proflam, Proflex, Progesic Z, proglumetacin, proglumetacin maleate, Prograf, Prolase, Prolixan, promethazine hydrochloride, Promostem, Promune, PronaB, pronase, Pronat, Prongs, Pronison, Prontoflam, Propaderm-L, Propodezas, Propolisol, Proponol, propyl nicotinate, Prostaloc, Prostapol, Protacin, Protase, Protease Inhibitors, Protectan, Proteinase Activated Receptor 2 Inhibitor, Protofen, Protrin, Proxalyoc, Proxidol, Proxigel, Proxil, Proxym, Prozym, PRT062070, PRT2607, PRTX100, PRTX200, PRX106, PRX167700, Prysolone, PS031291, PS375179, PS386113, PS540446, PS608504, PS826957, PS873266, Psorid, PT, PT17, PTL101, P-Transfer Factor peptides, PTX3, Pulminiq, Pulsonid, Purazen, Pursin, PVS40200, PX101, PX106491, PX114, PXS2000, PXS2076, PYM60001, Pyralvex, Pyranim, pyrazinobutazone, Pyrenol, Pyricam, Pyrodex, Pyroxi-Kid, QAX576, Qianbobiyan, QPI1002, QR440, qT3, Quiacort, Quidofil, R107s, R125224, R1295, R132811, R1487, R1503, R1524, R1628, R333, R348, R548, R7277, R788, rabeximod, Radix Isatidis, Radofen, Raipeck, Rambazole, Randazima, Rapacan, Rapamune, Raptiva, Ravax, Rayos, RDEA119, RDEA436, RDP58, Reactine, Rebif, REC200, Recartix-DN, receptor for advanced glycation end products antibody, Reclast, Reclofen, recombinant HSA-TIMP-2, recombinant human alkaline Phosphatase, recombinant Interferon Gamma, Recominant human alkaline phosphatase, Reconil, Rectagel HC, Recticin, Recto Menaderm, Rectos, Redipred, Redolet, Refastin, Regenica, REGN88, Relafen, Relaxib, Relev, Relex, Relifen, Relifex, Relitch, Rematof, remestemcel-1, Remesulidum, Remicade, Remsima, Remsima, Remsima, ReN1869, Renacept, Renfor, Renodapt, Renodapt-S, Renta, Reosan, Repare-AR, Reparilexin, reparixin, Repertaxin, Repisprin, Resochin, Resol, resolvin E1, Resurgil, Re-tin-colloid, Retoz, Reumacap, Reumacon, Reumadolor, Reumador, Reumanisal, Reumazin, Reumel, Reumotec, Reuquinol, revamilast, Revascor, Reviroc, Revlimid, Revmoksikam, Rewalk, Rexalgan, RG2077, RG3421, RG4934 antibody, RG7416, RG7624, Rheila, Rheoma, Rheprox, Rheudenolone, Rheufen, Rheugesic, Rheumacid, Rheumacort, Rheumatrex, Rheumesser, Rheumid, Rheumon, Rheumox, Rheuoxib, Rhewlin, Rhucin, RhuDex, Rhulef, Ribox, Ribunal, Ridaura, rifaximin, rilonacept, rimacalib, Rimase, Rimate, Rimatil, Rimesid, risedronate sodium, Ritamine, Rito, Rituxan, rituximab, RNS60, RO1138452, Ro313948, RO3244794, RO5310074, Rob803, Rocamix, Rocas, Rofeb, rofecoxib, Rofee, Rofewal, Roficip Plus, Rojepen, Rokam, Rolodiquim, Romacox Fort, Romatim, romazarit, Ronaben, ronacaleret, Ronoxcin, ROR Gamma T Antagonist, ROR gamma t inverse agonists, Rosecin, rosiglitazone, Rosmarinic acid, Rotan, Rotec, Rothacin, Roxam, Roxib, Roxicam, Roxopro, Roxygin DT, RP54745, RPI78, RPI78M, RPI78MN, RPIMN, RQ00000007, RQ00000008, RTA402, R-Tyflam, Rubicalm, Rubifen, Ruma pap, Rumalef, Rumidol, Rumifen, Runomex, rusalatide acetate, ruxolitinib, RWJ445380, RX10001, Rycloser MR, Rydol, S1P Receptor Agonists, SW Receptor Modulators, S1P1 Agonist, S1P1 receptor agonist, 52474, S3013, SA237, SA6541, Saaz, S-adenosyl-L-methionine-sulfate-p-toluene sulfonate, Sala, Salazidin, Salazine, Salazopyrin, Salcon, Salicam, salsalate, Sameron, SAN300, Sanaven, Sandimmun, Sandoglobulin, Sanexon, SangCya, SAR153191, SAR302503, SAR479746, Sarapep, sargramostim, Sativex, Savantac, Save, Saxizon, Sazo, SB1578, SB210396, SB217969, SB242235, SB273005, SB281832, SB683698, SB751689, SBI087, SC080036, SC12267, SC409, Scaflam, SCD ketoprofen, SCI0323, SCI0469, SD-15, SD281, SDP051 antibody, Sd-rxRNA, secukinumab, Sedase, Sedilax, Sefdene, Seizyme, SEL113, Seladin, Selecox, selectin P ligand antibody, Glucocorticoid Receptor Agonist, Selectofen, Selektine, SelK1 antibody, Seloxx, Selspot, Selzen, Selzenta, Selzentry, semapimod, semapimod hydrochloride, semparatide, Semparatide, Senafen, Sendipen, Senterlic, SEP119249, Sepdase, Septirose, Seractil, Serafen-P, Serase, Seratid D, Seratiopeptidase, Serato-M, Seratoma Forte, Serazyme, Serezon, Sero, Serodase, Serpicam, Serra, serrapeptase, Serratin, Serratiopeptidase, Serrazyme, Servisone, Seven E P, SGI1252, SGN30, SGN70, SGX203, shark cartilage extract, Sheril, Shield, Shifazen, Shifazen-Fort, Shincort, Shincort, Shiosol, ShK186, Shuanghuangxiaoyan, SI615, SI636, Sigmasporin, Sigmasporin, SIM916, Simpone, Simulect, Sinacort, Sinalgia, Sinapol, Sinatrol, Sinsia, siponimod, Sirolim, sirolimus, Siropan, Sirota, Sirova, sirukumab, Sistal Forte, SKF105685, SKF105809, SKF106615, SKF86002, Skinalar, Skynim, Skytrip, SLAM family member 7 antibody, Slo-indo, SM101, SM201 antibody, SM401, SMAD family member 7 oligonucleotide, SMART Anti-IL-12 Antibody, SMP114, SNO030908, SNO070131, sodium aurothiomalate, sodium chondroitin sulfate, sodium deoxyribonucleotide, sodium gualenate, sodium naproxen, sodium salicylate, Sodixen, Sofeo, Soleton, Solhidrol, Solicam, Soliky, Soliris, Sol-Melcort, Solomet, Solondo, Solone, Solu-Cort, Solu-Cortef, Solu-Decortin H, Solufen, Solu-Ket, Solumark, Solu-Medrol, Solupred, Somalgen, somatropin, Sonap, Sone, sonepcizumab, Sonexa, Sonim, Sonim P, Soonil, Soral, Sorenil, sotrastaurin acetate, SP-10, SP600125, Spanidin, SP-Cortil, SPD550, Spedace, sperm adhesion molecule 1, Spictol, spleen tyrosine kinase oligonucleotide, Sporin, S-prin, SPWF1501, SQ641, SQ922, SR318B, SR9025, SRT2104, SSR150106, SSR180575, SSSO7 antibody, ST1959, STA5326, stabilin 1 antibody, Stacort, Stalogesic, stanozolol, Staren, Starmelox, Stedex IND-SWIFT, Stelara, Stemin, Stenirol, Sterapred, Steriderm S, Steno, Sterisone, Steron, stichodactyla helianthus peptide, Stickzenol A, Stiefcortil, Stimulan, STNM01, Store Operated Calcium Channel (SOCC) Modulator, STP432, STP900, Stratasin, Stridimmune, Strigraf, SU Medrol, Subreum, Subuton, Succicort, Succimed, Sulan, Sulcolon, Sulfasalazin Heyl, Sulfasalazin, sulfasalazine, Sulfovit, Sulidac, Sulide, sulindac, Sulindex, Sulinton, Sulphafine, Sumilu, SUN597, Suprafen, Supretic, Supsidine, Surgam, Surgamine, Surugamu, Suspen, Suton, Suvenyl, Suwei, SW Dexasone, Syk Family Kinase Inhibitor, Syn1002, Synacran, Synacthen, Synalar C, Synalar, Synavive, Synercort, Sypresta, T cell cytokine-inducing surface molecule antibody, T cell receptor antibody, T5224, T5226, TA101, TA112, TA383, TA5493, tabalumab, Tacedin, Tacgraf, TACIFc5, Tacrobell, Tacrograf, Tacrol, tacrolimus, Tadekinig alpha, Tadolak, TAFA93, Tafirol Artro, Taizen, TAK603, TAK715, TAK783, Takfa, Taksta, talarozole, Talfin, Talmain, talmapimod, Talmea, Talnif, talniflumate, Talos, Talpain, Talumat, Tamalgen, Tamceton, Tamezon, Tandrilax, tannins, Tannosynt, Tantum, tanzisertib, Tapainbeta, Tapoein, Tarenac, tarenflurbil, Tarimus, Tarproxen, Tauxib, Tazomust, TBR652, TC5619, T-cell, immune regulator 1, ATPase, H+ transporting, lysosomal V0 subunit A3 antibody, TCK1, T-cort, T-Dexa, Tecelac, Tecon, teduglutide, Teecort, Tegeline, Tementil, temoporfin, Tencam, Tendrone, Tenefuse, Tenfly, tenidap sodium, Tenocam, Tenoflex, Tenoksan, Tenotil, tenoxicam, Tenoxim, Tepadina, Teracort, Teradol, tetomilast, TG0054, TG1060, TG20, TG20, tgAAC94, Th1/Th2 Cytokine Synthase Inhibitor, Th-17 cell inhibitors, Thalido, thalidomide, Thalomid, Themisera, Thenil, Therafectin, Therapyace, thiarabine, Thiazolopyrimidines, thioctic acid, thiotepa, THR090717, THR0921, Threenofen, Thrombate III, Thymic peptide, Thymodepressin, Thymogam, Thymoglobulin, Thymoglobuline, Thymoject thymic peptides, thymomodulin, thymopentin, thymopolypetides, tiaprofenic acid, tibezonium iodide, Ticoflex, tilmacoxib, Tilur, T-immune, Timocon, Tiorase, Tissop, TKB662, TL011, TLR4 antagonists, TLR8 inhibitor, TM120, TM400, TMX302, TNF Alpha inhibitor, TNF alpha-TNF receptor antagonist, TNF antibody, TNF receptor superfamily antagonists, TNF TWEAK Bi-Specific, TNF-Kinoid, TNFQb, TNFR1 antagonist, TNR001, TNX100, TNX224, TNX336, TNX558, tocilizumab, tofacitinib, Tokuhon happ, TOL101, TOL102, Tolectin, ToleriMab, Tolerostem, Tolindol, toll-like receptor 4 antibody, toll-like receptor antibody, tolmetin sodium, Tongkeeper, Tonmex, Topflame, Topicort, Topleucon, Topnac, Toppin Ichthammol, toralizumab, Toraren, Torcoxia, Toroxx, Tory, Toselac, Totaryl, Touch-med, Touchron, Tovok, Toxic apis, Toyolyzom, TP4179, TPCA1, TPI526, TR14035, Tradil Fort, Traficet-EN, Tramace, tramadol hydrochloride, tranilast, Transimune, Transporina, Tratul, Trexall, Triacort, Triakort, Trialon, Triam, triamcinolone, triamcinolone acetate, triamcinolone acetonide, triamcinolone acetonide acetate, triamcinolone hexacetonide, Triamcort, Triamsicort, Trianex, Tricin, Tricort, Tricortone, TricOs T, Triderm, Trilac, Trilisate, Trinocort, Trinolone, Triolex, triptolide, Trisfen, Trivaris, TRK170, TRK530, Trocade, trolamine salicylate, Trolovol, Trosera, Trosera D, Troycort, TRX1 antibody, TRX4, Trymoto, Trymoto-A, TT301, TT302, TT32, TT32, TT33, TTI314, tumor necrosis factor, tumor necrosis factor 2-methoxyethyl phosphorothioate oligonucleotide, tumor necrosis factor antibody, tumor necrosis factor kinoid, tumor necrosis factor oligonucleotide, tumor necrosis factor receptor superfamily, member 1B antibody, tumor necrosis factor receptor superfamily1B oligonucleotide, tumor necrosis factor superfamily, member 12 antibody, tumor necrosis factor superfamily, member 4 antibody, tumor protein p53 oligonucleotide, tumour necrosis factor alpha antibody, TuNEX, TXA127, TX-RAD, TYK2 inhibitors, Tysabri, ubidecarenone, Ucerase, ulodesine, Ultiflam, Ultrafastin, Ultrafen, Ultralan, U-Nice-B, Uniplus, Unitrexate, Unizen, Uphaxicam, UR13870, UR5269, UR67767, Uremol-HC, Urigon, U-Ritis, ustekinumab, V85546, Valcib, Valcox, valdecoxib, Valdez, Valdixx, Valdy, Valentac, Valoxib, Valtune, Valus AT, Valz, Valzer, Vamid, Vantal, Vantelin, VAP-1 SSAO Inhibitor, vapaliximab, varespladib methyl, Varicosin, Varidase, vascular adhesion protein-1 antibody, VB110, VB120, VB201, VBY285, Vectra-P, vedolizumab, Vefren, VEGFR-1 Antibody, Veldona, veltuzumab, Vendexine, VenimmunN, Venoforte, Venoglobulin-IH, Venozel, Veral, Verax, vercirnon, vero-Dexamethasone, Vero-Kladribin, Vetazone, VGX1027, VGX750, Vibex MTX, vidofludimus, Vifenac, Vimovo, Vimultisa, Vincort, Vingraf, Vioform-HC, Vioxl, Vioxx, Virobron, visilizumab, Vivaglobin, Vivalde Plus, Vivian-A, VLST002, VLST003, VLST004, VLST005, VLST007, Voalla, voclosporin, Vokam, Vokmor, Volmax, Volna-K, Voltadol, Voltagesic, Voltanase, Voltanec, Voltaren, Voltarile, Voltic, Voren, vorsetuzumab, Votan-SR, VR909, VRA002, VRP1008, VRS826, VRS826, VT111, VT214, VT224, VT310, VT346, VT362, VTX763, Vurdon, VX30 antibody, VX467, VXS, VX509, VX702, VX740, VX745, VX745, VX850, W54011, Walacort, Walix, WC3027, Wilgraf, Winflam, Winmol, Winpred, Winsolve, Wintogeno, WIP901, Woncox, WSB711 antibody, WSB712 antibody, WSB735, WSB961, X071NAB, X083NAB, Xantomicin Forte, Xedenol, Xefo, Xefocam, Xenar, Xepol, X-Flam, Xibra, Xicam, Xicotil, Xifaxan, XL499, XmAb5483, XmAb5485, XmAb5574, XmAb5871, XOMA052, Xpress, XPro1595, XtendTNF, XTo11, Xtra, Xylex-H, Xynofen SR, Yang Shu-IVIG, YHB14112, YM974, Youfeline, Youfenac, Yuma, Yumerol, Yuroben, YY piroxicam, Z104657A, Zacy, Zaltokin, zaltoprofen, Zap70 Inhibitor, Zeepain, Zeloxim Fort, Zema-Pak, Zempack, Zempred, Zenapax, Zenas, Zenol, Zenos, Zenoxone, Zerax, Zerocam, Zerospasm, ZFNs, zinc oxide, Zipsor, ziralimumab, Zitis, Zix-S, Zocort, Zodixam, Zoftadex, zoledronic acid, Zolfin, Zolterol, Zopyrin, Zoralone, ZORprin, Zortress, ZP1848, zucapsaicin, Zunovate, Zwitterionic polysaccharides, ZY1400, Zybodies, Zycel, Zyrofen, Zyrogen Inhibitors, Zyser, Zytrim, and Zywin-Forte. In addition, the anti-inflammatory drugs, as listed above, may be combined with one or more agents listed above or herein or with other agents known in the art.

In some embodiments, a drug that reduces, inhibits, prevents and/or ameliorates inflammation, for example, one of the drugs provided above, is delivered to the suprachoroidal space of the eye using the kits, microneedle devices, and methods disclosed herein, and is used to treat, prevent and/or ameliorate a disease or disorder selected from arthritis, degenerative arthritis, psoriatic arthritis, arthritic disorders, arthritic pain, arthrosis, autoimmune arthritis, autoimmune diseases, autoimmune disorders, axial spondyloarthritis, chronic prosthetic joint infection, collagen induced arthritis, osteoarthritis, rheumatoid arthritis, senile arthritis, seronegative oligoarthritis of the knee, allergic and autoimmune inflammatory diseases, inflammatory diseases, inflammatory disorders, collagen diseases, discoid Lupus Erythematosus, immune deficiencies, immune diseases, immune disorders, immunodeficiency diseases, immunodeficiency disorders, immunoglobulin (IgG2) deficiency, immunoglobulin deficiency, Inflammation, Lambert-Eaton myasthenia syndrome, polymyositis, dermatomyositis, polyneuritis, post-operative ocular inflammation, polychondritis, sporadic inclusion body myositis, Systemic Lupus Erythematosus, T cell deficiency, TNF-receptor associated periodic syndrome, tropical spastic paraparesis, Wegener Granulomatosis, X-linked severe combined immunodeficiency disease, Behcet's disease, Crohn's disease, Crohn's Fistula, cutaneous Lupus Erythematosus, acute inflammation, acute inflammatory edema, adrenocortical insufficiency, cerebral inflammation, chronic lung inflammation, corticoid-responsive inflammatory skin disorders, cutaneous inflammation, dermal inflammation, dry skin inflammatory disease, ear edema, ear inflammation, glossitis, inflammatory bowel disease, inflammatory degenerative disease, inflammatory disorders of the eye and/or ear, inflammatory lesions in fungal infections, inflammatory lesions, inflammatory pain, inflammatory skin diseases or disorders, mouth and gum inflammation, mouth and throat inflammation, musculoskeletal disorders, otitis, pelvic inflammatory disease, perianal inflammation, post operative inflammation, pulmonary inflammation, rectal inflammation, refractory idiopathic inflammatory myopathies, seborrhoeic dermatitis, swelling, aphthous ulcerations, chronic polyarthritis, juvenile rheumatoid arthritis, rheumatic diseases, Sjogren's syndrome, opthalmic for Sjogren's syndrome, transplant rejection, acute allograft rejection, chronic graft rejection, graft versus host disease, humoral rejection in heart transplantation, humoral rejection in kidney transplantation, organ rejection in renal transplantation, solid organ transplant rejection, bronchiolitis obliterans after lung transplantation, rejection of bone marrow transplant, chronic lung transplant rejection, Corneal graft rejection, delayed graft function in kidney transplantation, heart transplant rejection, Homotransplantation rejection, immune rejection of hESC-derived therapeutic grafts, kidney transplant rejection, liver transplant rejection, lung transplant rejection, organ rejection, pancreatic islet transplantation rejection in type I diabetes, renal transplant rejection and xenograft rejection.

In some embodiments, the drug delivered to the suprachoroidal space using the kits, microneedle devices, and methods disclosed herein treats, prevents, and/or ameliorates macular degeneration (e.g., age related macular degeneration, dry age related macular degeneration, exudative age-related macular degeneration, geographic atrophy associated with age related macular degeneration, neovascular (wet) age-related macular degeneration, neovascular maculopathy and age related macular degeneration, occult with no classic choroidal neovascularization (CNV) in age-related macular degeneration, Stargardt's disease, Subfoveal wet Age-Related macular degeneration, and Vitreomacular Adhesion (VMA) associated with Neovascular Age Related macular degeneration). Examples of drugs that treat, prevent and/or ameliorate macular degeneration that can be used in conjunction with the devices and methods described herein include, but are not limited to: A0003, A36 peptide, AAV2-sFLT01, ACE041, ACU02, ACU3223, ACU4429, AdPEDF, aflibercept, AG13958, aganirsen, AGN150998, AGN745, AL39324, AL78898A, AL8309B, ALN-VEG01, alprostadil, AM1101, amyloid beta antibody, anecortave acetate, Anti-VEGFR-2 Alterase, Aptocine, APX003, ARC1905, ARC1905 with Lucentis, ATG3, ATP-binding cassette, sub-family A, member 4 gene, ATXS10, Avastin with Visudyne, AVT101, AVT2, bertilimumab, bevacizumab with verteporfin, bevasiranib sodium, bevasiranib sodium; with ranibizumab, brimonidine tartrate, BVA301, canakinumab, Cand5, Cand5 with Lucentis, CERE140, ciliary neurotrophic factor, CLT009, CNT02476, collagen monoclonal antibody, complement component 5 aptamer (pegylated), complement component 5 aptamer (pegylated) with ranibizumab, complement component C3, complement factor B antibody, complement factor D antibody, copper oxide with lutein, vitamin C, vitamin E, and zinc oxide, dalantercept, DE109, dexamethasone with ranibizumab and verteporfin, disitertide, DNA damage inducible transcript 4 oligonucleotide, E10030, E10030 with Lucentis, EC400, eculizumab, EGP, EHT204, embryonic stem cells, human stem cells, endoglin monoclonal antibody, EphB4 RTK Inhibitor, EphB4 Soluble Receptor, ESBA1008, ETX6991, Evizon, Eyebar, EyePromise Five, Eyevi, Eylea, F200, FCFD4514S, fenretinide, fluocinolone acetonide, fluocinolone acetonide with ranibizumab, fms-related tyrosine kinase 1 oligonucleotide, fms-related tyrosine kinase 1 oligonucleotide with ranibizumab, kinase insert domain receptor 169, fosbretabulin tromethamine, Gamunex, GEM220, GS101, GSK933776, HC31496, Human n-CoDeR, HYB676, IBI-20089 with Lucentis, iCo-008, Iconl, I-Gold, Ilaris, Iluvien, Iluvien with Lucentis, immunoglobulins, integrin alpha5betA1 immunoglobulin fragments, Integrin inhibitor, IRIS Lutein, I-Sense Ocushield, Isonep, isopropyl unoprostone, JPE1375, JSM6427, KH902, LentiVue, LFG316, LP590, LPO1010AM, Lucentis, Lucentis with Visudyne, Lutein ekstra, Lutein with myrtillus extract, Lutein with zeaxanthin, M200, M200 with Lucentis, Macugen, MC1101, MCT355, mecamylamine, Microplasmin, motexafin lutetium, MP0112, NADPH oxidase inhibitors, Neoretna, neurotrophin 4 gene, Nova21012, Nova21013, NT501, NT503, Nutri-Stulln, ocriplasmin, OcuXan, Oftan Macula, Optrin, ORA102 with Avastin, P144, P17, Palomid 529, PAN90806, Panzem, Panzem, PARP Inhibitors, pazopanib hydrochloride, pegaptanib sodium, PF4523655, PG11047, piribedil, platelet-derived growth factor beta polypeptide aptamer (pegylated), platelet-derived growth factor beta polypeptide aptamer (pegylated) with ranibizumab, PLG101, PMX20005, PMX53, POT4, PRS055, PTK787, ranibizumab, ranibizumab with triamcinolone acetonide, ranibizumabwith verteporfin, ranibizumab with volociximab, RD27, Rescula, Retaane, retinal pigment epithelial cells, RetinoStat, RG7417, RN6G, RT101, RTU007, SB267268, serpin peptidase inhibitor, clade F, member 1 gene, shark cartilage extract, Shefl, SIR1046, SIR1076, Sirna027, sirolimus, SMTD004, Snelvit, SOD Mimetics, Soliris, sonepcizumab, squalamine lactate, ST602, StarGen, T2TrpRS, TA106, talaporfin sodium, Tauroursodeoxycholic acid, TG100801, TM, TLCx99, TRC093, TRC105, triamcinolone acetonide with verteporfin, Trivastal Retard, TT30, Ursa, ursursodiol, Vangiolux, VAR10200, vascular endothelial growth factor antibody, vascular endothelial growth factor B, vascular endothelial growth factor kinoid, vascular endothelial growth factor oligonucleotide, VAST Compounds, vatalanib, VEGF Inhibitor, verteporfin, Visudyne, Visudyne with Lucentis and dexamethasone, Visudyne with triamcinolone acetonide, Vivis, volociximab, Votrient, XV615, zeaxanthin, ZFP TF, zinc-monocysteine and Zybrestat. In one embodiment, one or more of the macular degeneration treating drugs described above is combined with one or more agents listed above or herein or with other agents known in the art.

In one embodiment, the kits, methods, and devices provided hererin are used to deliver triamcinolone or triamcinolone acetonide to the suprachoroidal space of an eye of a patient in need thereof. In a further embodiment, the triamcinolone or triamcinolone acetonide is delivered for the treatment of sympathetic ophthalmia, temporal arteritis, uveitis and/or ocular inflammatory conditions. In one embodiment, triamcinolone or triamcinolone acetonide is delivered to the suprachoroidal space of the eye in a patient in need of treatment of sympathetic opthalmia with the methods and devices described herein. In another embodiment, triamcinolone or triamcinolone acetonide is delivered to the suprachoroidal space of the eye in a patient in need of treatment of temporal arteritis with the methods and devices described herein. In yet another embodiment, triamcinolone or triamcinolone acetonide is delivered to the suprachoroidalspace of the eye in a patient in need of treatment of uveitis, with the methods and devices described herein. In another embodiment, triamcinolone or triamcinolone acetonide is delivered to the suprachoroidal space of the eye in a patient in need of treatment of one or more ocular inflammatory conditions, with the methods and devices described herein.

The triamcinolone composition provided herein, in one embodiment, is a suspension comprising microparticles or nanoparticles of triamcinolone or triamcinolone acetonide. The microparticles, in one embodiment, have a D50 of about 3 µm or less. In a further embodiment, the D50 is about 2 µm. In another embodiment, the D50 is about 2 µm or less. In even another embodiment, the D50 is about 1000 nm or less. The microparticles, in one embodiment, have a D99 of about 10 µm or less. In another embodiment, the D99 is about 10 µm. In another embodiment, the D99 is less than about 10 µm or less than about 9 µm or less.

In one embodiment, the triamcinolone composition comprises triamcinolone microparticles. In a further embodiment, the composition comprises polysorbate 80. In another embodiment, the triamcinolone composition comprises one or more of CaCl2, MgCl2, sodium acetate and sodium citrate. In one embodiment, the composition comprises polysorbate 80 at a w/v % of 0.02% or about 0.02%, 0.015% or about 0.015%.

In certain embodiments the drug delivered to ocular tissues using the kits, microneedle devices, and methods disclosed herein treats, prevents, and/or ameliorates fibrosis (e.g. myelofibrosis, fibrosis in diabetic nephropathy, cystic fibrosis, scarring, and skin fibrosis).

In some embodiments, a drug that treats, prevents and/or ameliorates fibrosis is used in conjunction with the kits, devices, and methods described herein, and is delivered to the suprachoroidal space of the eye. In a further embodiment, the drug is Actimmune with Pirfenidone, ACUHTR028, AlphaVBeta5, aminobenzoate potassium, amyloid P, ANG1122, ANG1170, ANG3062, ANG3281, ANG3298, ANG4011, Anti-CTGF RNAi, Aplidin, astragalus membranaceus extract with salvia and schisandra chinensis, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, Galectin-3 inhibitors, GKT137831, GMCT01, GMCT02, GRMD01, GRMD02, GRN510, Heberon Alfa R, interferon alfa-2b, interferon gamma-1b with pirfenidone, ITMN520, JKB119, JKB121, JKB122, KRX168, LPA1receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 Fusion Proteins, RXI109, secretin, STX100, TGF-beta Inhibitor, transforming growth factor, beta receptor 2 oligonucleotide, VA999260 or XV615. In one embodiment, one or more of the fibrosis treating drugs described above is combined with one or more agents listed above or herein or with other agents known in the art.

In some embodiments, a drug that treats, prevents and/or ameliorates diabetic macular edema is used in conjunction with the kits, devices, and methods described herein, and is delivered to the suprachoroidal space of the eye. In a further embodiment, the drug is AKB9778, bevasiranib sodium, Candy5, choline fenofibrate, Cortiject, c-raf 2-methoxyethyl phosphorothioate oligonucleotide, DE109, dexamethasone, DNA damage inducible transcript 4 oligonucleotide, FOV2304, iCo007, KH902, MP0112, NCX434, Optina, Ozurdex, PF4523655, SAR1118, sirolimus, SK0503 or Tri-Lipix. In one embodiment, one or more of the diabetic macular edema treating drugs described above is combined with one or more agents listed above or herein or with other agents known in the art.

In some embodiments, a drug that treats, prevents and/or ameliorates macular edema is used in conjunction with the kits, devices, and methods described herein, and is delivered to the suprachoroidal space of the eye. In a further embodiment, the drug is denufosol tetrasodium, dexamethasone, ecallantide, pegaptanib sodium, ranibizumab or triamcinolone. In addition, the drugs delivered to ocular tissues using the microneedle devices and methods disclosed herein which treat, prevent, and/or ameliorate macular edema, as listed above, may be combined with one or more agents listed above or herein or with other agents known in the art.

In some embodiments, a drug that treats, prevents and/or ameliorates ocular hypertension is used in conjunction with the kits, devices, and methods described herein and is delivered to the suprachoroidal space of the eye. In a further embodiment, the drug is 2-MeS-beta gamma-CC12-ATP, Aceta Diazol, acetazolamide, Aristomol, Arteoptic, AZD4017, Betalmic, betaxolol hydrochloride, Betimol, Betoptic S, Brimodin, Brimonal, brimonidine, brimonidine tartrate, Brinidin, Calte, carteolol hydrochloride, Cosopt, CS088, DE092, DE104, DE111, dorzolamide, dorzolamide hydrochloride, Dorzolamide hydrochloride with Timolol maleate, Droptimol, Fortino', Glaumol, Hypadil, Ismotic, isopropyl unoprostone, isosorbide, Latalux, latanoprost, Latanoprost with Timolol maleate, levobunolol hydrochloride, Lotensin, Mannigen, mannitol, metipranolol, mifepristone, Mikelan, Minims Metipranolol, Mirol, nipradilol, Nor Tenz, Ocupress, olmesartan, Ophtalol, pilocarpine nitrate, Piobaj, Rescula, RU486, Rysmon TG, SAD448, Saflutan, Shemol, Taflotan, tafluprost, tafluprost with timolol, Thiaboot, Timocomod, timolol, Timolol Actavis, timolol hemihydrate, timolol maleate, Travast, travoprost, Unilat, Xalacom, Xalatan or Zomilol. In addition, the drugs delivered to ocular tissues using the microneedle devices and methods disclosed herein which treat, prevent, and/or ameliorate ocular hypertension, as listed above, may be combined with one or more agents listed above or herein or with other agents known in the art.

In certain embodiments one or more drugs may be delivered to ocular tissues and/or into the suprachoroidal space via the systems and devices described herein. Delivery of one or more drugs into the suprachoroida lspace using the microneedle device described herein may be accomplished by using one or more microneedles. In addition, combinations of one of more drugs may be delivered to the suprachoroidal space using the microneedle device described herein in combination with delivery of one or more drugs via intravitreal (IVT) administration (e.g., intravitreal injection, intravitreal implant or eye drops). Methods of IVT administration are well known in the art. Examples of drugs that can be administered via IVT include, but are not limited to: A0003, A0006, Acedolone, AdPEDF, aflibercept, AG13958, aganirsen, AGN208397, AKB9778, AL78898A, amyloid P, Angiogenesis Inhibitor Gene Therapy, ARC1905, Aurocort, bevasiranib sodium, brimonidine, Brimonidine, brimonidine tartrate, bromfenac sodium, Candy5, CERE140, Ciganclor, CLT001, CLT003, CLT004, CLT005, complement component 5 aptamer (pegylated), complement factor D antibody, Cortiject, c-raf 2-methoxyethyl phosphorothioate oligonucleotide, cyclosporine, triamcinolone, DE109, denufosol tetrasodium, dexamethasone, dexamethasone phosphate, disitertide, DNA damage inducible transcript 4 oligonucleotide, E10030, ecallantide, EG3306, Eos013, ESBA1008, ESBA105, Eylea, FCFD4514S, fluocinolone acetonide, fms-related tyrosine kinase 1 oligonucleotide, fomivirsen sodium, fosbretabulin tromethamine, FOV2301, FOV2501, ganciclovir, ganciclovir sodium, GS101, GS156, hyaluronidase, IBI20089, iCo007, Iluvien, INS37217, Isonep, JSM6427, Kalbitor, KH902, lerdelimumab, LFG316, Lucentis, M200, Macugen, Makyueido, Microplasmin, MK0140, MP0112, NCX434, neurotrophin 4 gene, OC10X, ocriplasmin, ORA102, Ozurdex, P144, P17, Palomid 529, pazopanib hydrochloride, pegaptanib sodium, Plasma Kallikrein Inhibitors, platelet-derived growth factor beta polypeptide aptamer (pegylated), POT4, PRM167, PRS055, QPI1007, ranibizumab, resveratrol, Retilone, retinal pigment epithelium-specific protein 65 kDa gene, Retisert, rod derived cone viability factor, RPE65 Gene Therapy, RPGR Gene Therapy, RTP801, Sd-rxRNA, serpin peptidase inhibitor clade F member 1 gene, Sirna027, sirolimus, sonepcizumab, SRT501, STP601, TG100948, Trabio, triamcinolone, triamcinolone acetonide, Trivaris, tumor necrosis factor antibody, VEGF/rGel-Op, verteporfin, Visudyne, Vitrase, Vitrasert, Vitravene, Vitreals, voloximab, Votrient, XG102, Xibrom, XV615, and Zybrestat. Accordingly, the methods of the present invention include administrating via IVT one or more of the drugs listed above in combination with one or more drugs disclosed herein administered into the suprachoroidal space using the microneedle device described herein.

In some embodiments, the drug is formulated for storage and delivery via the kits, microneedle devices, and methods described herein. The "drug formulation" is a formulation of a drug, which typically includes one or more pharmaceutically acceptable excipient materials known in the art. The term "excipient" refers to any non-active ingredient of the formulation intended to facilitate handling, stability, dispersibility, wettability, release kinetics, and/or injection of the drug. In one embodiment, the excipient may include or consist of water or saline.

In some embodiments, the fluid drug formulation includes microparticles or nanoparticles, each of which can include at least one drug. Desirably, the microparticles or nanoparticles provide for the controlled release of drug into the ocular tissue. As used herein, the term "microparticle" encompasses microspheres, microcapsules, microparticles, and beads, having a number average diameter of 1 to 100 µm, most preferably 1 to 25 µm. The term "nanoparticles" are particles having a number average diameter of 1 to 1000 nm. Microparticles may or may not be spherical in shape. "Microcapsules" are defined as microparticles having an outer shell surrounding a core of another material. The core can be liquid, gel, solid, gas, or a combination thereof. In one case, the microcapsule may be a "microbubble" having an outer shell surrounding a core of gas, wherein the drug is disposed on the surface of the outer shell, in the outer shell itself, or in the core. Microbubbles may respond to acoustic vibrations as known in the art for diagnosis and/or can be used to burst the microbubble to release its payload at/into a select ocular tissue site. "Microspheres" can be solid spheres, can be porous and include a sponge-like or honeycomb structure formed by pores or voids in a matrix material or shell, or can include multiple discrete voids in a matrix material or shell. The microparticle or nanoparticles may further include a matrix material. The shell or matrix material may be a polymer, amino acid, saccharide, or other material known in the art of microencapsulation.

The drug-containing microparticles or nanoparticles may be suspended in an aqueous or non-aqueous liquid vehicle. The liquid vehicle may be a pharmaceutically acceptable aqueous solution, and optionally may further include a surfactant. The microparticles or nanoparticles of drug themselves may include an excipient material, such as a polymer, a polysaccharide, a surfactant, etc., which are known in the art to control the kinetics of drug release from particles.

In one embodiment, the fluid drug formulation further includes an agent effective to degrade collagen or GAG fibers in the sclera, which may enhance penetration/release of the drug into the ocular tissues. This agent may be, for example, an enzyme, such a hyaluronidase, a collagenase, or a combination thereof. In a variation of this method, the enzyme is administered to the ocular tissue in a separate step from—preceding or following—infusion of the drug. The enzyme and drug are administered at the same site.

In another embodiment, the drug formulation is one that undergoes a phase change upon administration. For instance, a liquid drug formulation may be injected through hollow microneedles into the suprachoroidal space, where it then gels and the drug diffuses out from the gel for controlled release.

While the embodiments and methods herein describe delivering a medicament to a target tissue, the embodiments described herein can be configured to facilitate a biopsy procedure and/or removal of a substance from a target location.

While the embodiments have been described above in use on ocular tissue, in some instances, the embodiments and methods described herein can be used on any other suitable bodily tissue. For example, in some instances, the use of an adjustable length needle can be beneficial in conjunction with standard phlebotomy techniques during drug infusion and/or blood draw from a vein. Thus, while the embodiments and methods are specifically described above in use on ocular tissue, it should be understood that the embodiments and methods have been presented by way of example only, and not limitation.

Although various embodiments have been described as having particular features and/or combinations of components, other embodiments are possible having a combination of any features and/or components from any of embodiments where appropriate. For example, although the kit 1000 is shown and described as including an injector assembly 1100, a set of needle assemblies 1160A and 1160B, a medicament container 1200, a container adapter 1220, and a packing assembly 1300, in other embodiments, a kit can include any subset of the components described herein. For example, in some embodiments, a kit can include a single injector assembly disposed within a tray assembly, but can be devoid of a medicament container.

In some embodiments, a kit can include multiple medicament containers.

In some embodiments, an apparatus includes a first tray member, a second tray member, and a lid. The first tray member has a first portion and a second portion. The first portion defines a first volume, and the second portion defines a second volume configured to receive a medicament container. The second tray member defines a third volume having a side wall including a retention portion configured to retain an ocular injector within the third volume. The second tray member is coupled within first volume such that the side wall of the second tray member and a side wall of the first tray member enclose the ocular injector. The lid is coupled to the first tray member about the first volume, and is constructed from a material formulated to maintain sterility of the first volume.

In some embodiments, the first tray member defines an opening providing access to the first volume. The second tray member defines an opening providing access to the third volume. The opening of the first tray member is obstructed by the sidewall of the second tray member, and the opening of the second tray member is placed against the sidewall of the first tray member when the second tray member is disposed within the first tray member.

In some embodiments, the first tray member includes a locking portion configured to matingly engage a flange of the second tray member to retain the second tray member within the first volume of the first tray member. An outer surface of the first tray member includes an actuation portion against which an actuation force is applied. The actuation portion is configured to deform to release the flange from the locking portion when the actuation force is applied.

What is claimed is:

1. An apparatus, comprising:
a first tray member having a plurality of walls that define a first volume and an opening that provides access to the first volume;
a second tray member having a plurality of walls that define a second volume and an opening that provides access to the second volume, a wall from the plurality of walls of the second tray member including a retainer extending from the wall from the plurality of walls of the second tray member and configured to retain at least a portion of a medicament delivery device within the second volume, the opening of the second tray member providing removal access of the medicament delivery device from within the second volume,
in a first configuration, the second tray member is disposed within the first volume of the first tray member such that access to the medicament delivery device within the second volume is inhibited by a wall from the plurality of walls of the first tray member,
in a second configuration, the second tray member is physically separate from the first tray member to allow access to the medicament delivery device within the second volume; and
a cover member coupled to the first tray member about the opening, the cover member configured to maintain sterility of the first volume.

2. The apparatus of claim 1, wherein the opening of the first tray member is obstructed by the wall of the second tray member and the opening of the second tray member is covered by the wall of the first tray member when the second tray member is disposed within the first tray member such that removal access of the medicament delivery device from within the second volume is inhibited.

3. The apparatus of claim 2, wherein
an outer surface of the wall of the second tray member is configured to be placed, after being removed from the first volume, on a work surface within a sterile field such that the opening of the second tray member is exposed opposite the work surface.

4. The apparatus of claim 1, wherein:
the first tray member includes a locking portion configured to matingly engage a flange of the second tray member to couple the second tray member within the first volume of the first tray member; and
an outer surface of the first tray member including an actuation portion against which an actuation force is applied, the actuation portion configured to deform to release the flange from the locking portion when the actuation force is applied.

5. The apparatus of claim 1, wherein:
the first tray member defines a protrusion; and
the retainer of the second tray member defines a retainer opening configured to receive a portion of the medicament delivery device, the protrusion and the retainer configured to maintain the medicament delivery device in a fixed position within the second volume when the second tray member is disposed within the first tray member.

6. The apparatus of claim 5, wherein:
the medicament delivery device is a medical injector;
the retainer is a first retainer defining a first retainer opening configured to receive a first portion of a barrel of the medical injector; and
the second tray member includes a second retainer defining a second retainer opening configured to receive a second portion of the barrel of the medical injector, the protrusion of the first tray member configured to engage a third portion of the barrel of the medical injector when the second tray member is disposed within the first tray member, the third portion of the barrel between the first portion and the second portion.

7. The apparatus of claim 5, wherein:
the medicament delivery device is a medical injector;
the protrusion is a first protrusion;
the retainer is a first retainer;
the wall of the first tray member includes a second protrusion; and the second tray member includes a second retainer configured to receive a portion of a needle assembly, the second protrusion and the second retainer configured to maintain the needle assembly in a fixed needle position within the third volume, spaced apart from the medical injector.

8. The apparatus of claim 1, wherein the first tray member defines a container volume configured to receive a medicament container, the container volume being exposed when the cover member is coupled to the first tray member, the apparatus further comprising:
a sleeve configured to be disposed about the first tray member when the second tray member is coupled within first volume, the sleeve configured to cover the container volume and a portion of the cover member disposed about the first volume.

9. The apparatus of claim 8, wherein:
the cover member includes an indicium associated with at least one of the medicament delivery device or the medicament container; and
the sleeve defines an opening, the opening aligned with the cover member when the sleeve is disposed about the first tray member such that the indicium is visible through the opening.

10. The apparatus of claim 8, further comprising:
the medicament container containing a medicament, the medicament including at least one of triamcinolone or triamcinolone acetonide.

11. The apparatus of claim 1, wherein in the first configuration, access to the medicament delivery device within the second volume is inhibited based at least in part collectively by an inner surface of the wall of the second tray member and an inner surface of a wall of the first tray member.

12. The apparatus of claim 1, wherein the retainer extends from the wall of the second tray member towards an interior portion of the first tray member when in the first configuration.

13. An apparatus, comprising:
a first tray member having a first plurality of side walls and a first bottom wall disposed between the first plurality of side walls, the first plurality of side walls and the first bottom wall collectively defining a first volume and an opening opposite the first bottom wall and that provides access to the first volume; and
a second tray member having a second plurality of side walls and a second bottom wall disposed between the second plurality of side walls, the second plurality of side walls and the second bottom wall collectively defining a second volume and an opening opposite the second bottom wall and that provides access to the second volume, the second tray member including a retainer extending from the second bottom wall towards the opening of the second tray member, the retainer being configured to retain a medicament delivery device within the second volume, the second tray member configured to be coupled within the first volume of the first tray member such that (1) the medicament delivery device is disposed within the first volume between an inner surface of the first bottom wall and an inner surface of the second bottom wall, and (2) the retainer extends towards the first bottom wall of the first tray member.

14. The apparatus of claim 13, wherein the medicament delivery device is any one of a syringe, a pen injector, a transdermal delivery device, an inhaler, or a nebulizer.

15. The apparatus of claim 13, further comprising:
a cover member configured to be coupled to the first tray member about the first volume, the cover member configured to maintain sterility of the first volume, the first tray member defining a container volume that is configured to receive a medicament container; and
a sleeve configured to be disposed about the first tray member when the second tray member is coupled within the first volume of the first tray member, the sleeve configured to cover the container volume and a portion of the cover member disposed about the first volume.

16. The apparatus of claim 13, wherein the second tray member is configured to be coupled within the first volume such that the second bottom wall of the second tray member and the first bottom wall of the first tray member substantially completely enclose the medicament delivery device within the first volume.

17. The apparatus of claim 13, wherein:
the first tray member includes a locking portion configured to matingly engage a flange of the second tray member to couple the second tray member within the first volume of the first tray member,
an outer surface of the first tray member including an actuation portion against which an actuation force is applied, the actuation portion configured to deform to release the flange from the locking portion when the actuation force is applied.

18. The apparatus of claim 13, wherein:
a protrusion extends from the wall of the first tray member; and
the retainer of the second tray member defines a retainer opening configured to receive a portion of the medicament delivery device, the protrusion and the retainer configured to maintain the medicament delivery device in a fixed position within the second volume when the second tray member is disposed within the first tray member.

19. The apparatus of claim 18, wherein:
the medicament delivery device is a medical injector;
the protrusion is a first protrusion;
the retainer is a first retainer;
the first bottom wall of the first tray member includes a second protrusion; and
the second tray member includes a second retainer configured to receive a portion of a needle assembly, the second protrusion and the second retainer configured to maintain the needle assembly in a fixed needle position within the second volume, spaced apart from the medical injector.

20. The apparatus of claim 18, wherein a longitudinal axis of the medicament delivery device is substantially parallel to the second bottom wall of the second tray member when the medicament delivery device in the fixed position within the second volume.

21. A method, comprising:
orienting a tray assembly such that an opening defined by a first tray member is spaced apart from and facing a sterile surface, the tray assembly including the first tray member and a second tray member, the first tray member defining a first volume, the opening of the first tray member providing access to the first volume, the second tray member defining a second volume within which a medicament delivery device is retained, the second tray member coupled within the first volume such that a wall of the second tray member and a wall of the first tray member enclose the medicament delivery device; and without direct contact by an operator with the second tray member, manipulating the first tray member to release the second tray member from within the first volume to allow a gravitational force to assist in placing an outer surface of the wall of the second tray member on the sterile surface such that an opening defined by the second tray member is facing opposite the sterile surface thereby providing access to the medicament delivery device via the opening defined by the second tray member, a retainer of the second tray member maintaining the medicament delivery device in a fixed position within the second volume.

22. The method of claim 21, further comprising:
removing, before the orienting, a cover member from about the first volume, the cover member constructed from a material formulated to maintain sterility of the first volume.

23. The method of claim 22, wherein the first tray member defines a container volume within which a medicament container is retained, the medicament container being exposed when the cover member is coupled to the first tray member, the method further comprising:
removing a sleeve from about the tray assembly before the removing the cover member from about the first volume,
the cover member including an indicium associated with at least one of the medicament delivery device or the medicament container, the sleeve defining an opening aligned with the cover member when the sleeve is disposed about the tray assembly member such that the indicium is visible through the opening.

24. The method of claim 21, wherein:
the first tray member includes a locking portion configured to matingly engage a flange of the second tray member to couple the second tray member within the first volume of the first tray member; and
the releasing includes applying an actuation force against an outer surface of the first tray member to deform the locking portion to release the flange from the locking portion.

25. The method of claim 24, wherein:
the releasing is performed without contact between a user applying the actuation force and the second tray member.

26. The method of claim 24, wherein the outer surface of the second tray member is placed on the sterile surface after the releasing in response to the actuation force and the gravitational force.

27. The method of claim 26, wherein the wall of the second tray member includes the outer surface and a lateral portion that extends from and surrounds the outer surface, the wall portion defining, in part, the second volume, the lateral portion providing a barrier to preserve the integrity of the second volume.

28. The method of claim 21, wherein the medicament delivery device is a medical injector, the retainer is a first retainer, the second tray member includes a second retainer configured to receive a portion of a needle assembly, the second retainer configured to maintain the needle assembly in a fixed needle position within the second volume before the releasing, the method further comprising:
removing, after the releasing the second tray member, the medical injector from retainer; and
coupling the needle assembly to the medical injector.

29. The method of claim 21, wherein the first tray member defines a container volume within which a medicament container is retained, the medicament delivery device is a medical injector including a container adapter coupled to a distal end portion of a barrel, the method further comprising:
removing the medicament container from the container volume;
coupling, after the releasing the second tray member, the barrel of the medicament injector to the medical container via the container adapter; and
actuating the medical injector to withdraw a dose of medicament from the medicament container into the barrel.

30. The method of claim 29, wherein the medicament includes at least one of triamcinolone or triamcinolone acetonide.

* * * * *